(12) United States Patent
Brenneman et al.

(10) Patent No.: US 7,427,590 B2
(45) Date of Patent: Sep. 23, 2008

(54) NEUROTHROPHIC COMPONENTS OF THE ADNF I COMPLEX

(75) Inventors: Douglas E. Brenneman, North Wales, PA (US); Raquel Castellon, Norwalk, CA (US); Catherine Y. Spong, Arlington, VA (US); Janet M. Hauser, Bethesda, MD (US); Illana Gozes, Ramat Hasharon (IL)

(73) Assignees: The United States of America as represented by the Secretary of the Department of Health and Human Services, Washington, DC (US); Ramot at Tel-Aviv University, Ltd., Tel Aviv (IL)

( * ) Notice: Subject to any disclaimer, the term of this patent is extended or adjusted under 35 U.S.C. 154(b) by 443 days.

(21) Appl. No.: 10/489,515

(22) PCT Filed: Sep. 12, 2002

(86) PCT No.: PCT/US02/29146

§ 371 (c)(1),
(2), (4) Date: Oct. 14, 2004

(87) PCT Pub. No.: WO03/022226

PCT Pub. Date: Mar. 20, 2003

(65) Prior Publication Data

US 2005/0054837 A1    Mar. 10, 2005

Related U.S. Application Data

(60) Provisional application No. 60/322,760, filed on Sep. 12, 2001, provisional application No. 60/371,961, filed on Apr. 10, 2002.

(51) Int. Cl.
*A61K 38/03* (2006.01)
*A61K 38/04* (2006.01)
*A61K 38/08* (2006.01)
*A61K 38/10* (2006.01)
*C07K 4/12* (2006.01)
*C07K 7/06* (2006.01)
*C07K 7/08* (2006.01)

(52) U.S. Cl. .............................. 514/2; 514/13; 514/15; 530/300; 530/323; 530/326; 530/328

(58) Field of Classification Search ................ None
See application file for complete search history.

(56) References Cited

U.S. PATENT DOCUMENTS

| 5,767,240 | A | 6/1998 | Brenneman et al. |
| 6,174,862 | B1 | 1/2001 | Brenneman |
| 6,617,156 | B1 * | 9/2003 | Doucette-Stamm et al. ...................... 435/320.1 |

OTHER PUBLICATIONS

Rudinger, In. *Peptide Hormones*, J. A. Pazons, ed., University Park Press, Baltimore, 1976, pp. 1-7.*
Bassan, M., et al., "Complete Sequence of a Novel Protein Containing a Femtomolar-Activity-Dependent Neuroprotective Peptide," *Journal of Neurochemistry*, 1999, pp. 1283-1293, vol. 72, No. 3, Lippincott Williams & Wilkins, Inc., Philadelphia.
Brenneman, D., et al., "A Femtomolar-acting Neuroprotective Peptide," *The Journal of Clinical Investigation*, May 1996, pp. 2299-2307, vol. 97, No. 10.
Brenneman, D., et al., "Activity-Dependent Neurotrophic Factor: Structure-Activity Relationships of Femtomolar-Acting Peptides," *The Journal of Pharmacology and Experimental Therapeutics*, 1998, pp. 619-627, vol. 285, No. 2, USA.
Glazner, G., et al., "Activity-dependent neurotrophic factor: a potent regulator of embryonic growth and development," *Anat Embryol*, 1999, pp. 65-71, vol. 200, Springer-Verlag.
Gozes, I., et al., "Activity-Dependent Neurotrophic Factor (ADNF)," *Journal of Molecular Neuroscience*, 1996, pp. 235-244, vol. 7, Humana Press, Inc.
Gozes, I., et al., "Antiserum to activity-dependent neurotrophic factor produces neuronal cell death in CNS cultures: immunological and biological specificity," *Developmental Brain Research*, 1997, pp. 167-175, vol. 99, Elsevier Science B.V.

* cited by examiner

*Primary Examiner*—Jeffrey Stucker
*Assistant Examiner*—Stephen Gucker
(74) *Attorney, Agent, or Firm*—Townsend and Townsend and Crew LLP

(57) ABSTRACT

This invention relates to Activity Dependent Neurotrophic Factor I complex (ADNF I complex) and polypeptides of this complex, which produce their neurotrophic effects through multiple proteases intrinsic to the ADNF I complex. The invention also relates to pharmaceutical compositions comprising ADNF I complex polypeptides, as well as methods for reducing neuronal cell death in vitro and in vivo, methods for treating oxidative stress in a patient, methods for reducing a condition associated with fetal alcohol syndrome in a subject, and methods of enhancing learning and memory both pre- and post-natally, all of which methods use the ADNF I complex polypeptides of the invention.

16 Claims, 34 Drawing Sheets

ADNF Complex

Effect of 14 kDa peak from e-CAP/SDS Capillary Electrophoresis on Neuronal Survival: Neuronal Cell Counts vs CFDA ADNF Complex ADNF Complex NNST Peptide increases Neuronal Survival in TTX-Treated Cerebral Cortical Cultures: Neuronal Cell Counts vs CFDA ADNF Complex ADNF Complex ADNF Complex ADNF Complex ADNF Complex

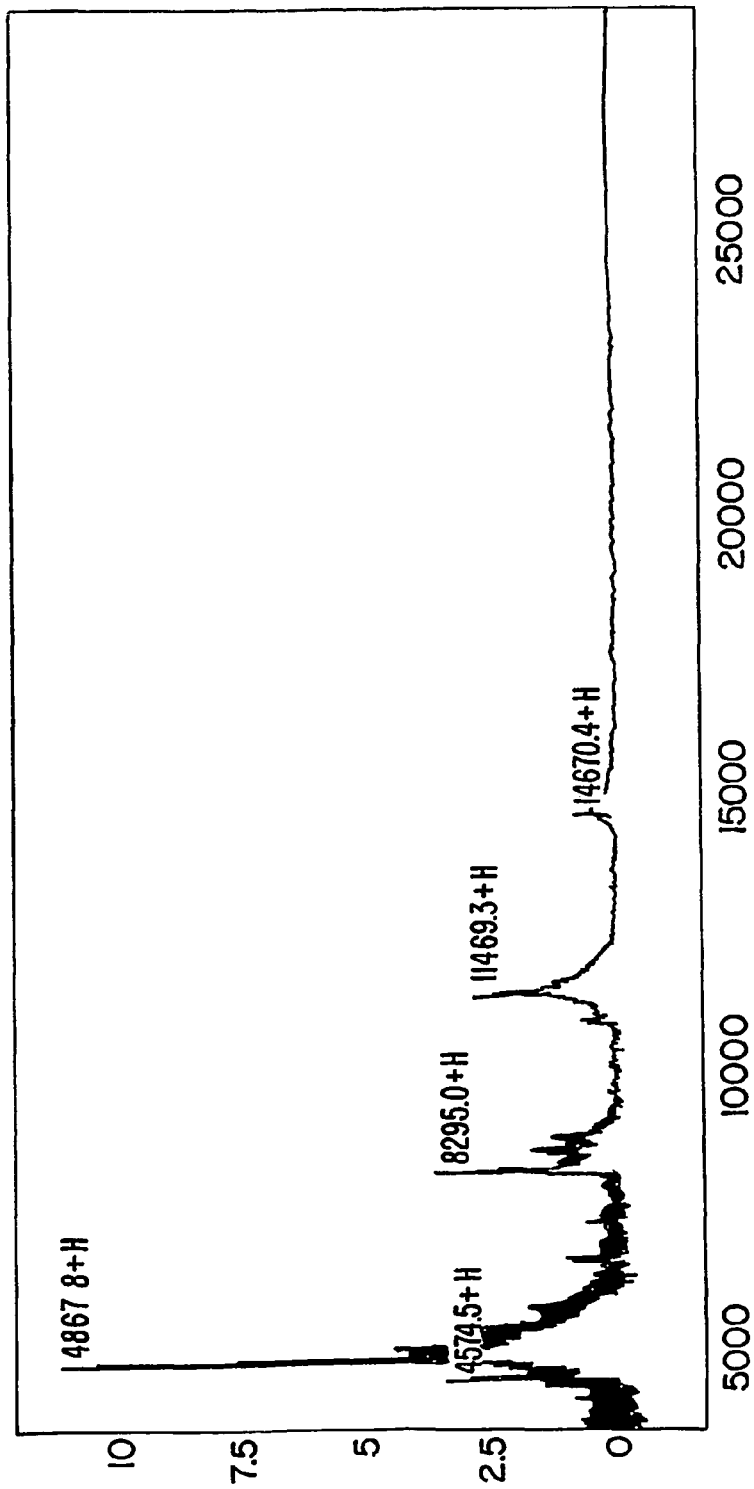

ADNF Complex

SEQUENCE LISTING

```
<160> NUMBER OF SEQ ID NOS: 24

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence from component
      II, WSD

<400> SEQUENCE: 1

Trp Ser Asp Val Gly Val Ser Ser Gly Ser Ala Pro Asp Ala Phe Lys
 1               5                  10                  15
```

```
<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, ADNF I complex
      tryptic digest peptide from component I, NNST

<400> SEQUENCE: 2

Asn Asn Ser Thr Thr Tyr Ala Pro Ile Ser Ala Asn Val Ser Thr Ala
 1               5                  10                  15

Leu Gly Ser Thr Ala Ala Leu Pro Thr Ala Ala Gly Pro Val
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence from component I,
      NFL

<400> SEQUENCE: 3

Asn Phe Leu Thr Ser His Tyr Ser Ala Ala Asn Ser Val Val Gly Gly
 1               5                  10                  15

Thr Asn Pro Gly Lys
            20

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, ADNF I complex
      tryptic digest peptide, PSG

<400> SEQUENCE: 4

Asn Pro Ser Gly Thr Asp Trp Leu Asn Thr Asn Asn Gln Ala Asn Pro
 1               5                  10                  15

Phe Asn

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, GPT

<400> SEQUENCE: 5

Leu Val Pro Leu Thr Pro Ile Asn Arg
 1               5

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence
```

```
<220> FEATURE:
<221> NAME/KEY: MOD_RES
<222> LOCATION: (6)
<223> OTHER INFORMATION: Xaa = any amino acid

<400> SEQUENCE: 6

Val Leu Gln Ala Val Xaa Gly Ala Asp Ser Asn Val Ala Phe Gln Gly
 1               5                  10                  15

Lys Val Ile Tyr Arg Ser Glu Ser Ser Gly Thr Ser Glu Leu Leu Thr
            20                  25                  30

Arg

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, ADNF I complex
      tryptic digest peptide, GPT

<400> SEQUENCE: 7

Gly Pro Thr Ala Asp Ile Thr Leu Thr Lys
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, GTP
<220> FEATURE:
<221> NAME/KEY: MOD_RES
<222> LOCATION: (6)
<223> OTHER INFORMATION: Xaa = any amino acid

<400> SEQUENCE: 8

Gly Thr Pro Thr Gly Xaa Gly Pro Leu Ile Gln
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, VDP

<400> SEQUENCE: 9

Val Asp Pro Ala Ser Gly Tyr Pro Ile Val Gly Tyr Thr
 1               5                  10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, ADNF I complex
      tryptic digest peptide, truncated form of PSG

<400> SEQUENCE: 10

Pro Ser Gly Thr Asp Trp Leu Asn Thr
```

-continued

```
        1               5
```

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) complex
      polypeptide active core sequence, ADNF I complex
      tryptic digest peptide, SES

<400> SEQUENCE: 11

Ser Glu Ser Ser Gly Thr Ser Glu Leu Leu Thr Arg
  1               5                  10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) active
      core site, ADNF-9 or SAL

<400> SEQUENCE: 12

Ser Ala Leu Leu Arg Ser Ile Pro Ala
  1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:Activity
      Dependent Neuroprotective Protein (ADNP or ADNF
      III) active core site, NAP

<400> SEQUENCE: 13

Asn Ala Pro Val Ser Ile Pro Gln
  1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence:ADNF I
      agonist ADNF-14

<400> SEQUENCE: 14

Val Leu Gly Gly Gly Ser Ala Leu Leu Arg Ser Ile Pro Ala
  1               5                  10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence:ADNF I
      complex tryptic digest peptide, full length PSG peptide

<400> SEQUENCE: 15

Pro Ser Gly Thr Asp Trp Leu Asn Thr Asn Gln Ala Asn Pro Phe
  1               5                  10                  15
Asn

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence:ADNF I
     complex peptide, GAD

<400> SEQUENCE: 16

Gly Ala Asp Ser Asn Val Ala Phe Gln Gly Lys Val Ile Tyr Arg Ser
 1               5                  10                  15

Glu Ser Ser Gly Thr Ser Glu Leu Leu Thr Arg
            20                  25

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence:subtilisin,
     furin-type protease active site

<400> SEQUENCE: 17

Gly Thr Ser Ala Ala Leu Pro Thr Ala Ala Gly
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence:portion of
     NNST peptide from component I

<400> SEQUENCE: 18

Gly Ser Thr Ala Ala Leu Pro Thr Ala Ala Gly
 1               5                  10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:subtilisin
     from Bacillus, furin-type protease

<400> SEQUENCE: 19

Thr Ser His Pro Asp Leu Lys Asn Gln Ile Ile Gly Gly Lys Asn
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:portion of
     NFL peptide from component I

<400> SEQUENCE: 20

Thr Ser His Tyr Ser Ala Ala Asn Ser Val Val Gly Gly Thr Asn
 1               5                  10                  15

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence:eukaryotic aspartyl protease active site

<400> SEQUENCE: 21

Val Asp Val Asp Ser Gly Ser Ala Pro Ile Val Gly Phe
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence:portion of
      WSD peptide from component II

<400> SEQUENCE: 22

Val Gly Val Ser Ser Gly Ser Ala Pro Asp Ala Phe
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence:cysteine
      protease of early leaf senescence

<400> SEQUENCE: 23

Val Ala Thr Cys Ser Ser Tyr Pro Val Val Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence:portion of
      VDP peptide, component unknown

<400> SEQUENCE: 24

Val Asp Pro Ala Ser Gly Tyr Pro Ile Val Gly
1               5                   10

NEUROTHROPHIC COMPONENTS OF THE ADNF I COMPLEX

CROSS-REFERENCES TO RELATED APPLICATIONS

This application is a National Stage of International Application PCT/US02/29146, filed Sep. 12, 2002 which claims priority to U.S.S.N. 60/322,760, filed Sep. 12, 2001, and U.S.S.N. 60/371,961, filed Apr. 10, 2002, herein each incorporated by reference in their entirety.

This application is related to U.S.S.N. 07/871,973 filed Apr. 22, 1992, now U.S. Pat. No. 5,767,240; U.S.S.N. 08/342,297, filed Oct. 17, 1994 (published as WO96/11948), now U.S. Pat. No. 6,174,862; U.S.S.N. 60/037,404, filed Feb. 7, 1997 (published as WO98/35042); U.S.S.N. 09/187,330, filed Nov. 11, 1998 (published as WO00/27875), now U.S. Pat. No. 6,613,740; U.S.S.N. 09/267,511, filed Mar. 12, 1999 (published as WO 00/53217), now U.S. Pat. No. 6,933,277; U.S.S.N. 60/149,956, filed Aug. 18, 1999 (published as WO01/12654, entered National Stage as USSN 10/049,587); U.S.S.N. 60/208,944, filed May 31, 2000; U.S.S.N. 60/267,805, filed Feb. 8, 2001; and PCT 01/17758, filed May 31, 2001, entered National Stage as USSN 10/296,849; herein each incorporated by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to Activity Dependent Neurotrophic Factor I complex (ADNF I complex) and polypeptides of this complex, which produce their neurotrophic effects through multiple proteases intrinsic to the ADNF I complex. The invention also relates to pharmaceutical compositions comprising ADNF I complex polypeptides, as well as methods for reducing neuronal cell death in vitro and in vivo, methods for treating oxidative stress in a patient, methods for reducing a condition associated with fetal alcohol syndrome in a subject, and methods of enhancing learning and memory both pre- and post-natally, all of which methods use the ADNF I complex polypeptides of the invention.

BACKGROUND OF THE INVENTION

Neuronal cell death has been associated with various clinical conditions and diseases. These conditions and diseases include, for example, neurodegenerative diseases such as Alzheimer's disease, AIDS-related dementia, Huntington's disease, and Parkinson's disease. Neuronal cell death has been also associated with developmental retardation and learning impairments. These diseases and conditions are severely debilitating and have a lifelong impact on individuals diagnosed with such diseases and conditions.

It has previously been reported that Activity Dependent Neurotrophic Factor (ADNF) polypeptides can be used to prevent or reduce neuronal cell death. Activity Dependent Neurotrophic Factor I (ADNF I) polypeptide is secreted by astroglial cells in the presence of vasoactive intestinal peptide (VIP). The ADNF I polypeptide exhibits survival-promoting activity for neurons at surprisingly low, femtomolar concentrations (Brenneman & Gozes, *J. Clin. Invest.* 97:2299-2307 (1996)). Further studies identified peptide fragments of ADNF I that mimic the neurotrophic and neuroprotective properties of ADNF I. The shortest peptide (i.e., the active core site) that captured the survival-promoting activity of ADNF I was the peptide SALLRSIPA, designated as ADNF-9 or SAL (Brenneman et al., *J. Pharm. Exp. Therp.* 285:619-627 (1998)). Studies of related molecules to the ADNF I polypeptide resulted in the discovery of Activity Dependent Neuroprotective Protein (called ADNP or ADNF III interchangeably). This protein was cloned (Bassan et al., *J. Neurochem.* 72:1283-1293 (1999)) and was found to have an active peptide similar in biological activity to SAL. This peptide (i.e., the active core site) was NAPVSIPQ, designated as NAP.

ADNF polypeptides have been shown to prevent neuronal cell death both in vitro and in vivo. For example, ADNF polypeptides have been shown to prevent neuronal cell death associated with tetrodotoxin (electrical blockade), the β-amyloid peptide (the Alzheimer's disease neurotoxin), N-methyl-D-aspartate (excitotoxicity), and the human immune deficiency virus envelope protein. In addition, daily injections of ADNF polypeptides to newborn apolipoprotein E-deficient mice accelerated the acquisition of developmental reflexes and prevented short-term memory deficits. See, e.g., Bassan et al., *J. Neurochem.* 72:1283-1293 (1999). Moreover, pretreatment with ADNF polypeptides has been previously shown to reduce numerous or various conditions associated with fetal alcohol syndrome in a subject. See, U.S.S.N. 09/265,511, filed Mar. 12, 1999. now U.S. Pat. No. 6,933,277.

Although ADNF polypeptides have unlimited potential as neuroprotectants and/or therapeutic agents, it would be advantageous to provide additional ADNF polypeptides that have different properties from the known ADNF polypeptides. For example, availability of a number of ADNF polypeptides with different affinities for their receptors would allow targeting specific receptors in different cell types. Furthermore, additional ADNF polypeptides would aid in designing a drug treatment regime that can be individually tailored for each patient affected by neurodegenerative disorders. Finally, knowledge regarding the mechanism of action of ADNF would be useful for aiding in drug treatment for patients affected by neurodegenerative disorders.

SUMMARY OF THE INVENTION

The invention demonstrates for the first time that the neuroprotective action of the ADNF I complex is associated with protease activity. The ADNF I complex has at least three, distinct survival promoting peaks or components isolated by N-CHO capillary electrophoresis (see, e.g., FIG. 2). The survival promoting activity of components I and III of the ADNF I complex are inhibited by E-64, an irreversible cysteine protease inhibitor, and the survival promoting activity of component II of the ADNF I complex is inhibited by peptstatin A, an inhibitor of aspartyl proteases. The experiments conducted herein demonstrate that component II is a calcium-dependent protease. This component can be detected with a cathepsin D fluorogenic substrate: Bz-Arg-Gly-Phe-Phe-Pro-4mβNA, HCL. Inactivation of ADNF is mediated through an intrisic subtilisin-like protease in the ADNF I complex, which ADNF I lytic activity is activated at pH>8.0.

The present invention is also based upon a surprising discovery that new ADNF I complex polypeptides are effective for reducing neuronal cell death, for reducing oxidative stress, for reducing condition(s) associated with fetal alcohol syndrome in a subject, for enhancing learning and memory, both pre- and post-natally, and for other conditions. The ADNF I complex polypeptides contain active sites and provide neuroprotective and growth-promoting functions. These ADNF I complex polypeptides are from subunits of ADNF I and/or accessory molecules of ADNF L which co-isolate with ADNF I from conditioned medium of VIP-stimulated astrocyte cultures. Antiserum to these polypeptides blocks the action of ADNF I and ADNF I complex polypeptides.

In one aspect, the present invention provides an Activity Dependent Neurotrophic Factor I complex (ADNF I) polypeptide, the ADNF I polypeptide comprising an amino acid sequence or a fragment thereof selected from the group consisting of:

| | |
|---|---|
| WSDVGVSSGSAPDAFK | (SEQ ID NO:1) |
| NNSTTYAPISANVSTALGSTAALPTAAGPV | (SEQ ID NO:2) |
| NFLTSHYSAANSVVGGTNPGK | (SEQ ID NO:3) |
| NPSGTDWLNTNNQANPFN | (SEQ ID NO:4) |
| LVPLTPINR | (SEQ ID NO:5) |
| VLQAVXGADSNVAFQGKVIYRSESSGTSELLTR | (SEQ ID NO:6) |
| GPTADITLTK | (SEQ ID NO:7) |
| GTPTGXGPLIQ | (SEQ ID NO:8) |
| VDPASGYPIVGYT | (SEQ ID NO:9) |
| PSGTDWLNT | (SEQ ID NO:10) |
| and | |
| SESSGTSELLTR. | (SEQ ID NO:11) |

In one embodiment, the polypeptide is covalently linked to a lipophilic moiety, e.g., fatty acyl groups and steroids.

In another embodiment, the polypeptide comprises at least one D-amino acid. In another embodiment, either an N-terminal amino acid or a C-terminal amino acid of the polypeptide is a D-amino acid. In another embodiment, both N-terminal and C-terminal amino acids of the polypeptide are D-amino acids. In another embodiment, the polypeptide comprises all D-amino acids.

In another embodiment, the ADNF I polypeptide comprises up to about 20 amino acids at each of an N-terminus and a C-terminus of the polypeptide.

In another aspect, the present invention provides an antibody that specifically binds to the ADNF I complex polypeptide described above.

In another aspect, the present invention provides a nucleic acid encoding an amino acid sequence comprising an ADNF I complex polypeptide as described above.

In another aspect, the present invention provides a pharmaceutical composition comprising a pharmaceutically acceptable excipient and an ADNF I complex polypeptide as described above.

In another embodiment, the ADNF I complex polypeptide is administered intranasally or orally. In another embodiment, the ADNF I complex polypeptide is encoded by a nucleic acid which is administered to the subject.

In one aspect, the present invention provides a method for preventing neuronal cell death, the method comprising contacting neuronal cells with at least one of the above described ADNF I complex polypeptides. In one embodiment, the neuronal cell death is in a patient infected with immunodeficiency virus. In another embodiment, the neuronal cell death is associated with excito-toxicity induced by N-methyl-D-aspartate stimulation. In yet another embodiment, the neuronal cell death is induced by the beta-amyloid peptide in a patient afflicted with Alzheimer's disease. In yet another embodiment, the neuronal cell death is induced by cholinergic blockade in a patient afflicted with Alzheimer's disease, which results in learning impairment. In another embodiment, the neuronal cells are selected from the group consisting of spinal cord neurons, hippocampal neurons, cerebral cortical neurons and cholinergic neurons.

In yet another aspect, the present invention provides a method for reducing oxidative stress in a patient, the method comprising administrating to the patient at least one of the ADNF I complex polypeptides described above in an amount sufficient to treat oxidative stress.

In yet another aspect, the present invention provides a method for reducing a condition associated with fetal alcohol syndrome in a subject who is exposed to alcohol in utero, the method comprising administering to the subject at least one ADNF I complex polypeptide described above in an amount sufficient to reduce a condition associated with fetal alcohol syndrome.

In one embodiment, the condition is selected from the group consisting of: a decreased body weight of a subject; a decreased brain weight of the subject; a decreased level of VIP mRNA of a subject; and death of a subject in utero.

In another aspect, the present invention provides a method for improving learning and/or memory in a subject, the method comprising the step of administering postnatally to the subject at least one ADNF I complex polypeptide described above in an amount sufficient to improve postnatal learning and/or memory of the subject.

In one embodiment, the subject is afflicted with a neuropathology. In another embodiment, the subject has Alzheimer's disease. In another embodiment, the subject has Down's syndrome. In another embodiment, the subject is normal. In another embodiment, the subject is old.

In another embodiment, the polypeptide improves short term or reference memory.

In another aspect, the present invention provides a method for improving learning and/or memory in a subject, the method comprising the step of administering prenatally to the subject at least one ADNF I complex polypeptide described above in an amount sufficient to improve prenatal learning and/or memory of the subject.

In one embodiment, the subject has mental retardation, a family history of mental retardation, Down's syndrome, or a mother who is at least 35 years of age when pregnant with the subject. In another embodiment, the ADNF I polypeptide is administered around the time of neural tube development and/or closure of the neural tube. In another embodiment, the ADNF I polypeptide is orally, nasally, or intraperitoneally administered to the mother during pregnancy.

BRIEF DESCRIPTION OF THE DRAWINGS

FIG. 16. ADNF I-like immunoreactivity in fiber-like structures in the basal forebrain of the newborn rat brain. Immunocytochemistry was performed with a rabbit anti-WSD. A 1:10,000 dilution of a 2 mg/ml IgG solution was used as the primary antibody. A rabbit Elite Vectastain kit was used for the staining (Vector Laboratories). Magnification: 20×.

FIG. 17. ADNF I-like immunoreactivity in the para abducens nucleus of the brainstem of the newborn rat brain. Immunocytochemistry with anti-WSD was performed as described for FIG. 16. Magnification: 20×.

With the addition of the substrate, the generation of fluorescence was measured automatically every 5 min in a Cytofluor (Perseptive Biosystems). All data was expressed as a change in arbitrary fluorescence units per 5 min. As shown in FIG. 28, in the presence of component II from ADNF I the increase in fluorescence was linear for 50 min (closed circles). There was no detectable change in fluorescence in the absence of component II (open circles). Each point is the mean±the standard error of three values.

DETAILED DESCRIPTION OF THE INVENTION

Introduction

Figure 1:
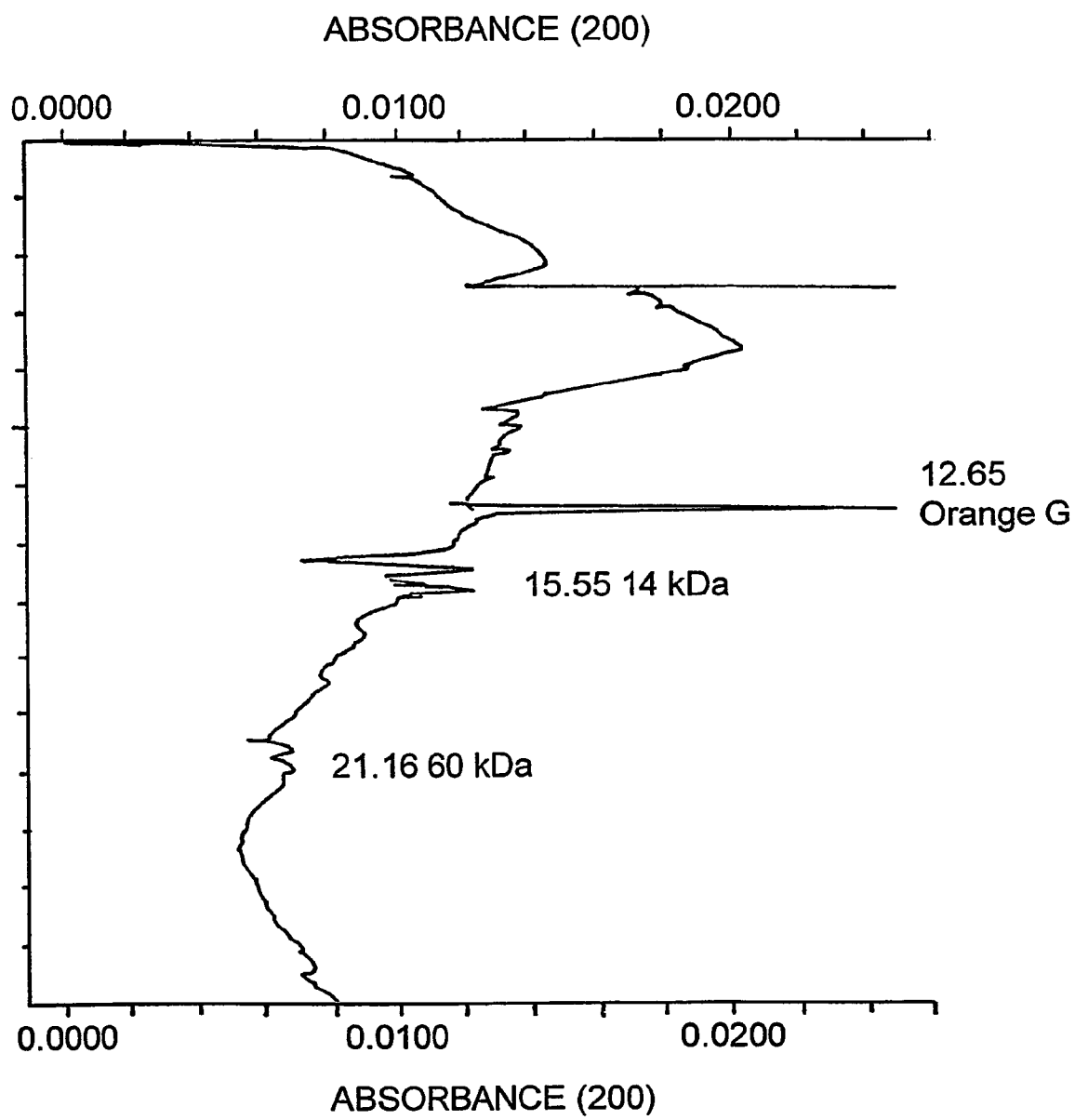
FIG. 1. Electropherogram of biochemically (Brenneman & Gozes, *J. Clin. Invest.* 97:2299-2304 (1996)) isolated ADNF I. The ADNF I peak is observed at 15.55 min and corresponds to the 14 kDa region as determined by molecular weight standards with the eCAP/SDS capillary (Beckman Instruments). Purified ADNF I was diluted 1:3 with water. The running and sample buffer for these analyses were with the eCAP/SDS kit (Beckmann Instruments). Electrophoresis was conducted with 8.1 kV constant voltage and with reversed polarity. The capillary consisted of sodium dodecyl sulfate coating with a 100 µM inside diameter, 47 cm in length (300 V/cm). The pressure injection of the sample was 70 sec at 80 psi. The peak at 12.26 is orange G, a column reference marker which acts a control to monitor column performance. The minor peak at 21.15 min corresponds to a peak of approximately 60 kD, which is likely an aggregate form of ADNF I. Sample was monitored with absorbance at 200 nm.

Proteases have major regulatory roles in the activation and inactivation of critical proteins/peptides that are important to cellular survival. Many neurodegenerative diseases are believed to involve the inappropriate regulation of activated cell death: apoptosis. The control of apoptotic death is now recognized to be largely under the control of caspases, cysteine proteases that regulate survival/death at checkpoints through intricate interacting cascades of intracellular events. The extracellular signals that regulate these pathways is an active area of research. In addition, proteases are known to cleave pro-hormones to activated forms. This body of knowledge indicates that hormones can be released in a less active form and activated by proteolytic cleavage. Importantly, the action of circulating proteins can also be inactivated by the action of proteases. Thus, proteases are recognized as major regulatory enzymes that control critical pathways important to development, homeostasis and disease.

The present application demonstrates that ADNF I produces its neurotrophic effects through multiple proteases intrinsic to the ADNF I multiple-component protein complex. ADNF I has been described as a complex of at least three components. The ADNF I components were demonstrated by the isolation of three distinct, survival-promoting peaks isolated by N-CHO capillary electrophoresis (see, e.g., FIG. 2). These peaks had very different EC50's in producing survival-promoting activity for tetrodotoxin treated neurons and each was neutralized by a distinct group of anti-peptides derived from ADNF I. In the present application, data is presented which shows that the neurotrophic activities of the ADNF components reside in their proteolytic actions.

In the present application, novel ADNF I peptides from the ADNF I complex are also provided. The amino acid composition of the ADNF I-related peptides were determined from trypsin digests of biochemically purified ADNF I as described in U.S. Pat. No. 5,767,270. The newly discovered peptides exhibited neuroprotective action from neuronal cell death produced by tetrodotoxin, a toxin that blocks electrical activity and which produces death by apoptosis. Inhibition of proteolytic activity or lowering the pH of ADNF I revealed other survival-promoting components of ADNF I. Novel peptides of the ADNF I complex were synthesized and confirmed to exhibit survival-promoting activity. The components of the ADNF I complex have been separated by N-CHO capillary electrophoresis and this method can be used to characterize the components of ADNF I.

Shorter peptides than that observed in the tryptic digests of the ADNF I complex can increase neuronal survival. These data indicate that core sequences reside within the digest peptides that can mimic both the parent digest peptide and the parent protein ADNF I. Furthermore, the addition of lipophilic moieties including fatty acyl groups and steroids to the above peptide structures are useful for therapeutic applications, as well as all D-amino acid forms of the above peptides and mixtures of D- and L-amino acids peptides.

Furthermore, antiserum made to some of these peptides produced neuronal cell death in cerebral cortical cultures and the anti-peptides from ADNF I complex blocked the survival-promoting action of ADNF I. The antisera to the ADNF I complex peptides were studied with immunohistochemistry to confirm their localization in the central nervous system and to further establish the characterization of the nature and uniqueness of these peptides and ADNF I. Antiserum to the peptides were shown to produce neuronal cell death in dissociated cerebral cortical cultures and all antiserum listed below prevented ADNF I-mediated-neuroprotection. These antiserum and their peptide antigens are therefore useful as diagnostic reagents to measure and distinguish ADNF I-like activity from other survival-promoting agents Because the above ADNF I complex peptides prevent apoptotic death, these peptides can be used for prevention of cell death produced by clinically relevant toxins where apoptosis is documented as a pathophysiological mechanism for the associated disease. These toxins include: beta amyloid peptide, excitatory amino acids, oxidative stress, ethanol, and gp 120, the external envelope protein from the human immunodeficiency virus. Clinical applications include: Alzheimer's disease, HIV-related dementia complex, stroke, head trauma, cerebral palsy, fetal alcohol syndrome and Parkinson's disease.

Definitions

The phrase "ADNF I complex polypeptide" or "ADNF I protein" or "ADNF I polypeptide" or "ADNF I peptide" refers to one or more polypeptides or acid or protease digest peptides from the ADNF I complex, which includes ADNF I, ADNF I subunits, and ADNF I co-factors that co-isolate with ADNF I from VIP-stimulated astrocyte cultures, using the methods described herein and in Brenneman & Gozes, *J. Clin. Invest.* 97:2299-2307 (1996). In one embodiment, an ADNF I complex polypeptide comprises an active core sequence having an amino acid sequence or a fragment thereof selected from the group consisting of:

WSDVGVSSGSAPDAFK (SEQ ID NO:1)

NNSTTYAPISANVSTALGSTAALPTAAGPV (SEQ ID NO:2)

-continued

NFLTSHYSAANSVVGGTNPGK (SEQ ID NO:3)

NPSGTDWLNTNNQANPFN (SEQ ID NO:4)

LVPLTPINR (SEQ ID NO:5)

VLQAVXGADSNVAFQGKVIYRSESSGTSELLTR (SEQ ID NO:6)

GPTADITLTK (SEQ ID NO:7)

GTPTGXGPLIQ (SEQ ID NO:8)

VDPASGYPIVGYT (SEQ ID NO:9)

PSGTDWLNT (SEQ ID NO:10)

and

SESSGTSELLTR, (SEQ ID NO:11)

or conservatively modified variants thereof that have neurotrophic/neuroprotective activity as measured with in vitro cortical neuron culture assays described by, e.g., Brenneman et al., *J. Pharmacol. Exp. Therp.* 285:629-627 (1998); Bassan et al., *J. Neurochem.* 72:1283-1293 (1999). An ADNF I complex polypeptide includes alleles, polymorphic variants, or interspecies homolog, or any subsequences thereof, that exhibit neuroprotective/neurotrophic action on, e.g., neurons originating in the central nervous system either in vitro or in vivo.

The term "ADNF I" refers to an activity dependent neurotrophic factor polypeptide or complex having a molecular weight of about 14,000 Daltons with a pI of 8.3±0.25. In one embodiment, ADNF I polypeptides have an active core site comprising an amino acid sequence of Ser-Ala-Leu-Leu-Arg-Ser-Ile-Pro-Ala (also referred to as "SALLRSIPA," "SAL," or "ADNF I-9"; SEQ ID NO:12). See, Brenneman & Gozes, *J. Clin. Invest.* 97:2299-2307 (1996), Glazner et al., *Anat. Embryol.* 200:65-71 (1999), Brenneman et al., *J. Pharm. Exp. Ther.* 285:619-27 (1998), Gozes & Brenneman, *J. Mol Neurosci.* 7:235-244 (1996), and Gozes et al., *Dev. Brain Res.* 99:167-175 (1997), all of which are herein incorporated by reference. Unless indicated as otherwise, "SAL" refers to a peptide having an amino acid sequence of Ser-Ala-Leu-Leu-Arg-Ser-Ile-Pro-Ala (SEQ ID NO:12), not a peptide having an amino acid sequence of Ser-Ala-Leu.

The terms "ADNF III" and "ADNP" refer to an activity dependent neurotrophic factor polypeptide having a molecular weight by western analysis of about 114 kDa (about 828 amino acid residues), a calculated molecular weight of 123, 562.8 daltons, and a theoretical pI of about 6.97. ADNF III polypeptides have an active core site comprising an amino acid sequence of Asn-Ala-Pro-Val-Ser-Ile-Pro-Gln (also referred to as "NAPVSIPQ," "NAP," or "ADNF III-8"; SEQ ID NO:13). See, Zamostiano et al., *J. Biol. Chem.* 276:708-714 (2001); Bassan et al., *J. Neurochem.* 72:1283-1293 (1999), incorporated herein by reference. Unless indicated as otherwise, "NAP" refers to a peptide having an amino acid sequence of Asn-Ala-Pro-Val-Ser-Ile-Pro-Gln (SEQ ID NO:13), not a peptide having an amino acid sequence of Asn-Ala-Pro.

The phrase "reducing neuronal cell death" refers to reduction, including prevention, of neuronal cell death. Reduction is a change of a parameter by about 10% to about 100%, preferably at least about 50%, and more preferably at least about 80% compared to that of the control (e.g., without treatment with, e.g., ADNF I complex polypeptides). The reduction of neuronal cell death can be measured by any methods known in the art. For example, ADNF I complex polypeptides that reduce neuronal cell death can be screened using the various methods described in U.S.S.N. 60/037,404, filed Feb. 27, 1997 (published as WO98/35042) and U.S.S.N. 09/187,330, filed Nov. 6, 1998, now U.S. Pat. No. 6,613,740, both of which are incorporated herein by reference.

The phrase "oxidative stress" in cells or tissues refers to enhanced generation of free radicals or reactive oxygen species (ROS) (such as α-hydroxy ethyl radical, superoxide radical, hydroxy radical, peroxy radical, and hydrogen peroxide) and/or a depletion in antioxidant defense system causing an imbalance between prooxidants and antioxidants. Enzymatic antioxidant system includes, e.g., superoxide dismutase, catalase, glutathione peroxidase, and glutathione reductase, and nonenzymatic antioxidants include, e.g., reduced glutathione, vitamin A, C, and E. See, Schlorff et al., *Alcohol* 17:97-105 (1999).

The phrase "reducing oxidative stress" refers to reduction, including prevention, of oxidative stress in cells and tissues. Reduction is a change of a parameter by about 10% to about 100%, preferably at least about 50%, and more preferably at least about 80% compared to that of the control (e.g., without treatment with, e.g., ADNF I complex polypeptides). The reduction in oxidative stress can be measured by any methods known in the art. For example, ADNF I complex polypeptides that reduce oxidative stress can be screened by using primary neurons treated with $FeSO_4$ in vitro as described infra. Also, ADNF I complex polypeptides that reduce oxidative stress can be screened using animals that ingested ethanol which is known to cause oxidative stress in cells and tissues. For example, the effects of ADNF I complex polypeptides on lipid peroxidation in plasma and/or antioxidant system of rats that ingested ethanol can be used. See, e.g., Schlorff et al., *Alcohol* 17:97-105 (1999).

The phrases "fetal alcohol syndrome" and "fetal alcohol effects" relate to various physical and mental conditions of an embryo, a fetus, or a subject who is exposed to alcohol in utero (e.g., whose mother consumed alcohol during pregnancy) in an amount sufficient to initiate the development of these conditions or to cause these conditions in the absence of prevention treatment, e.g., treatment with ADNF I complex polypeptides. Some of these conditions include, but are not limited to, the following:

skeletal deformities: deformed ribs and sternum; curved spine; hip dislocations; bent, fused, webbed, or missing fingers or toes; limited movement of joints; small head; facial abnormalities: small eye openings; skin webbing between eyes and base of nose; drooping eyelids; near sightedness; failure of eyes to move in same direction; short upturned nose; sunken nasal bridge; flat or absent groove between nose and upper lip; thin upper lip; opening in roof of mouth; small jaw; low-set or poorly formed ears; organ deformities: heart defects; heart murmurs; genital malformations; kidney and urinary defects; central nervous system handicaps: small brain; faulty arrangement of brain cells and connective tissue; mental retardation—usually mild to moderate, but occasionally severe; learning disabilities; short attention span; irritability in infancy; hyperactivity in childhood; poor body, hand, and finger coordination; and other abnormalities: brain weight reduction, body weight reduction, a higher rate of death in utero, and a decrease in the level of VIP (e.g., VIP mRNA).

The phrase "reducing a condition associated with fetal alcohol syndrome" refers to reduction, including prevention, of parameters associated with fetal alcohol syndrome. Reduction is a change of a parameter by about 10% to about 100%, preferably at least about 50%, and more preferably at least about 80% compared to that of the control (e.g., exposed to alcohol in utero without any treatment, e.g., treatment with ADNF I complex polypeptides). The parameters can be any physical or mental condition listed above. For example, they can be: (1) the percentage of fetus death, (2) fetal weights and fetal brain weights, (3) the level of VIP (e.g., VIP mRNA) in embryos, (4) learning and/or memory, and (5) the glutathione level.

The phrase "a subject with fetal alcohol syndrome" relates to an embryo, a fetus, or a subject, in particular a human, who is exposed to alcohol in utero and who has fetal alcohol syndrome or who is at risk or in danger of developing, due to maternal alcohol consumption, any of the conditions related to fetal alcohol syndrome, such as the effects described above.

Various parameters can be measured to determine if an ADNF I complex polypeptides or a mixture of ADNF I complex polypeptides improves performance of a subject, when the peptide is administered either pre- or post-natally (e.g., learning and memory). For example, the degree of learning deficits can be compared between the control (e.g., untreated with ADNF I complex polypeptides) and a group pretreated with ADNF I complex polypeptides, either pre- or post-natally. The phrase "improving learning and memory" refers to an improvement or enhancement of at least one parameter that indicates learning and memory. Improvement or enhancement is change of a parameter by at least 10%, optionally at least about 20%, at least about 30%, at least about 40%, at least about 50%, at least about 60%, at least about 70%, at least about 80%, at least about 90%, at least about 100%, at least about 150%, at least about 200%, etc. The improvement of learning and memory can be measured by any methods known in the art. For example, ADNF I complex polypeptides that improve learning and memory can be screened using Morris water maze (see, also, Gozes et al., *Proc. Natl. Acad. Sci. USA* 93:427-432 (1996); Gozes et al., *J. Pharmacol. Exp. Therap.* 293: 1091-1098 (2000)). Memory and learning can also be screened using any of the methods described herein or other methods that are well known to those of skill in the art, e.g., the Randt Memory Test, the Wechler Memory Scale, the Forward Digit Span test, or the California Verbal Learning Test.

The term "memory" includes all medical classifications of memory, e.g., sensory, immediate, recent and remote, as well as terms used in psychology, such as reference memory, which refers to information gained from previous experience, either recent or remote (see, e.g., *Harrison's Principles of Internal Medicine*, volume 1, pp. 142-150 (Fauci et al., eds., 1988).

Pathologies or neuropathologies that would benefit from therapeutic and diagnostic applications of this invention include, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

The term "spatial learning" refers to learning about one's environment and requires knowledge of what objects are where. It also relates to learning about and using information about relationships between multiple cues in environment. Spatial learning in animals can be tested by allowing animals to learn locations of rewards and to use spatial cues for remembering the locations. For example, spatial learning can be tested using a radial arm maze (i.e., learning which arm has food) a Morris water maze (i.e., learning where the platform is). To perform these tasks, animals use cues from test room (positions of objects, odors, etc.). In human, spatial learning can also be tested. For example, a subject can be asked to draw a picture, and then the picture is taken away. The subject is then asked to draw the same picture from memory. The latter picture drawn by the subject reflects a degree of spatial learning in the subject.

The term "subject" refers to any mammal, in particular human, at any stage of life. For example, the subject can refer to an embryo, a fetus, a baby, a child, an adolescent or an adult.

A "normal" subject or a subject having "normal mental capacity" refers to a subject whose intellectual functioning level is around or above average (e.g., having an IQ above 75). A "normal" subject can also refer to a subject, such as a fetus, who does not appear to have any mental impairment (e.g., according to an amniocentesis test) and/or has no risk factors (e.g., family history of mental retardation or a mother who consumed alcohol in excessive amount during pregnancy to cause fetal alcohol syndrome in the fetus).

A subject is considered to have "mental retardation" based on the following three criteria: intellectual functioning level (IQ) is below 70-75; significant limitations exist in two or more adaptive skill areas; and the condition is present from childhood (defined as age 18 or less) (AAMR, 1992). Adaptive skill areas are those daily living skills needed to live, work and play in the community. They include communication, self-care, home living, social skills, leisure, health and safety, self-direction, functional academics (reading, writing, basic math), community use and work.

The term "Down's syndrome" is a chromosome disorder and occurs when, instead of the normal complement of 2 copies of chromosome 21, there is a whole, or sometimes part of an additional chromosome 21.

The term "contacting" is used herein interchangeably with the following: combined with, added to, mixed with, passed over, incubated with, flowed over, etc. Moreover, the ADNF I complex polypeptides of the present invention can be "administered" by any conventional method such as, for example, parenteral, oral, topical, and inhalation routes. In certain embodiments, oral administration is employed. In the context of methods related to fetal alcohol syndrome, or enhanced learning and memory via pre-natal treatment, ADNF I complex polypeptides can be administered directly to an embryo, a fetus, or a subject in utero or to the subject in utero indirectly, by administering the polypeptide to the mother by any other methods described herein.

"An amount sufficient" or "an effective amount" is that amount of a given ADNF I complex polypeptide that reduces neuronal cell death or reduces a condition, such as neuronal cell death, fetal alcohol syndrome or oxidative stress as described herein, or enhances learning and memory, as described herein. For example, in the context of neuronal death, "an amount sufficient" or "an effective amount" is that amount of a given ADNF I complex polypeptide that reduces neuronal cell death in the assays of, e.g., Hill et al., *Brain Res.* 603:222-233 (1993); Brenneman et al., *Nature* 335:639-642 (1988); or Brenneman et al., *Dev. Brain Res.* 51:63-68 (1990); Forsythe & Westbrook, *J. Physiol. Lond.* 396:515-533 (1988). In the context of reducing oxidative stress, "an amount sufficient" or "an effective amount" is that amount of ADNF I complex polypeptide that reduces or prevents, e.g., changes in lipid peroxidation in plasma or changes in antioxidant system in accordance with the assays described in Schlorff et al., *Alcohol* 17:97-105 (1999). In the context of reducing fetal alcohol syndrome, "an amount sufficient" or "an effective amount" is that amount of a given ADNF I complex polypeptide that reduces or prevents, for example, (1) the percentage of fetus death, (2) a reduction in fetal weights and fetal brain weights, or (3) a reduction in the level of VIP mRNA in embryos. In the context of improving learning and memory, "an amount sufficient" or "an effective amount" is that amount of a given ADNF I complex polypeptide that reduces the latency in finding a platform in a water-maze test, either in the first daily test (indicative of reference memory) or in the second daily test (indicative of short term memory). The dosing range can vary depending on the ADNF I complex polypeptide used, the route of administration and the potency of the particular ADNF I complex polypeptide, but can readily be determined using the foregoing assays.

The dosing range can vary depending on the ADNF I complex polypeptide used, the route of administration and the potency of the particular ADNF I complex polypeptide, but can readily be determined using the foregoing assays.

The term "biologically active" refers to a peptide sequence that will interact with naturally occurring biological molecules to either activate or inhibit the function of those molecules in vitro or in vivo. The term "biologically active" is most commonly used herein to refer to ADNF I complex polypeptides or subsequences thereof that exhibit neuroprotective/neurotrophic action on neurons originating in the central nervous system either in vitro or in vivo. The neuroprotective/neurotrophic action of ADNF I complex polypeptides can be tested using, e.g., cerebral cortical cultures treated with a neurotoxin (see, Gozes et al., *Proc. Nat'l. Acad. Sci. USA* 93:427-432 (1996)).

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF I complex nucleic acid encoding an ADNF I complex polypeptide is separated from open reading frames that flank the ADNF I complex gene(s) and encode proteins other than ADNF I complex polypeptide. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The term "amino acid" refers to naturally occurring amino acids in L-form and their enantiomers in D-form, amino acid analogs, and amino acid mimetics. The two-mirror-image forms (enantiomers) of amino acids are called the L-isomer and the D-isomer, where L refers to levorotatory (left rotation of the plane of polarization of light) and D refers to dextrorotatory (right rotation of the plane of polarization). The term "amino acid" also includes amino acids that are later modified, e.g., hydroxyproline, γ-carboxyglutatmate, and O-phosphoserine. Amino acid analogs refer to synthetic amino acids that have the same basic chemical structure as naturally occurring amino acids in L-form or their enantiomers in D-form, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acid analogs and amino acids mimetics can also be in L-form or in D-form.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).

(see, e.g., Creighton, *Proteins* (1984)).

The terms "polypeptide," "peptide," and "protein" are used interchangeably herein to refer to a polymer of amino acid residues. The terms apply to amino acid polymers in which one or more amino acid residue is a naturally occurring amino acid in L-form or their enantiomers in D-form, an analog or mimetic of amino acids in L-form or D-form, or combinations thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., *supra*). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of an ADNF I complex polypeptide.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to an ADNF I complex polypeptide, polymorphic variants, alleles, orthologs, and conservatively modified variants, or splice variants, or portions thereof, can be selected to obtain only those polyclonal antibodies that are specifically immunoreactive with ADNF I complex polypeptide and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

ADNF I Complex Polypeptides

Any suitable ADNF I complex polypeptide can be administered in embodiments of the invention. For example, the polypeptide can be an ADNF I complex polypeptide or a mixture thereof. In some embodiments, ADNF I complex polypeptides may comprise all L-amino acids, all D-amino acids, or a combination thereof. When ADNF I complex polypeptides are to be orally administered, preferably an ADNF I complex polypeptide comprises at least one D-amino acid within its active core site, more preferably at the N-terminus and/or the C-terminus of the active core site, and even more preferably at the entire active core site or over the length of the molecule. Alternatively, the D-amino acid can be at any suitable position in the polypeptide sequence. Since D-enatiomers of polypeptides are enzymatically more stable than their L-enatiomers, particularly in the gastrointestinal tract, an ADNF I complex polypeptide comprising D-amino acids are particularly useful for oral administration.

ADNF I complex polypeptides can be synthesized using both recombinant DNA methods, as well as being isolated from naturally occurring sources, or synthesized using chemical methods, as known to those of skill in the art and as described herein. Expression vectors containing a nucleic acid encoding an ADNF I complex polypeptide can be introduced into host cells, and then the expressed ADNF I complex polypeptide can be purified.

Moreover, one of skill will recognize that other modifications can also be made to the ADNF I complex polypeptides without diminishing their biological activity. For example, modifications can be made to avoid cleavage by enzymes in the stomach or intestines. In another example, modifications can be made to aid the purification process.

It will be readily apparent to those of ordinary skill in the art that the biologically active ADNF I complex polypeptides of the present invention can readily be screened for neuroprotective/neurotrophic activity using a number of methods known in the art. For example, a cerebral cortical cell culture assay can be used. In cerebral cortical cell culture assays, cerebral cortical cell cultures are prepared using the techniques described by Forsythe & Westbrook, *J. Physiol. Lond.* 396:515-533 (1988) with the following modifications. Cerebral cortex are used instead of hippocampus, and newborn rats are used instead of E16 mice. After nine days growth in vitro, the cultures are given a complete change of medium and treated with the ADNF I complex polypeptide of interest (dissolved in phosphate buffered saline) for an additional five days. To terminate, the cells are fixed for immunocytochemistry and neurons identified with antibodies against NSE (i.e., neuron specific enolase, a neuronal specific marker). Cell counts are performed on 30 fields, with total area of about 15 $mm^2$. Neurons are counted without knowledge of treatment. Control counts not treated with any drugs should run for purposes of comparison. Furthermore, assays described by, e.g., Hill et al., *Brain Res.* 603:222-233 (1993).

Using these assays, one of ordinary skill in the art can readily prepare a large number of ADNF I complex polypeptides in accordance with the teachings of the present invention and, in turn, screen them using the foregoing assay to find ADNF I complex polypeptides, in addition to those set forth herein, which possess neuroprotective/neurotrophic activity.

Chemical Synthesis of ADNF I Complex Polypeptides

ADNF I complex polypeptides, including ADNF I complex polypeptides comprising at least one D-amino acid, can be prepared via a wide variety of well-known chemical synthesis techniques. Polypeptides are typically synthesized in solution or on a solid support in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Using solid phase synthesis methods, one or more D-amino acids can be inserted, instead of L-amino acids, into an ADNF I complex polypeptide at any desired location(s). Techniques for solid phase synthesis are described by Barany & Merrifield, *Solid-Phase Peptide Synthesis*; pp. 3-284 in *The Peptides: Analysis, Synthesis, Biology*. Vol. 2: *Special Methods in Peptide Synthesis, Part A.*; Merrifield et al., *J. Am. Chem. Soc.* 85:2149-2156 (1963); and Stewart et al., *Solid Phase Peptide Synthesis* (2nd ed. 1984).

After chemical synthesis, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body polypeptides in guanidine-DTE. The polypeptide is then refolded in a redox buffer containing oxidized glutathione and L-arginine.

Isolation of Nucleic Acids Encoding ADNF I Complex Polypeptides

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

ADNF I complex polypeptides, nucleic acids, polymorphic variants, orthologs, and alleles that are substantially identical to an amino acid sequence of an ADNF I complex polypeptide can be isolated using ADNF I complex polypeptide nucleic acid probes and oligonucleotides under stringent hybridization conditions, by screening libraries. Alternatively, expression libraries can be used to clone ADNF I complex polypeptides, polymorphic variants, orthologs, and alleles by detecting expressed homologs immunologically with antisera or purified antibodies made against human ADNF I complex polypeptides or portions thereof.

To make a cDNA library, one should choose a source that is rich in ADNF I complex polypeptide-encoding RNA, such as astrocytes, neuroblastomas, or fibroblasts. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating ADNF I complex nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences encoding human ADNF I complex polypeptides directly from mRNA, from cDNA, from genomic libraries or cDNA libraries. Degenerate oligonucleotides can be designed to amplify ADNF I complex nucleic acids and homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ADNF I complex polypeptide-encoding mRNA in physiological samples, for nucleic acid sequencing, or for other purposes. Genes amplified by the PCR reaction can be purified from agarose gels and cloned into an appropriate vector.

Gene expression of ADNF I complex polypeptides can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding ADNF I complex polypeptides can be used with high density oligonucleotide array technology (e.g., GeneChip™) to identify ADNF I complex polypeptides, orthologs, alleles, conservatively modified variants, and polymorphic variants in this invention. In the case where the homologs being identified are linked to modulation of T cell activation, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene for ADNF I complex polypeptides is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding ADNF I complex polypeptides, one typically subclones ADNF I complex nucleic acids into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the ADNF I complex polypeptides are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the ADNF I complex polypeptide-encoding nucleic acid in host cells. A typical expression cassette thus contains a promoter operably linked to the nucleic acid sequence encoding ADNF I complex polypeptides and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, $\beta$-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a ADNP I complex polypeptide-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of ADNF I complex polypeptide, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing ADNF I complex polypeptides.

After the expression vector is introduced into the cells, the transfected cells are cultured under conditions favoring expression of ADNF I complex polypeptides, which is recovered from the culture using standard techniques identified below.

Purification of ADNF 1 Complex Polypeptides

Either naturally occurring or recombinant ADNF I complex polypeptides can be purified for use in functional assays, as well as chemically synthesized ADNF I complex polypeptides. Naturally occurring ADNF I complex polypeptides can be purified, e.g., from human tissue. Recombinant ADNF I complex polypeptides can be purified from any suitable expression system.

The ADNF I complex polypeptide may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant ADNF I complex polypeptide is being purified. For example, proteins having established molecular adhesion properties can be reversible fused to the ADNF I complex polypeptide. With the appropriate ligand, ADNF I complex polypeptide can be selectively adsorbed to a purification column and then freed from the column in a relatively pure form. The fused protein is then removed by enzymatic activity. Finally, ADNF I complex polypeptide could be purified using immunoaffinity columns.

A. Purification of ADNF I Complex Polypeptides from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of ADNF I complex polypeptide inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF.

The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human ADNF I complex polypeptides are separated from other bacterial proteins by standard separation techniques, e.g., with Ni-NTA agarose resin.

Alternatively, it is possible to purify ADNF I complex polypeptides from bacteria periplasm. After lysis of the bacteria, when the ADNF I complex polypeptide is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying ADNF I Complex Polypeptides Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the ADNF I complex polypeptides can be used to isolate them from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatograhy

The ADNF I complex polypeptides can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Pharmaceutical Compositions and Administration

ADNF I complex polypeptides and nucleic acids encoding ADNF I complex polypeptides can be pre-naturally or postnatally administered to the subject using any suitable methods known in the art. For example, ADNF I complex polypeptides or nucleic acids can be formulated as pharmaceutical compositions with a pharmaceutically acceptable diluent, carrier or excipient. Suitable formulations for use in the present invention are found in *Remington's Pharmaceutical Sciences* (17th ed. 1985)), which is incorporated herein by reference. A brief review of methods for drug delivery is also described in, e.g., Langer, *Science* 249:1527-1533 (1990), which is incorporated herein by reference. In addition, the pharmaceutical compositions comprising peptides and proteins are described in, e.g., *Therapeutic Peptides and Proteins Formulations, Processing, and Delivery Systems*, by Banga, Technomic Publishing Company, Inc., Lancaster, Pa. (1995).

In one embodiment, ADNF I complex polypeptides are formulated for oral or nasal administration, e.g., to the subject, or for prenatal administration, to the subject's mother. In this embodiment, it is preferred that ADNF I complex polypeptides comprising one or more D-amino acids are used. A pharmaceutically acceptable nontoxic composition is formed by incorporating any of normally employed excipients, and generally 10-95% of active ingredient and more preferably at a concentration of 25%-75%. Furthermore, to improve oral or nasal absorption of ADNF I complex polypeptides, various carrier systems, such as nanoparticles, microparticles, liposomes, phospholipids, emulsions, erythrocytes, etc. can be used. The oral or nasal agents comprising ADNF I complex polypeptides of the invention can be in any suitable form for oral or nasal administration, such as liquid, tablets, capsules, or the like. The oral or nasal formulations can be further coated or treated to prevent or reduce dissolution in stomach. See, e.g., *Therapeutic Peptides and Proteins, Formulation, Processing, and Delivery Systems*, by A. K Banga, Technomic Publishing Company, Inc., 1995.

Furthermore, the ADNF I complex polypeptides can be formulated for parenteral, topical, nasal, sublingual, gavage, or local administration. For example, the pharmaceutical compositions are administered parenterally, e.g., intravenously, subcutaneously, intradermally, or intramuscularly, or intranasally. Thus, the invention provides compositions for parenteral administration that comprise a solution of a mixture of ADNF I complex polypeptides, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques, or they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc. In one embodiment, a nucleic acid encoding an ADNF I complex polypeptide is administered as a naked DNA.

For aerosol administration, ADNF I complex polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

For solid compositions, conventional nontoxic solid carriers may be used. Solid carriers include, for example, pharmaceutical grades of mannitol, lactose, starch, magnesium stearate, sodium saccharin, talcum, cellulose, glucose, sucrose, magnesium carbonate, and the like.

The present invention also provides for therapeutic compositions or medicaments comprising a mixture of one or more of the ADNF I complex polypeptides described herein above in mixture with a pharmaceutically acceptable excipient, wherein the amount of a mixture the ADNF I complex polypeptides is sufficient to provide a desirable therapeutic effect.

Small polypeptides such as ADNF I complex polypeptides cross the blood brain barrier. For longer polypeptides that do not the cross blood brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62-64 (1981); Peterson et al., *Biochem. Pharamacol.* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)). In particular, cannulas can be used to administer neurotrophic factors to mammals (see, e.g., Motta & Martini, *Proc. Soc. Exp. Biol. Med.* 168:62-64 (1981) (neurotensin); Peng et al, *Brain Res.* 632:57-67 (1993) (NGF); Anderson et al., *J. Comp. Neurol.* 357:296-317 (1995) (BDNF, NGF, neurotrophin-3).

Alternatively, longer ADNF I complex polypeptides that do not cross blood brain barrier can be coupled with a material which assists the ADNF I complex polypeptides to cross the blood brain barrier and to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ADNF I complex polypeptides across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the hydrophobic domain of signal peptides, was found to have similar cell membrane translocation characteristics (see, e.g., Lin et al., *J. Biol. Chem.* 270:1 4255-14258 (1995)).

Examples of peptide sequences which can be linked to a ADNF I complex polypeptides of the invention, for facilitating uptake of ADNF I complex polypeptides s into cells, include, but are not limited to: an 11 amino acid peptide of the that protein of HIV (see Schwarze et al., *Science* 285:1569-1572 (1999)); a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ADNF I complex polypeptides.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *Proc. Nat'l Acad. Sci. USA* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *Proc. Nat'l Acad. Sci. USA* 89:10277-10281 (1992); and Novak et al., *J. Biol. Chem.* 267:17186-17193 1992)).

Such subsequences can be used to translocate ADNF I complex polypeptides across a cell membrane. ADNF I complex polypeptides can be conveniently fused to or derivatized with such sequences. Typically, the translocation sequence is provided as part of a fusion protein. Optionally, a linker can be used to link the ADNF I complex polypeptides and the translocation sequence. Any suitable linker can be used, e.g., a peptide linker.

The ADNF I complex polypeptides and nucleic acids encoding ADNF I complex polypeptides can also be introduced into an animal cell, preferably a mammalian cell, via a liposomes and liposome derivatives such as immunoliposomes and lipid:nucleic acid complexes. The term "liposome" refers to vesicles comprised of one or more concentrically ordered lipid bilayers, which encapsulate an aqueous phase. The aqueous phase typically contains the compound to be delivered to the cell, i.e., an ADNF I complex polypeptide.

The liposome fuses with the plasma membrane, thereby releasing the ADNF I complex polypeptides into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, an ADNF I complex polypeptide) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *Proc. Nat'l Acad. Sci. USA* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise an ADNF I complex polypeptide and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, *Biochim. Biophys. Acta* 443:629-634 (1976); Fraley, et al., *Proc. Nat'l Acad. Sci. USA* 76:3348-3352 (1979); Hope et al., *Biochim. Biophys. Acta* 812:55-65 (1985); Mayer et al., *Biochim. Biophys. Acta* 858:161-168 (1986); Williams et al., *Proc. Nat'l Acad. Sci. USA* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044). Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337-16342 (1990) and Leonetti et al., *Proc. Nat'l Acad. Sci. USA* 87:2448-2451 (1990).

Alternatively, nucleic acids encoding an ADNF I complex polypeptide can also be used to provide a therapeutic dose of an ADNF I complex polypeptide. These nucleic acids can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™. Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

In therapeutic applications, ADNF I complex polypeptides of the invention are administered to a patient (either pre- or post-natally) in an amount sufficient to reduce neuronal cell death associated with various disorders, to reduce oxidative stress in a patient, to reduce a condition associated with fetal alcohol syndrome in a subject in utero, or to improve a subject's performance (e.g., learning and/or memory). An amount adequate to accomplish this is defined as "therapeutically effective dose." Amounts effective for this use will depend on, for example, the particular ADNF I complex polypeptide employed, the manner of administration, the weight and general state of health of the patient, and the judgment of the prescribing physician. For example, an amount of ADNF I complex polypeptide falling within the range of a 1 µg to 50 µg, preferably 1 µg to 10 µg dose given intranasally or orally once a day per mouse (e.g., in the evening) would be a therapeutically effective amount. This dose is based on the average body weight of a mouse. Therefore, an appropriate dose can be extrapolated for a human body.

For pre-natal administration, ADNF I complex polypeptides can be pre-natally administered to the subject directly or indirectly through the subject's mother. ADNF I complex polypeptides can be administered at any time during the pregnancy. Preferably, ADNF I complex polypeptides are administered to the subject during the first trimester (i.e., first 12 weeks) of the pregnancy when organs and the nervous system of the subject are actively developing. More preferably, ADNF I complex polypeptides are administered during the time of neural tube development (which begins around 22 days post-conception) and prior to its closure. ADNF I complex polypeptides can be administered as a single dose, preferably during the critical period of neural tube development, or can be administered as multiple doses throughout the pregnancy.

Methods for Reducing Neuronal Cell Death

In another aspect, the present invention provides a method for reducing neuronal cell death, the method comprising contacting neuronal cells with an ADNF I complex polypeptide in an amount sufficient to reduce neuronal cell death. In one embodiment, the an ADNF I complex polypeptide comprises at least one D-amino acid, preferably at the N-terminus and/or the C-terminus.

ADNF I complex polypeptides of the present invention can be used in the treatment of neurological disorders and for the prevention of neuronal cell death. For example, an ADNF I complex polypeptide of the present invention can be used to prevent the death of neuronal cells including, but not limited to, spinal cord neurons, hippocampal neurons, cerebral cortical neurons and cholinergic neurons. More particularly, ADNF I complex polypeptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease.

As such, the ADNF I complex polypeptides of the present invention can be used to reduce gp120-induced neuronal cell death by administering an effective amount of an ADNF I complex polypeptide of the present invention to a patient infected with the HIV virus. The ADNF I complex polypeptides of the present invention can also be used to reduce neuronal cell death associated with excito-toxicity induced by N-methyl-D-aspartate stimulation, the method comprising contacting neuronal cells with an ADNF I complex polypeptide of the present invention in an amount sufficient to prevent neuronal cell death. The ADNF I complex polypeptides of the present invention can also be used to reduce cell death induced by the β-amyloid peptide in a patient afflicted or impaired with Alzheimer's disease, the method comprising administering to the patient an ADNF I complex polypeptide of the present invention in an amount sufficient to prevent neuronal cell death. The ADNF I complex polypeptides can also be used to alleviate learning impairment produced by cholinergic blockage in a patient afflicted or impaired with Alzheimer's disease. For example, ADNF I complex polypeptides can be used to improve short-term and/or reference memory in Alzheimer's patients.

Similarly, it will be readily apparent to those of skill in the art that the ADNF I complex polypeptides of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

ADNF I complex polypeptides (including their alleles, polymorphic variants, species homologs and subsequences thereof) that reduce neuronal cell death can be screened using the various methods described in U.S.S.N. 60/037,404, filed Feb. 7, 1997 (published as WO98/35042), and U.S.S.N. 09/187,330 filed Nov. 6, 1998, now U.S. Pat. No. 6,613,740, both of which are incorporated herein by reference. For example, it will be readily apparent to those skilled in the art that using the teachings set forth above with respect to the design and synthesis of ADNF I complex polypeptides and the assays described herein, one of ordinary skill in the art can identify other biologically active ADNF I complex polypeptides. For example, Brenneman et al., Nature 335:639-642 (1988), and Dibbern et al., J. Clin. Invest. 99:2837-2841 (1997), incorporated herein by reference, teach assays that can be used to screen ADNF I complex polypeptides that are capable of reducing neuronal cell death associated with envelope protein (gp120) from HIV. Also, Brenneman et al., Dev. Brain Res. 51:63-68 (1990), and Brenneman & Gozes, J. Clin. Invest. 97:2299-2307 (1996), incorporated herein by reference, teach assays that can be used to screen ADNF I complex polypeptides which are capable of reducing neuronal cell death associated with excito-toxicity induced by stimulation by N-methyl-D-aspartate. Other assays described in, e.g., WO98/35042 can also be used to identify other biologically active ADNF I complex polypeptides, optionally comprising at least one D-amino acid.

Moreover, ADNF I complex polypeptides that reduce neuronal cell death can be screened in vivo. For example, the ability of ADNF I complex polypeptides that can protect against learning and memory deficiencies associated with cholinergic blockade can be tested. For example, cholinergic blockade can be obtained in rats by administration of the cholinotoxin AF64A, and ADNF I complex polypeptides can be administered intranasally and the water maze experiments can be performed (Gozes et al., *Proc. Natl. Acad. Sci. USA* 93:427-432 (1996), the teachings of which are incorporated herein by reference). Animals treated with efficacious ADNF I complex polypeptides would show improvement in their learning and memory capacities compared to the control.

Furthermore, the ability of ADNF I complex polypeptides that can protect or reduce neuronal cell death associated with Alzheimer's disease can be screened in vivo. For these experiments, apolipoprotein E (ApoE)-deficient homozygous mice can be used (Plump et al., *Cell* 71:343-353 (1992); Gordon et al., *Neuroscience Letters* 199:1-4 (1995); Gozes et al., *J. Neurobiol.* 33:329-342 (1997)), the teachings of which are incorporated herein by reference.

Methods for Reducing Oxidative Stress

In yet another aspect, the present invention provides methods for treating oxidative stress in a patient by administering to the patient an ADNF I complex polypeptide in an amount sufficient to prevent or reduce oxidative stress, wherein the ADNF I complex polypeptide optionally comprises at least one D-amino acid, preferably at the N-terminus and/or the C-terminus. Oxidative stress has been implicated in several neurodegenerative diseases in humans (Cassarmno & Bennett, *Brain Res. Reviews* 29:1-25 (1999)). Moreover, oxidative stress produced from alcohol administration has been associated with fetal death and abnormalities (e.g., conditions associated with fetal alcohol syndrome). See, e.g., Henderson et al., *Alcoholism: Clinical and Experimental Research* 19:714-720 (1995). By using the ADNF I complex polypeptides of the present invention, oxidative stress associated with various clinical conditions can be reduced.

ADNF I complex polypeptides (including their alleles, polymorphic variants, species homologs and subsequences thereof) that are effective in reducing oxidative stress can be screened using primary neurons. For example, cultured embryonic neurons (E18) rat hippocampal neurons can be treated with, e.g., 0.5 µM $FeSO_4$ to induce oxidative stress. The degree of oxidative stress can be quantified by cell counting and/or morphological criteria. Furthermore, apoptosis induced by oxidative stress results in nuclear condensation and DNA fragmentation. Apoptotic nuclei can be measured by counting cells in culture stained with the fluorescent DNA-binding dye, e.g., Hoescht 33342. See Glazner et al., *Society for Neuroscience 27th Annual Meeting*, Abstracts vol. 23, part 2 (1997). To screen ADNF I complex polypeptides that can reduce oxidative stress in vitro, $FeSO_4$ treated neurons can be contacted with various ADNF I complex polypeptides for sufficient time (e.g., 24 hours). Cells with apoptotic nuclei can be quantified as described above. ADNF I complex polypeptides that reduce the quantity of apoptotic nucleic compared to control (e.g., cells untreated with ADNF I complex polypeptides) can be used to treat oxidative stress in a patient.

ADNF I complex polypeptides that are effective in reducing oxidative stress can also be screened using in vivo assays. For example, ethanol consumption is known to cause oxidative stress in vivo. In the human body, ethanol is metabolized into cytotoxic acetaldehyde by alcohol dehydrogenase enzyme in the liver and acetaldehyde is oxidized to acetate by aldehyde oxidase or xanthine oxidase giving rise to free radicals or reactive oxygen species (ROS). See, e.g., Schlorff et al., *Alcohol* 17:95-105 (1999). Thus, ethanol consumption can be used to induce oxidative stress in in vivo animal models (e.g., rat, mouse, human, etc.). Thereafter, animals suffering from ethanol induced oxidative stress can be used as models to screen ADNF I complex polypeptides that can reduce the level of oxidative stress.

The level of oxidative stress of cells and tissues of in vivo animal models can be measured using a number of assays known in the art. For example, protocols described in Schlorff et al. (1999), supra, can be used to measure effects of rat ethanol ingestion on lipid peroxidation in plasma (e.g., plasma malondialdehyde) and changes in antioxidant system (e.g., superoxide dismutase, catalase, glutathione peroxidase, glutathione reductase, etc.). Effective ADNF I complex polypeptides are those that prevent or reduce changes in lipid peroxidation in plasma or on antioxidant system in ethanol ingested animal models compared to control (e.g., animal models untreated with ADNF I complex polypeptides). In another example, fetal death and abnormalities (e.g., conditions associated with fetal alcohol syndrome) are considered a severe form of oxidative stress produced from alcohol administration (Henderson et al., *Alcoholism: Clinical and Experimental Research* 19:714-720 (1995)). Therefore, a well established model (e.g., mice) for fetal alcohol syndrome can also be used to screen for ADNF I complex polypeptides that can reduce oxidative stress.

Methods for Reducing a Condition Associated with Fetal Alcohol Syndrome

In yet another aspect, the present invention provides a method for reducing a condition associated with fetal alcohol syndrome in a subject who is exposed to alcohol in utero, the method comprising administering to the subject an ADNF I complex polypeptide in an amount sufficient to reduce the condition associated with fetal alcohol syndrome, wherein the ADNF I complex polypeptide optionally comprises at least one D-amino acid, preferably at the N-terminus and/or the C-terminus.

Treatment of a well-characterized model for FAS (e.g., C57B1/6J mouse strain) with an ADNF I complex polypeptide reduces or prevents alcohol induced fetus death, body and brain weight reduction, and VIP mRNA reduction. Similarly, the human embryo, fetus, or subject can be protected from alcohol induced effects by administering an ADNF I complex polypeptide directly to the embryo, fetus, or subject, or by administering the ADNF I complex polypeptide indirectly to the fetus by administering it to the mother. Preferably, ADNF I complex polypeptides are orally administered.

ADNF I complex polypeptides (including their alleles, polymorphic variants, species homologs and subsequences thereof) that reduce a condition associated with fetal alcohol syndrome can be screened using a well-characterized animal model for FAS. For example, the C57B1/6J mouse strain can be used. Previous work with this strain has defined the effects of dosage and embryonic timing on maternal serum alcohol levels and embryonic effects (Webster et al., *Neurobehav. Tox.*, 2:227-34 (1980), incorporated herein by reference). Intra-peritoneal treatment allows for defined and reproducible dosages. Acute (single) dosages of alcohol can reproduce the phenotype of FAS (Webster et al, (1980), supra). Since treatment on E8 results in the highest rate of fetal anomalies and demises, and vasoactive intestinal peptide's growth regulating effects on the embryo are limited to the early post-implantation period of embryogenesis, E8 can be chosen as a test for screening neuroprotective ADNF I complex polypeptides. The mice can be injected with 25% ethyl alcohol in saline (v/v) or vehicle alone at, e.g., 0.030 ml/g maternal body weight at, e.g., 9:00 a.m. on E8 (embryonic gestation day 8). Effective ADNF I complex polypeptides can be screened by pretreating the mice 30 minutes prior to alcohol administration. In one embodiment, the dose for nasal administration for an ADNF I complex polypeptide is about 1 µg-50 µg, preferably about 1 µg-10 µg/mouse. This dose is based on the average body weight of mice, and an appropriate dose for human can be extrapolated based on the average body weight of human.

Various parameters can be measured to determine if an ADNF I complex polypeptide reduces a condition associated with fetal alcohol syndrome. For example, a number of fetal demises (i.e., death) can be compared between the control (e.g., untreated with ADNF I complex polypeptides) and a group treated with ADNF I complex polypeptides. In another example, the fetal weight and fetal brain weight in the surviving E18 fetuses can be compared. In another example, the level of VIP mRNA can be compared between the control and a group treated with ADNF I complex polypeptides. In another example, the degree of learning deficits can be compared between the control and a group treated with ADNF I complex polypeptides. In another example, the glutathione level in the control and the treated group can be compared.

Methods for Enhancing Learning and Memory

In yet another aspect, the present invention provides a method of enhancing learning and memory, the method comprising administering either pre- or post-natally to the subject an ADNF I complex polypeptide in an amount sufficient to enhance learning and memory, wherein the ADNF I complex polypeptide optionally comprises at least one D-amino acid, preferably at the N-terminus and/or the C-terminus.

Various parameters can be measured to determine if ADNF I complex polypeptides improve performance (e.g., learning and memory) in vivo. For example, the hidden platform test of the Morris water maze, which is described in the example section below, can be used to test spatial learning and memory. Generally, mice that are treated with ADNF I complex polypeptides and control mice (that are not treated with ADNF I complex polypeptides) are trained to escape the swimming task by learning the position of a hidden platform and climbing on it. The time it takes them to complete this task is defined as the escape latency. This test can be conducted one or more times daily for a number of days. One parameter that is indicative of improved learning and memory is the reduction in latency in escaping the swimming task by climbing onto the hidden platform (see the example section below). See, also, methods described in Gozes et al., *Proc. Natl. Acad. Sci. USA* 93:427-432 (1996), incorporated herein by reference. Animals treated with suitable ADNF I complex polypeptides show improvement in their learning and memory capacities compared to the controls that are not treated with ADNF I complex polypeptides. Embodiments of the invention are not limited by examples of the test used to measure performance. Any suitable test methods can be used to measure performance, such as learning and memory.

Other methods known in the art can be used in human subjects to determine if an ADNF I complex polypeptide or a combination of ADNF I complex polypeptides improves performance (e.g., learning and memory) in vivo. For example, these methods include assessment of memory or learning over time by the Randt Memory Test (Randt et al., *Clin. Neuropsychol.*, 1980, 2:184), Wechsler Memory Scale (*J. Psych.* 19:87-95 (1945), Forward Digit Span test (Craik, Age Differences in Human Memory, in: *Handbook of the Psychology of Aging*, Birren, J., and Schaie, K. (Eds.), New York, Van Nostrand (1977), Mini-Mental State Exam (Folstein et al., *J. of Psych. Res.* 12:189-192 (1975), or California Verbal Learning Test (CVLT). See, also, U.S. Pat. No. 6,030,968. In these tests, factors unrelated to effects of ADNF I complex polypeptides (e.g., anxiety, fatigue, anger, depression, confusion, or vigor) are controlled for. See, U.S. Pat. No. 5,063,206. Methods for assessing and controlling for subjective factors is known in the art and determined by such standard clinical tests such as the BECK Depression Scale, Spielberger Trait State Anxiety test, and POMS test (Profile of Mood State).

Spatial learning can also be tested in human. For example, a subject can be asked to draw a picture, and then the picture is taken away. The subject is then asked to draw the same picture from memory. The latter picture drawn by the subject reflects a degree of spatial learning in the subject.

Various parameters can be measured to determine if ADNF I complex polypeptides improve learning and memory of a subject. For example, the degree of learning and memory improvement can be compared between the control (e.g., untreated with ADNF I complex polypeptides) and a group pretreated with ADNF I complex polypeptides. Learning and memory improvement can be assessed using, for example, a Morris water maze for rodents (see, e.g., the Example section) or any suitable tests such as those described above for humans.

If any one or more of these parameters are changed for the group treated with ADNF I complex polypeptides by, e.g., about 10%, optionally at least about 20%, at least about 30%, at least about 40%, at least about 50%, at least about 60%, at least about 70%, at least about 80%, at least about 90%, at least about 100%, at least about 150%, at least about 200%, etc., compared to control, then it can be said that the ADNF I complex polypeptides improved learning and memory of the subject. Alternatively, statistical analysis using ANOVA for continuous variables, Mann-Whitney U for nonparametic data, Chi square for categorical variables or Fisher's exact test with $p<0.05$ is considered significant.

EXAMPLES

The following examples are offered to illustrate, but not to limit the claimed invention.

Example I

Demonstration of Additional Subunits or Accessory Components of ADNF I Complex

Evidence is presented that purified ADNF I, when analyzed under acidic conditions or when treated with a protease inhibitor cocktail (see Example III), exhibited a complex dose response for survival-promoting activity that indicates the existence of labile and novel components that were not previously identified. These data are consistent with the existence of labile components of the ADNF I complex that are only apparent when a serine protease inhibitor is present or when the pH is lowered to 4.5.

ADNF I was isolated as previously described (see, e.g., Brenneman & Gozes, *J. Clin. Invest.* 97:2299-2307 (1996)) and then desalted and stored in 10 mM phosphate buffer (pH 4.5). The purified ADNF I was diluted 1:3 with water and analyzed on eCAP/SDS capillary electrophoresis (CE). The running and sample buffers for these analyses were components of the eCAP/SDS kit (Beckmann Instruments). Electrophoresis was conducted with 8.1 kV constant voltage and with reversed polarity. The capillary consisted of sodium dodecyl sulfate coating with a 100 µm inside diameter, 47 cm in length (300 V/cm). The pressure injection time was 70 sec at 80 psi.

Figure 2:
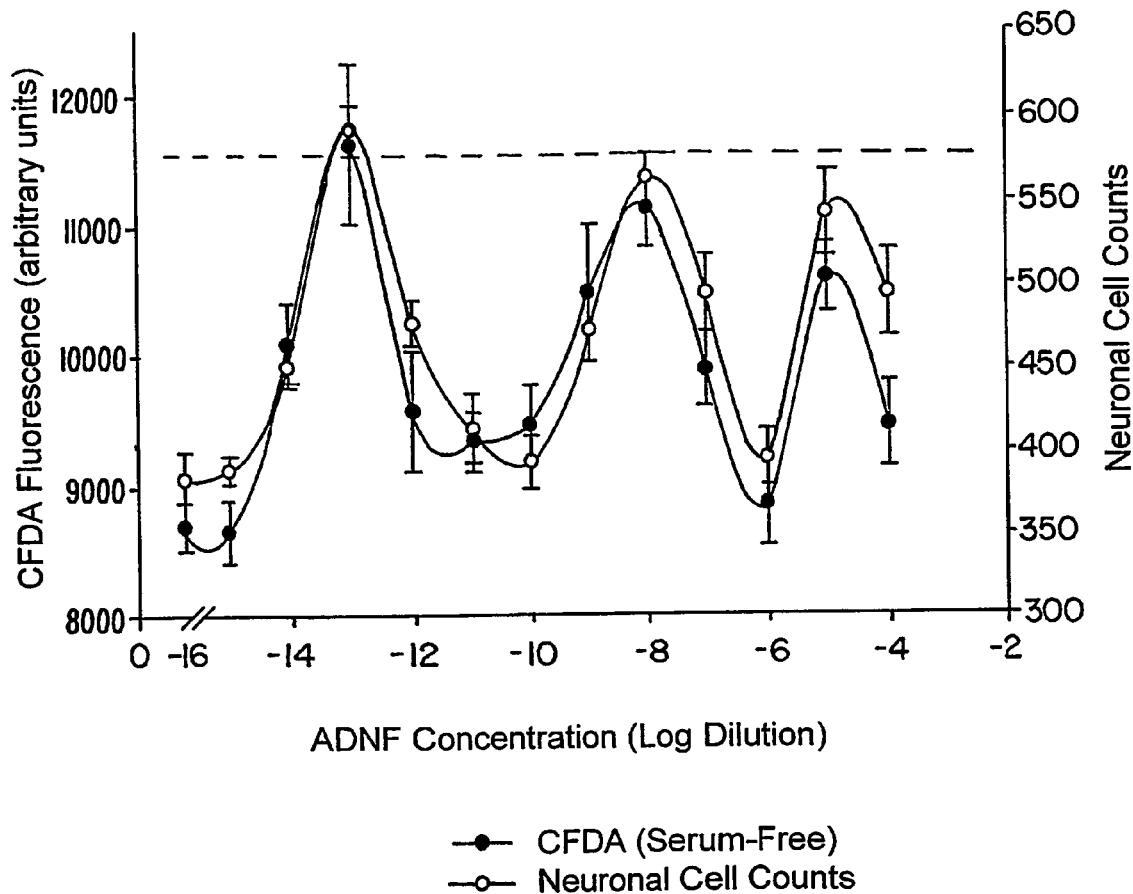
FIG. 2. Survival-promoting activity of 14 kDa peak isolated by eCAP/SDS capillary electrophoresis. ADNF I was purified by previously described chromatographic procedures (Brenneman et al., *J. Clin. Invest.* 97:2299-2304 (1996)). Salt was removed by multiple centrifugations with the microcon filtration units (0.22 μ) from Millipore Corp. The exchange buffer was 10 mM monobasic phosphate, pH 4.5). The ADNF preparation was then serially diluted in phosphate buffered saline and tested in dissociated cerebral cortical cultures from newborn rats. The culture conditions and treatment schedule employed has been previously described (Brenneman & Gozes, *J. Clin. Invest.* 97:2299-2304 (1996)) with one exception: cultures assessed with cell counts had 5% horse serum MEM/N3 growth medium during the treatment period, whereas cultures assessed with CFDA on serum-free, MEM/N3 growth medium. Cultures were treated with ADNF I and 1 μM tetrodotoxin after 3 days in vitro, and then assessed 5 days later by two methodologies: neuronal cell counts (shaded circles) and 5(6)-carboxyfluorescein diacetate (CFDA, closed circles), a marker for neuronal survival (Petroski & Geller, *J. Neurosci. Method.* 52:23-32 (1994)). Cell counts were performed as previously described (Brenneman & Gozes, *J. Clin. Invest.* 97:2299-2304 (1996)). The dotted horizontal line represents the cell counts for control cultures. The error bars are the standard error.

As shown in FIG. 1, this analysis revealed two peaks that were not present in the buffer/marker blank: peaks at approximately 14 and 60 kDa. The 14 kDa peak was isolated and concentrated with 5 consecutive collections, and then tested for survival-promoting activity in cerebral cortical cultures co-treated with 1 µM tetrodotoxin (see, e.g., Brenneman & Gozes, *J. Clin. Invest.* 97:2299-2307 (1996)). As shown in FIG. 2, the 14 kDa CE peak exhibited three peaks of activity as assessed by neuronal cell counts (see, e.g., Brenneman & Gozes, *J. Clin. Invest.* 97:2299-2307 (1996)) and by 5(6)-carboxyfluorescein diacetate (CFDA), a marker for neuronal survival (Petroski & Geller, *J. Neurosci. Method.* 52:23-32 (1994)).

Example II

Figure 3:
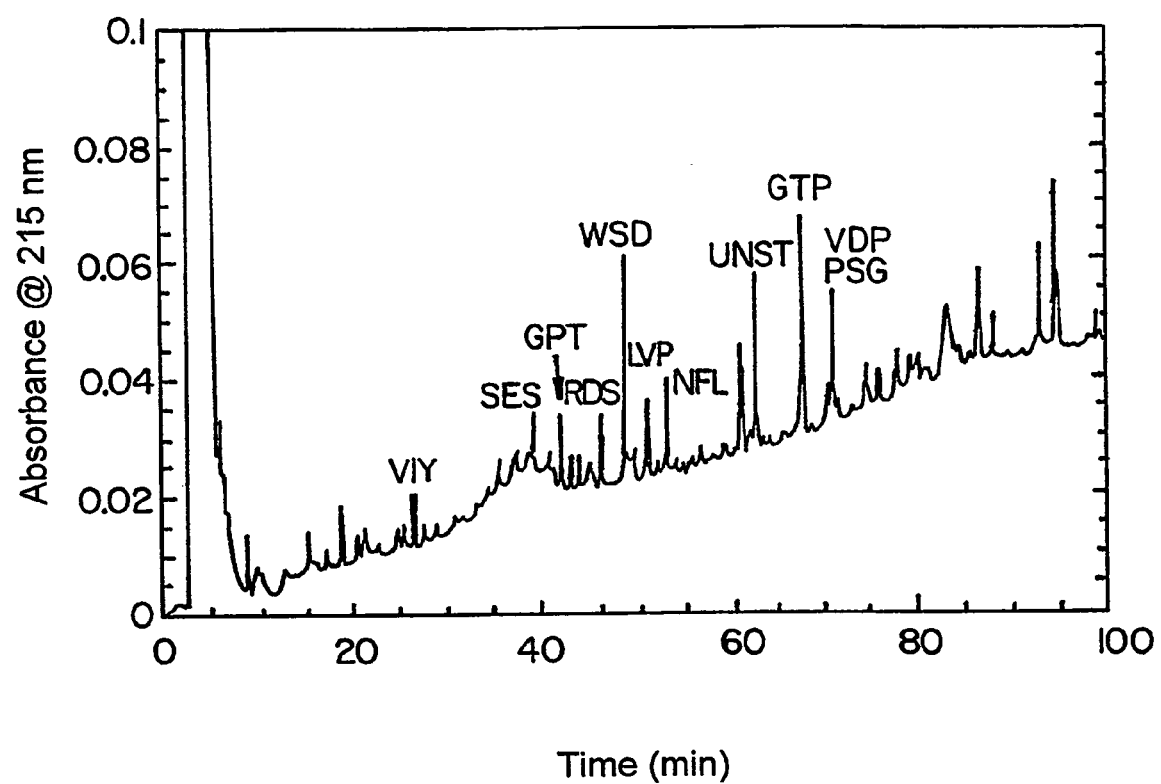
FIG. 3. Reverse phase high pressure liquid chromatography of ADNF I complex digest peptides. Gel band was subjected to proteolytic digestion with modified trypsin according to the method of Moritz et al. (Techniques in Protein Chemistry VI, pp 311-319, (1995)). Resulting digests were separated by RP-BPLC on a narrowbore (2.1×250 mm) Vyda 218TP52 column. The gradient described previously was employed (Fernandez et al., *Anal. Biochem.* 201:255-264 (1992)). Fractions were collected on a Biobrene-treated glass fiber filter and dried prior to amino acid sequencing. The letters above the peaks are abbreviations for the observed digest peaks.
Figure 4:
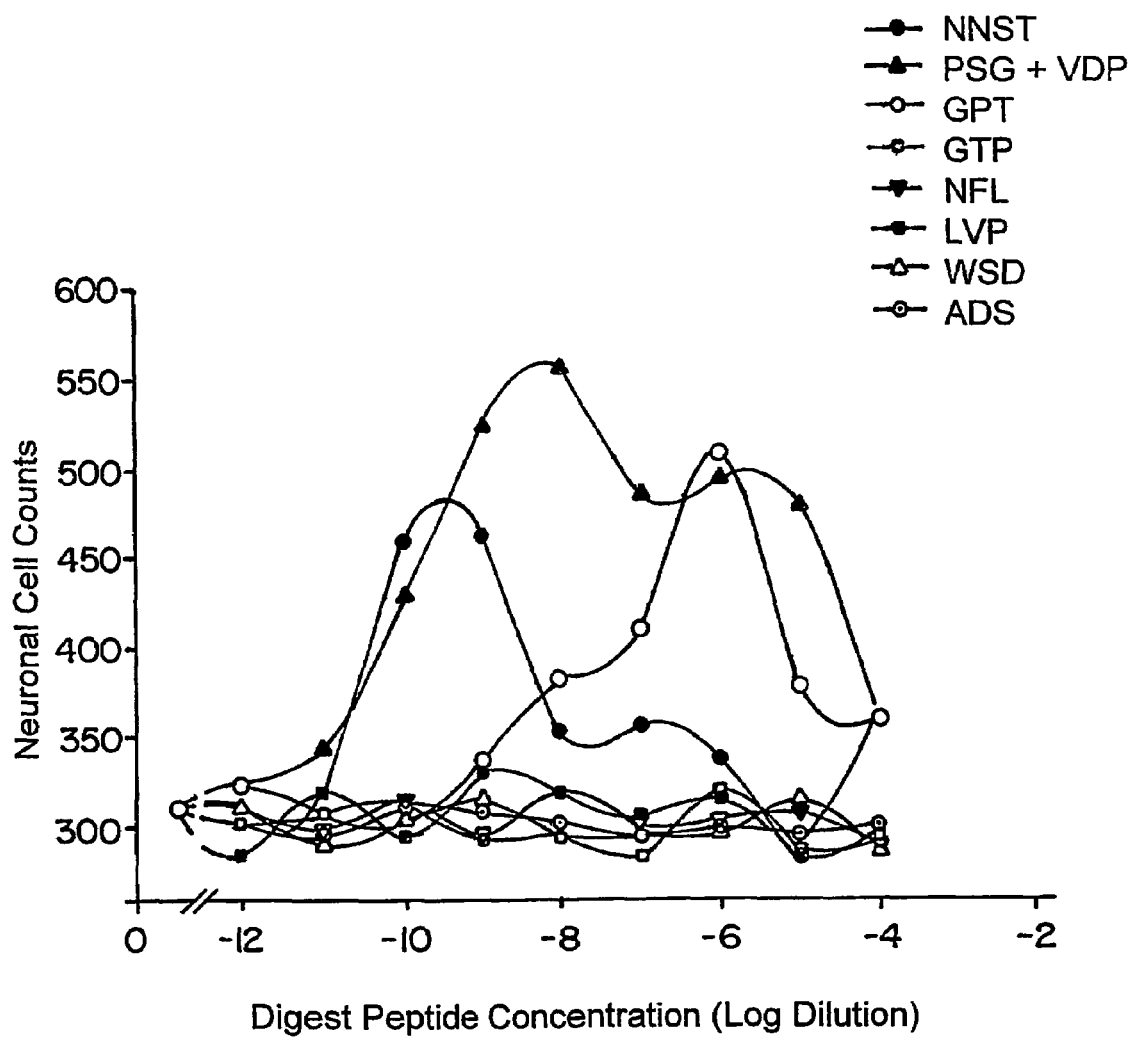
FIG. 4. Survival-promoting activity of peptide fractions from the ADNF I complex digestion. The peptide fractions from the reverse phase HPLC column described in FIG. 3 were tested in dissociated cerebral cortical cultures as described in FIG. 2. Peptide fractions were serially diluted in phosphate buffered saline. The test cultures were co-treated with 1 μM tetrodotoxin. Significant increases in neuronal cell counts were observed with the following peptides fractions: NNST, PSG+VDP, SES, and GPT.

Demonstration of Tryptic Digest Peptides from ADNF I Complex and their Neuroprotective Activity in CNS Cultures Digest peptides were obtained after treatment of purified ADNF I with trypsin as previously described (Williams & Stone, *Techniques in Protein Chemistry VI.* pp 79-90 (1997)). As shown in FIG. 3, the peptides were separated by reverse phase HPLC. The peptide identified for each of the peaks is given as the first three amino acids of the peptide. Aliquots of the isolated peptides were sequenced by Edman degradation or tested for survival-promoting activity in TTX-treated cerebral cortical cultures. As shown in FIG. 4, three digest peptide fractions exhibited survival-promoting activity in vitro. The active peptides were:

1. NNSTTYAPISANVSTALGSTAALPTAAGPV (retention time: 62 min) Abrev.: NNST

2. GPTADITLTK (retention time: 43 min) Abrev.: GPT

3. NPSGTDWLNTNNQANPFN (retention time: 71 min) Abrev. PSG

Figure 5:
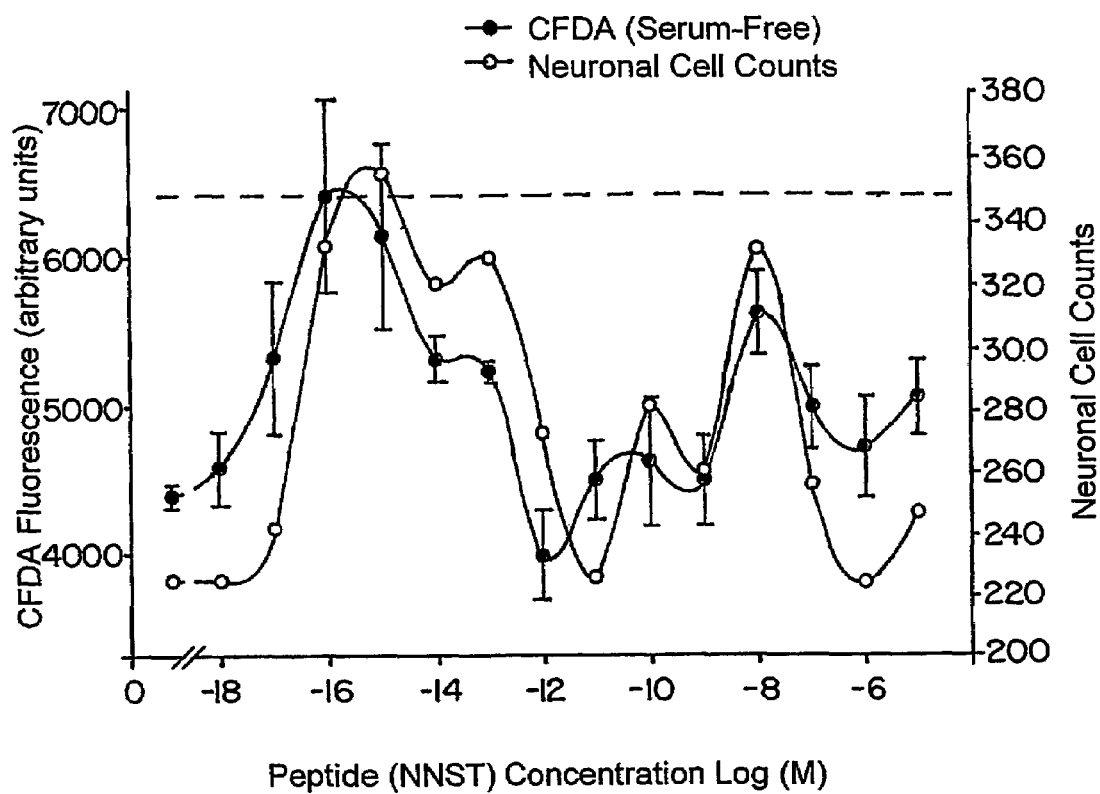
FIG. 5. Synthesized NNST peptide increases neuronal survival in TTX-treated cerebral cortical cultures. The peptide NNSTTYAPISANVSTALGSTALLPTAAGPV (NNST) was synthesized and treated as described in FIG. 2. Both neuronal cell counts and CFDA were used to assess neuronal survival. The dotted line represents the neuronal cell counts of control cultures. The error bar is the standard error.
Figure 6:
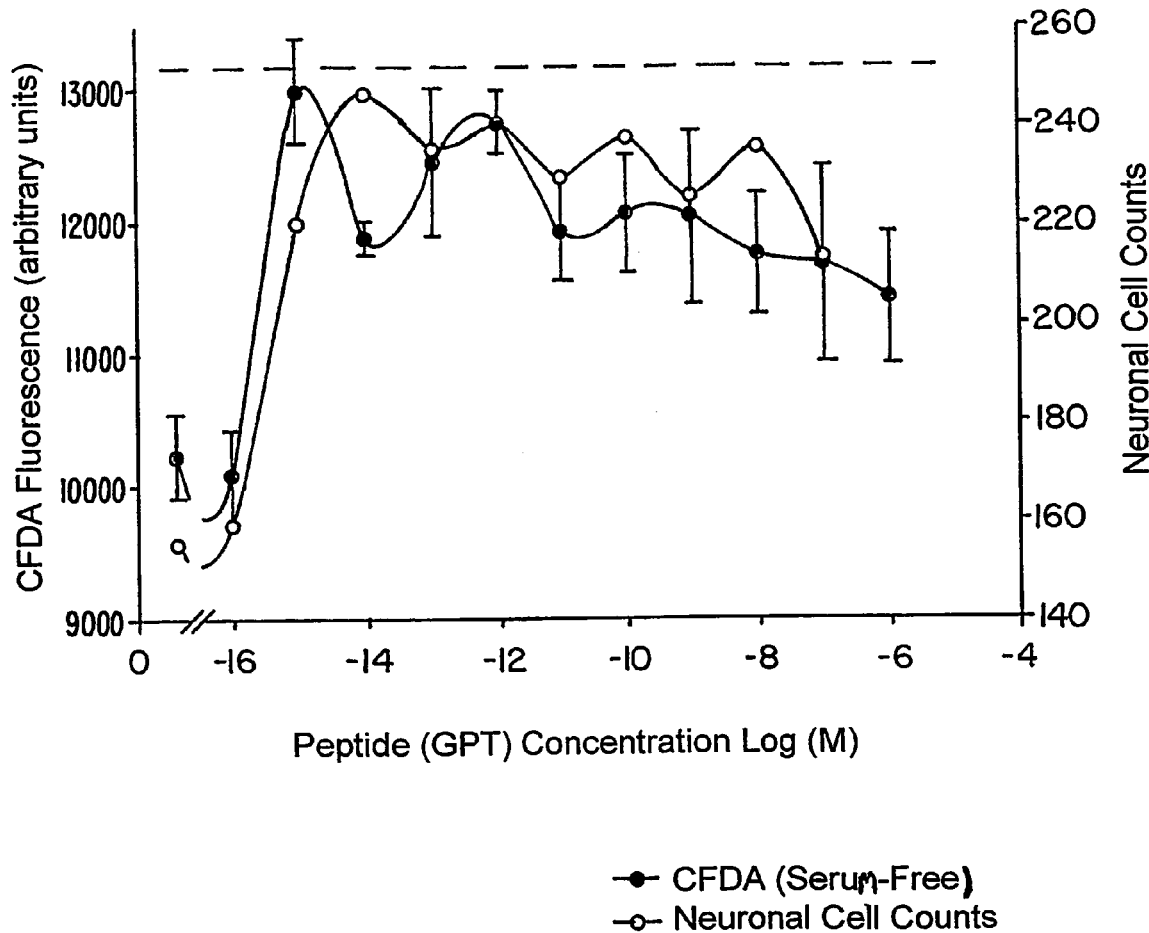
FIG. 6. Synthesized GPT peptide increases neuronal survival in TTX-treated cerebral cortical cultures. The peptide GPTADITLTK (GPT) was synthesized and treated as described in FIG. 2. Both neuronal cell counts and CFDA were used to assess neuronal survival. The dotted line represents the neuronal cell counts of control cultures. The error bar is the standard error.
Figure 7:
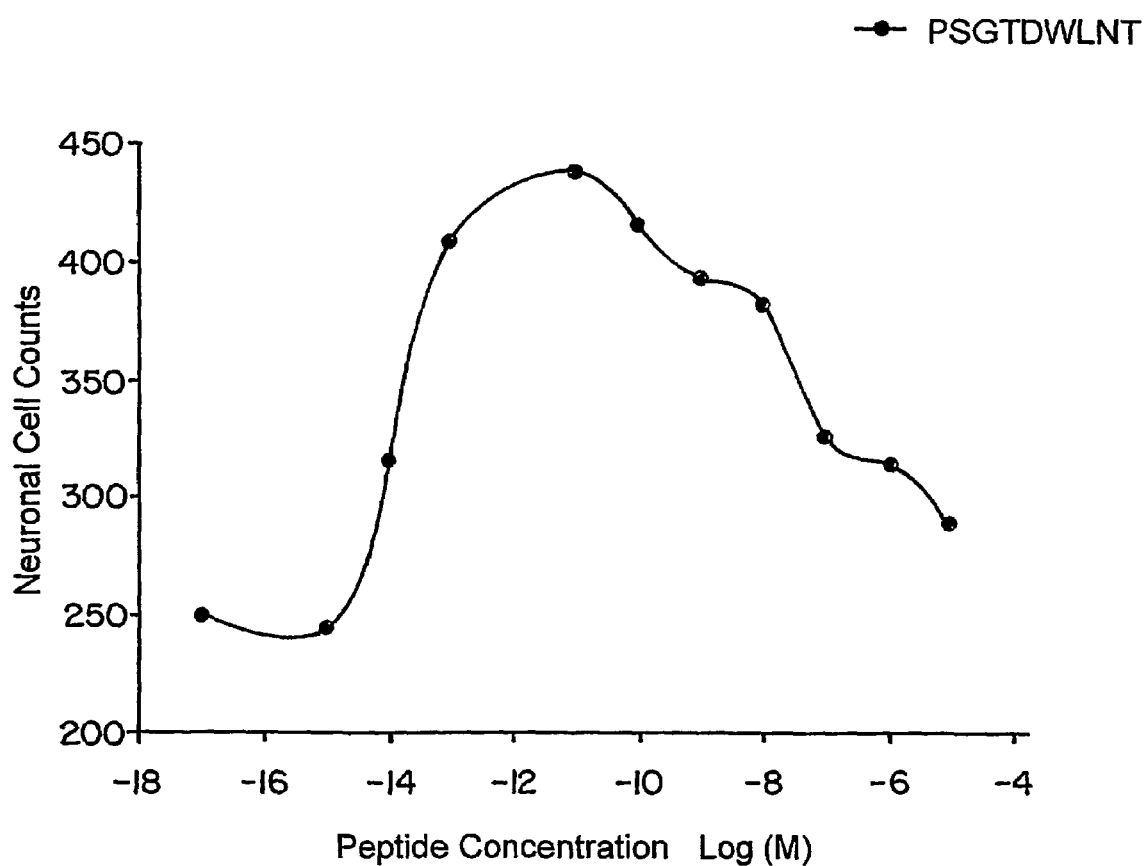
FIG. 7. Synthesized peptide PSGTDWLNT increases neuronal survival in TTX-treated cerebral cortical cultures. The peptide PSGTDWLNT is a truncated version of the digest peptide NPSGTDWLNTNNQANPFN. The shortened peptide PSG was synthesized and treated as described in FIG. 2. Neuronal cell counts were used to assess neuronal survival. Each point is the mean of two closely agreeing (<10%) values. These data provide evidence that shortened version of the digest peptide can exhibit potent protection and thus serves as an example for claim for all truncated peptides of the digest peptides.
Figure 8:
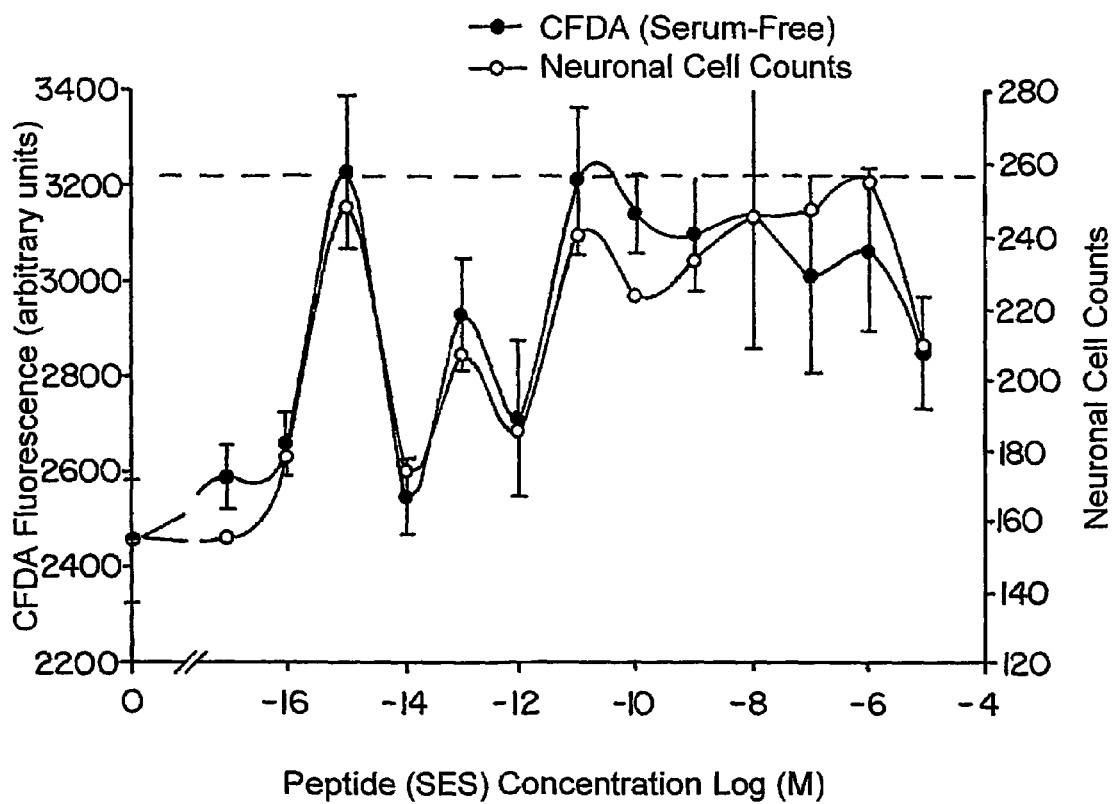
FIG. 8. Synthesized peptide SESSGTSELLTR increases neuronal survival in TTX-treated cerebral cortical cultures. The peptide SESSGTSELLTR (SES) was synthesized and treated as described in FIG. 2. Both neuronal cell counts and CFDA were used to assess neuronal survival. The dotted line represents the neuronal cell counts of control cultures. The error bar is the standard error.

One additional digest fraction containing SESSGTSELLTR was not available for testing, so this peptide was synthesized. To confirm the activity of the three peptides above plus SESSGTSELLTR (SES), the peptides were synthesized and tested for survival-promoting activity in the TTX-treated cortical cultures. As shown in FIG. 5, the synthesized NNST (peptide #1 above) exhibited neuroprotection as assayed by neuronal cell counts and the CFDA. In comparison to cultures treated with TTX alone, both assays indicated that an increase in neuronal survival was observed between $10^{-16}$ M and $10^{-14}$ M; with another peak of activity observed at $10^{-8}$ M treatment with NNST. Similarly, an increase in neuronal survival was observed with GPT (FIG. 6), PSG (FIG. 7) and with SES (FIG. 8).

Because the PSG fraction from the trypsin digests contained two peptides, the similar action of the synthesized PSG peptide in the cortical cultures strongly indicates that the biological action observed in the digest fraction was due to PSG. Importantly, a truncated form of PSG (PSGTDWLNT) exhibited potent survival-promoting activity which mimicked that activity of the full length digest PSG peptide (PSGTDWLNTNNQANPFN). Thus the survival-promoting activity of the digest peptides observed in part II were confirmed by the demonstration of neuroprotective action of the corresponding synthesized peptides. The peptides produce femtomolar-acting, neuroprotective activity in cerebral cortical cultures.

Example III

Figure 9:
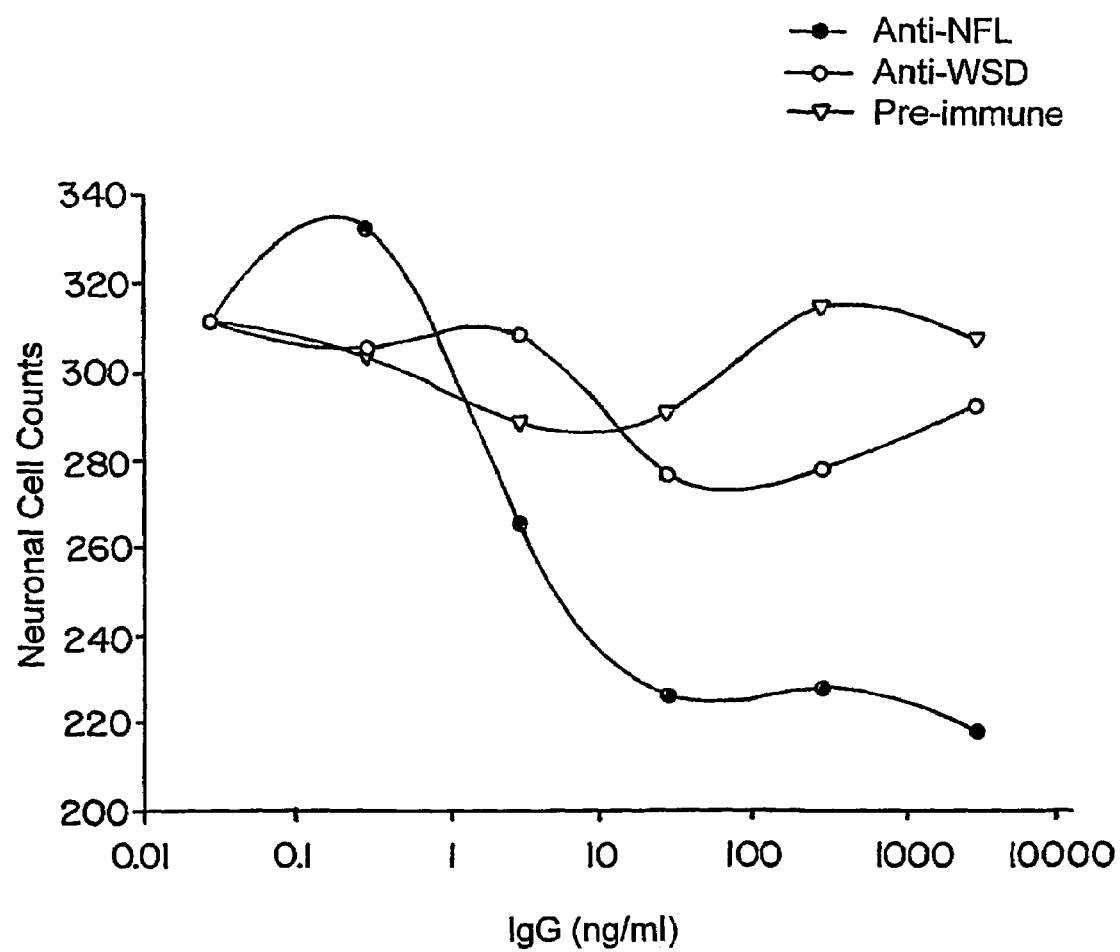
FIG. 9. Effects of antiserum against NFL and WSD peptide on neuronal survival in cerebral cortical cultures. IgG fractions of anti-NFL and anti-WSD were obtained with a protein A column utilizing a standard kit from Pierce Inc. The IgG antibodies were incubated for 5 five days in dissociated cerebral cortical cultures obtained from newborn mice. Neuronal cell counts were conducted the conclusion on the test period. Cultures were fixed and preserved as described previously (Brenneman & Gozes, *J. Clin. Invest.* 97:2299-2304 (1996)). Anti-NFL produced cell death.
Figure 10:
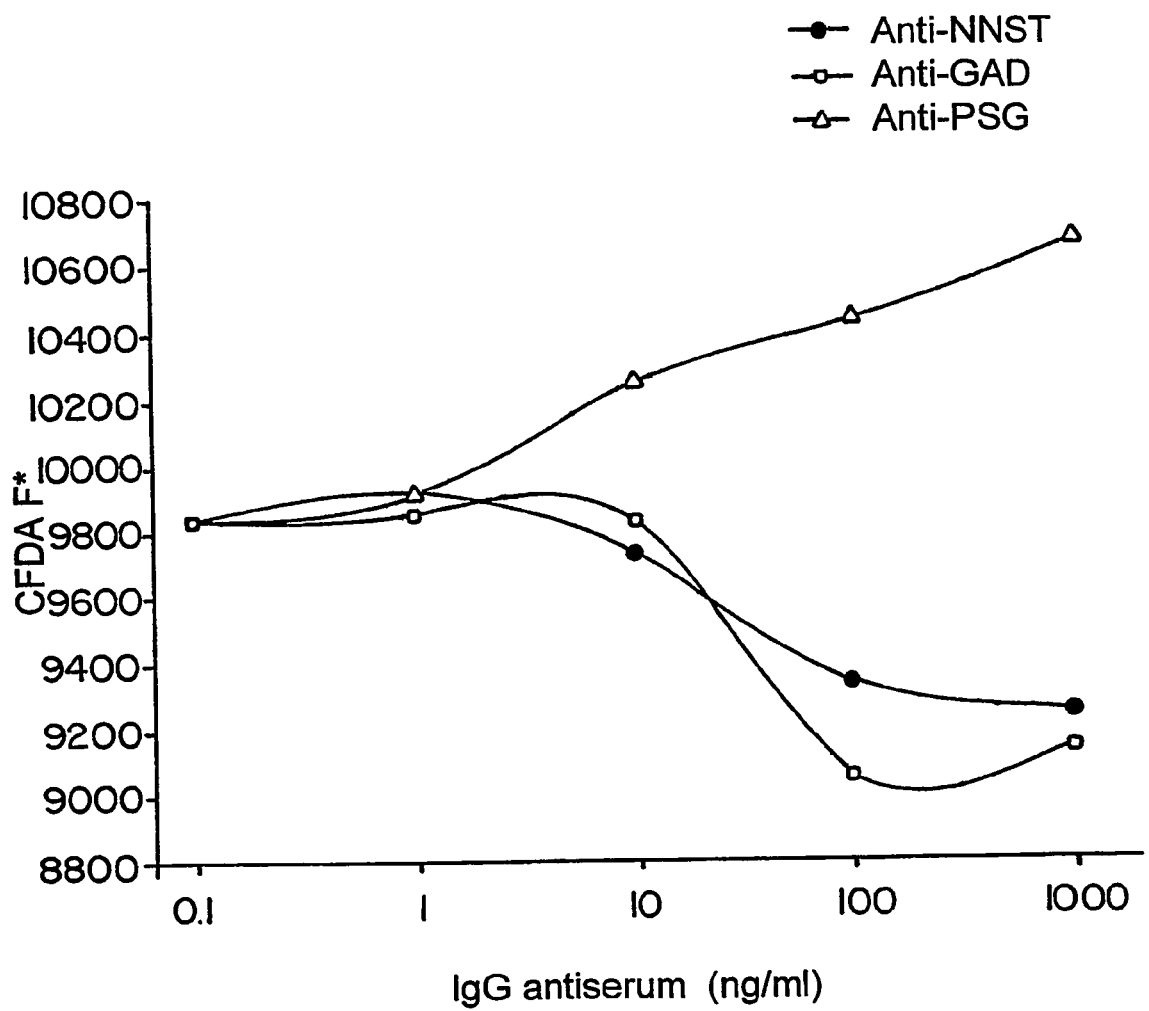
FIG. 10. Effects of antiserum against NNST, GAD and PSG peptide on neuronal survival in cerebral cortical cultures. IgG fractions of anti-NNST, anti-GAD and anti-PSG were obtained with a protein A column utilizing a standard kit from Pierce Inc. The IgG antibodies were incubated for 5 five days in dissociated cerebral cortical cultures obtained from newborn mice. Neuronal survival was assessed with CFDA as described in FIG. 2 above. Anti-PSG increased cell survival and anti-NNST produced cell death.
Figure 11:
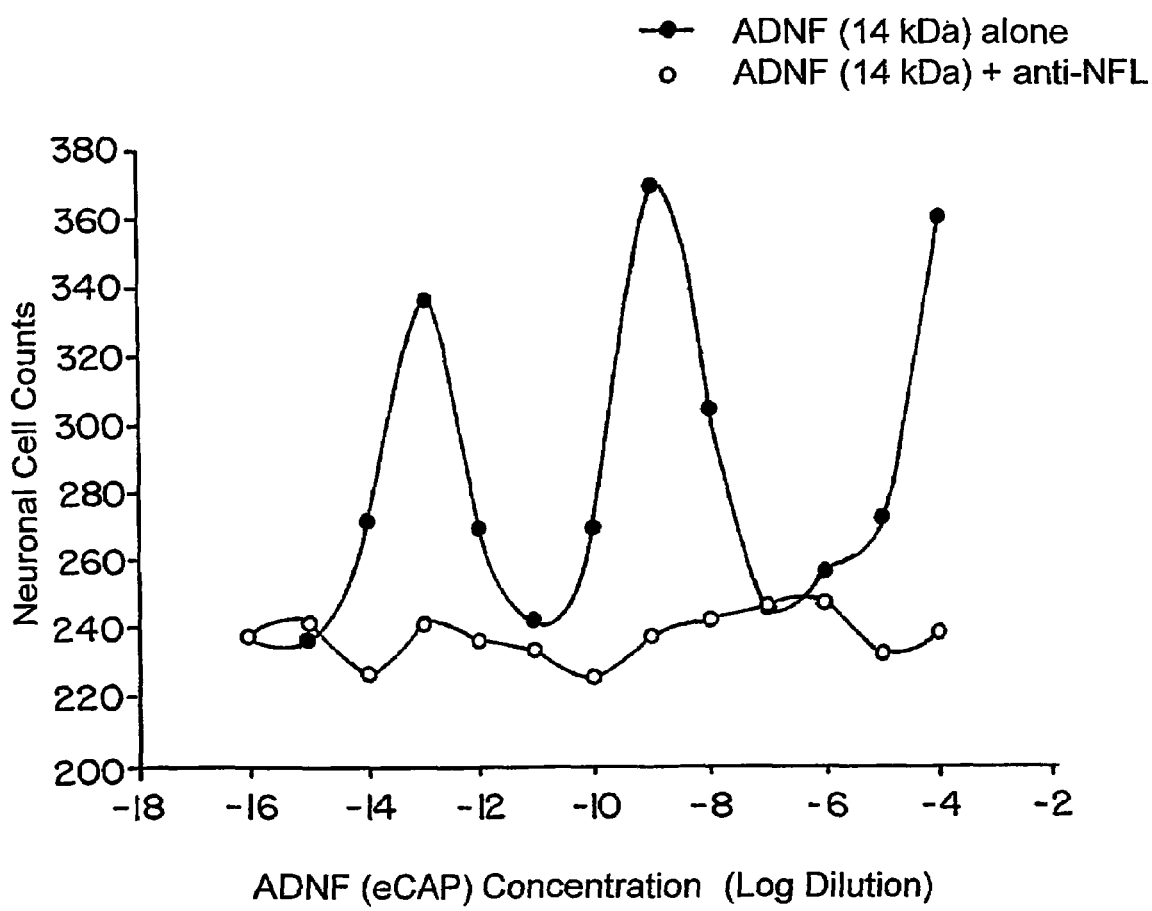
FIG. 11. Antiserum to NFL prevents ADNF I-mediated increases in neuronal survival. ADNF I was isolated by a multiple chromatographic steps as previously described. The purified ADNF I was further purified on an eCAP/SDS capillary the peak corresponding to 14 kDa was collected. The survival-promoting activity of the 14 kDa ADNF I complex is shown in the closed circles, with three peaks of activity evident. In sister cultures, 300 ng/ml of anti-NFL IgG was used to co-treat cultures given a dose response to ADNF I. All cultures but controls were also treated with 1 μM tetrodotoxin to prevent the release of endogenous ADNF I or the ADNF secretagogue YIP. Each point is the mean of two closely agreeing (<10%) values.

Antiserum to ADNF I Complex Peptides: Biological Activity, Affinity Chromatography and Immunohistochemical Localization A. Biological Activity To characterize the biological importance of newly discovered ADNF I-related peptides, antisera were generated to KLH-conjugated peptides in rabbits by standard protocols. As shown in FIG. 9, the IgG fraction of anti-NFL produced neuronal cell death in cerebral cortical cultures; whereas anti-WSD had little effect on neuronal survival. The pre-immune serum of the rabbit utilized for the anti-NFL antiserum production had no effect on neuronal survival. Other anti-peptides from ADNF I were tested in the CFDA assay. As shown in FIG. 10, a CFDA analysis that compared the effects of various anti-peptides from ADNF I demonstrated that antiserum to GAD (C-GADSNVAFQGKVIYRSESSGTSELLTR) or anti-NNST produced a small decrease in neuronal survival. In contrast, anti-PSG (C-PSGTWLNTNNQANPFN) produced a small increase in neuronal survival as measured in the CFDA assay. Although only the anti-NFL peptide had marked effects on neuronal survival, all the antiserum made to ADNF I peptides prevented ADNF I-stimulated neuronal survival. Examples of this effect are shown in FIG. 11. Biochemically isolated ADNF I was injected on an eCAP/SDS capillary column and the single 14 kDa peak was collected and confirmed to exhibit 3 peaks of survival-promoting activity. As shown in FIG. 11, co-treatment with anti-NFL (300 ng/ml) prevented the ADNF I-mediated increases in neuronal survival in TTX-treated cerebral cortical cultures. Similar studies were conducted with all antiserum to ADNF I peptides.

Figure 12:
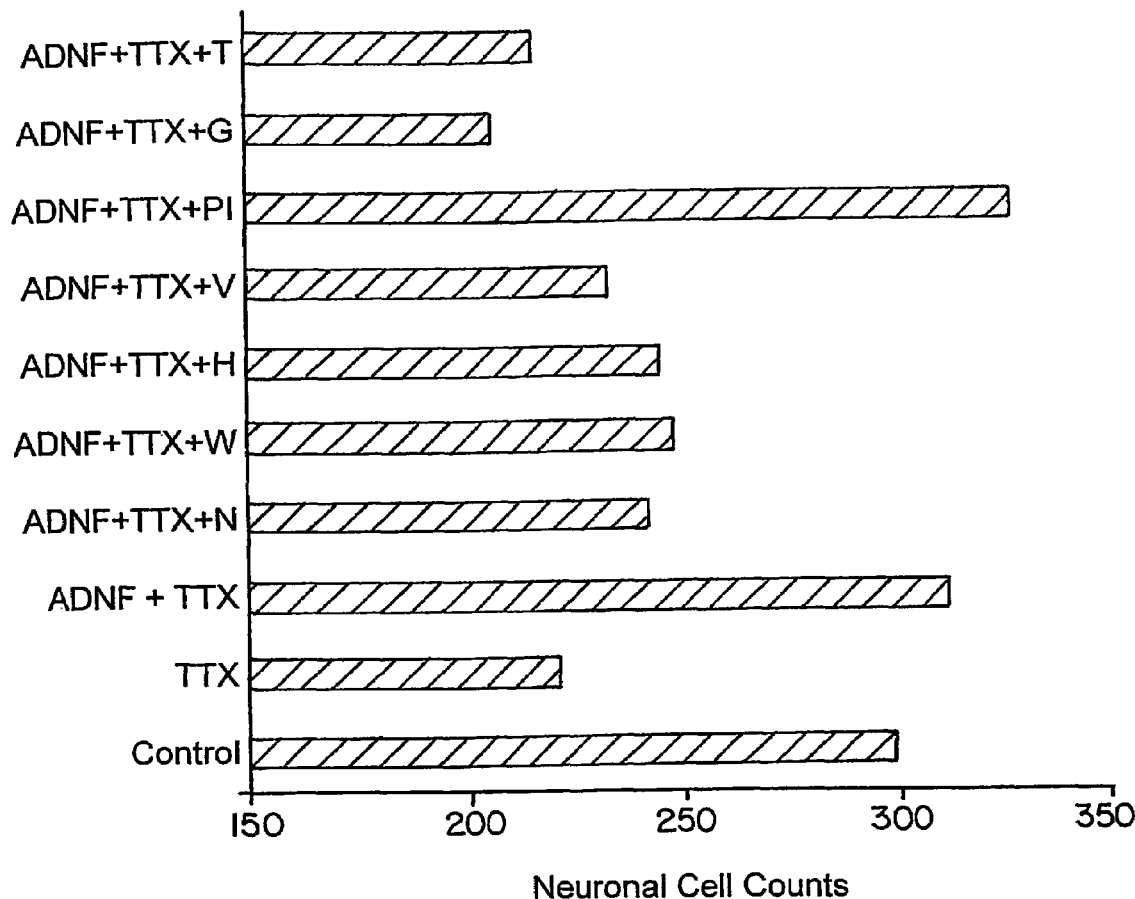
FIG. 12. Antiserum to ADNF I-related peptides prevent ADNF I-mediated increases in neuronal survival in cerebral cortical cultures. The ADNF I preparation described in FIG. 11 was used to co-treat cultures with various antiserum made against ADNF I-derived peptides: NNST, GAD, WSD, and NFL. In addition, antiserum to heat shock protein 60 (anti-hsp60) and to the ADNF I agonist ADNF-14 (VLGGGSALL-RSIPA {VGR}) were compared for their ability to block ADNF-mediated increases in neuronal survival. All antiserum were tested at 300 ng/ml. Abbreviations for the peptides are shown in the key.

A summary of these studies is shown in FIG. 12. Antiserum (IgG: 300 ng/ml) to the following peptides prevented ADNF I-mediated increases in neuronal survival:

A) C-WSDVGVSSGSAPDAFK

B) C-NNSTTYAPISANVSTALGSTAALPTAAGPV

C) C-NFL TSHYSAANSVVGGTNPGK

D) C-PSGTDWLNTNNQANPFN

E) C-GADSNVAFQGKVIYRSESSGTSELLTR

F) C-VLGGGSALLRSIPA

G) Anti-heat shock protein 60

These data demonstrate that epitopes interacting with these antibodies either are present on ADNF I (e.g., as subunits) or on accessory proteins of ADNF I that are important for ADNF I activity. These data further establish the immunological and biochemical characteristics of ADNF I and the relevance of the newly disclosed peptide structures.

B. ADNF I Affinity Isolation

Figure 13:
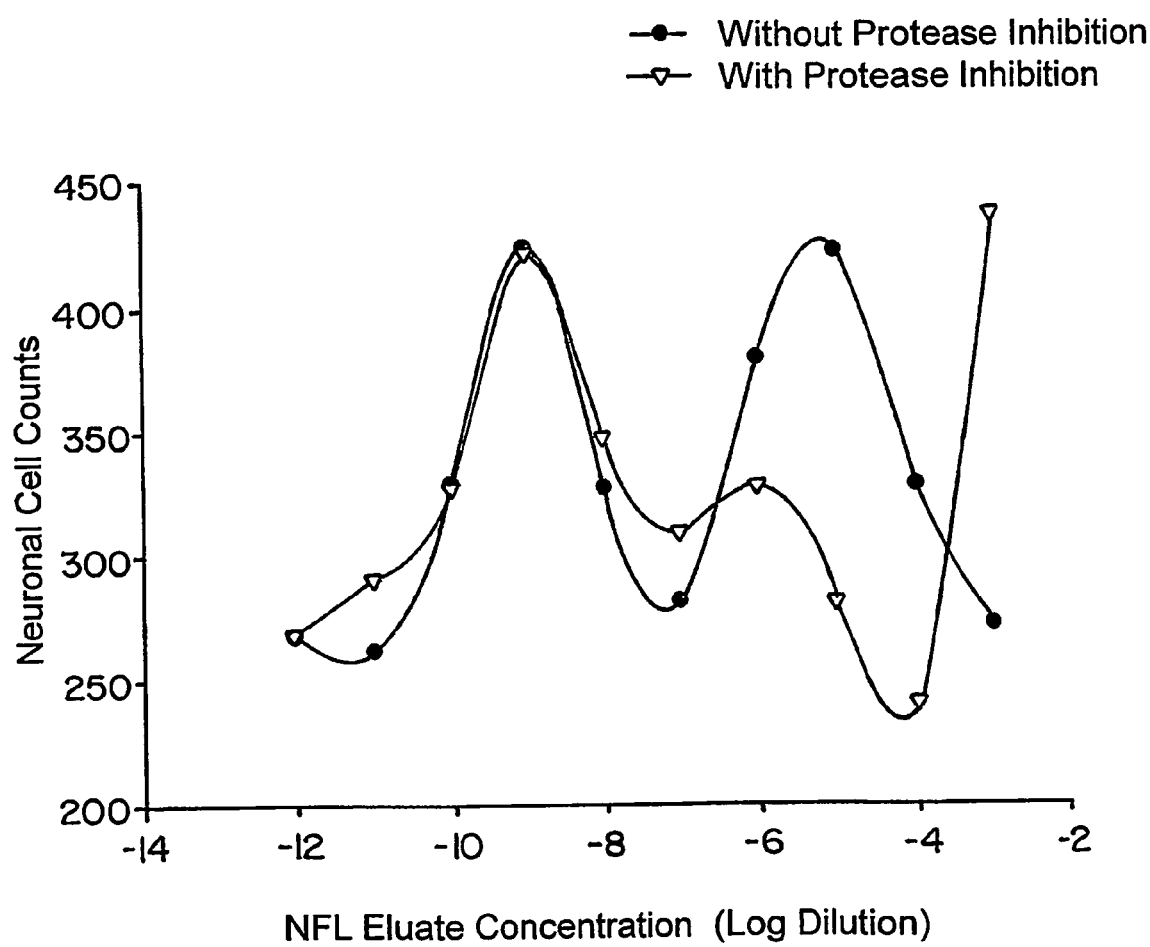
FIG. 13. Effect of a protease inhibitor cocktail on ADNF I-like immunoreactivity isolated by affinity magnetic beads with anti-NFL. For these experiments, the protease inhibitor cocktail #1 from Calbiochem was utilized. This cocktail inhibits a broad range of proteases and contains 500 μM AEBSF {4-[2-aminoethyl]benzenesulfonylfluoride HCl}, 150 nM aprotinin, 1 μM E-64, 0.5 M EDTA, 1 μM leupeptin hemisulfate. The protease cocktail was incubated with conditioned medium from VIP (0.1 nM)-stimulated astrocyte cultures for 3 hours at 4 degrees C. Conditioned medium without the cocktail was incubated in parallel at 4 degrees C. The ADNF I in the conditioned media was isolated with anti-NFL attached to magnetic beads. The beads containing the ADNF I were isolated by a magnet and the ADNF I from the two samples were eluted from the antibodies with 0.5 M citrate (pH 2). The survival-promoting activity of ADNF I immunoreactivity from CM without protease inhibitor (closed circles) in comparison to ADNF I immunoreactivity from CM with protease inhibitor (open inverted triangle) is shown.

A dose response to ADNF I measuring survival-promoting activity exhibited multiple peaks. Initial descriptions of activity indicated two peaks of activity; however, in the present case, ADNF I was shown to exhibit three peaks of activity. In FIG. 13, the effect of protease inhibition was observed. ADNF I-like activity was obtained by the use of anti-NFL IgG attached to magnetic beads. The eluted material (closed circles) indicated two peaks of activity. However, if a cocktail of protease inhibitors (Calbiochem. protease inhibitor cocktail #1) is added before the affinity capture and concentration, three peaks of activity were observed in the ADNF I-like protein eluted from the affinity bead. Furthermore, if the ADNF I preparation is maintained and stored under acidic conditions (pH 4.5), three peaks of ADNF I activity are also observed (see FIG. 2). These data support the observation that ADNF I exhibits a complex dose response and that one or more of the components is labile to a protease that either exists in conditioned medium or is a part of the ADNF I complex. These data further demonstrate that lowering the pH of the ADNF I complex prevented the loss of the third peak of activity for ADNF I.

Figure 14:
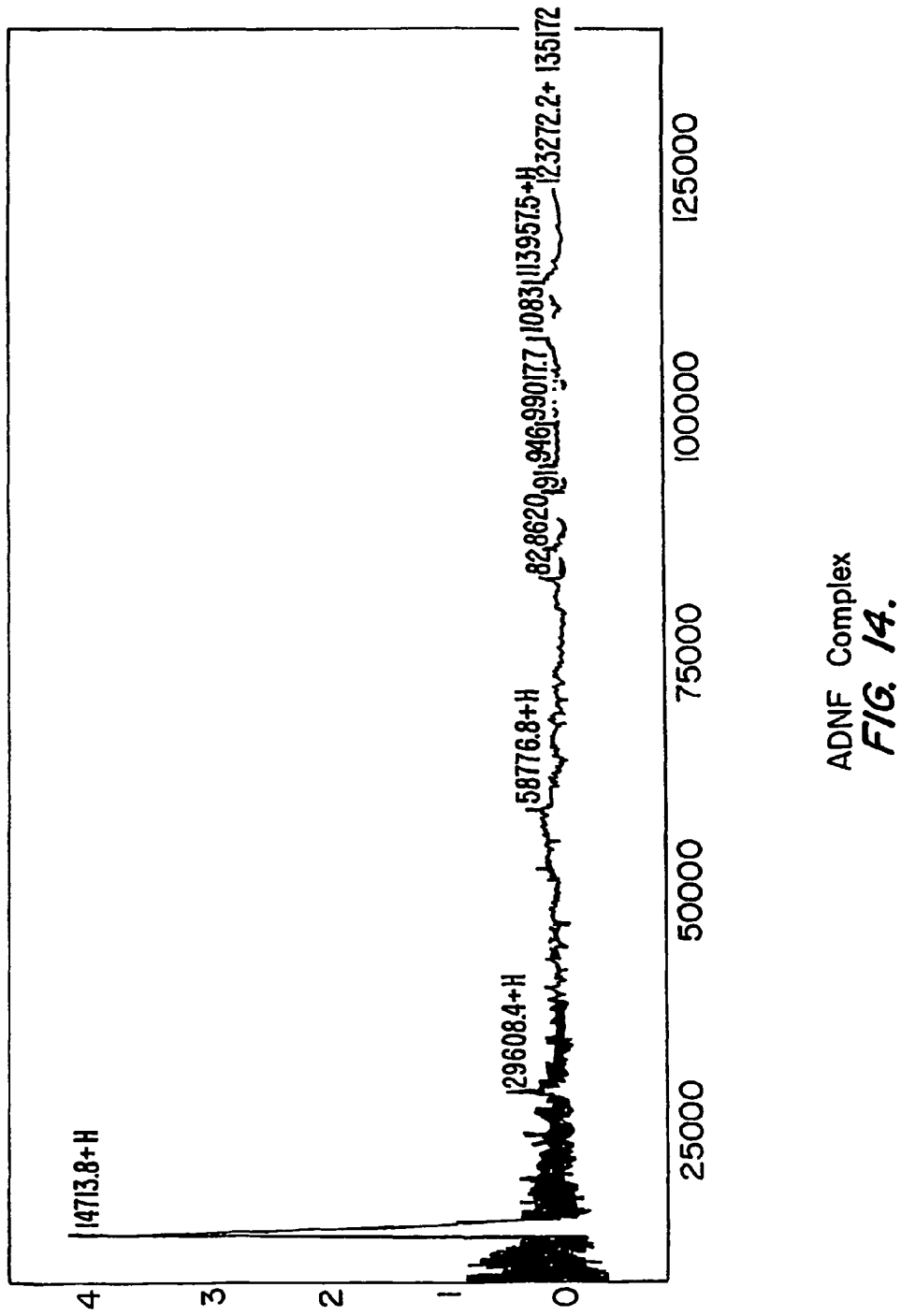
FIG. 14. SELDI analysis of ADNF I purified with an affinity column with anti-ADNF-14. ADNF I was isolated from conditioned medium from VIP-stimulated astrocyte cultures with an affinity column containing an IgG antibody prepared from ADNF-14, a 14 amino acid agonist of ADNF I that has been previously described (Brenneman & Gozes, *J. Clin. Invest.* 97:2299-2304 (1996)). ADNF I immunoreactivity was eluted with 0.5 M citrate (pH 2) and then concentrated in macrosep filtration units (Pall Filtron Corp) and microcon filtration units (Amicon corp). ADNF I complex was applied to a SELDI (surface-enhanced laser desorption/ionization) reverse phase chip (Ciphergen, Inc), washed three times with HEPES buffer and then allowed to dry. The surface was then treated with saturated sinapinic acid in 50% acetonitrile and 0.5% trifluoroacetic acid. The masses were determined with a time-of-flight mass spectrometer (Ciphergen Inc.).
Figure 15A:
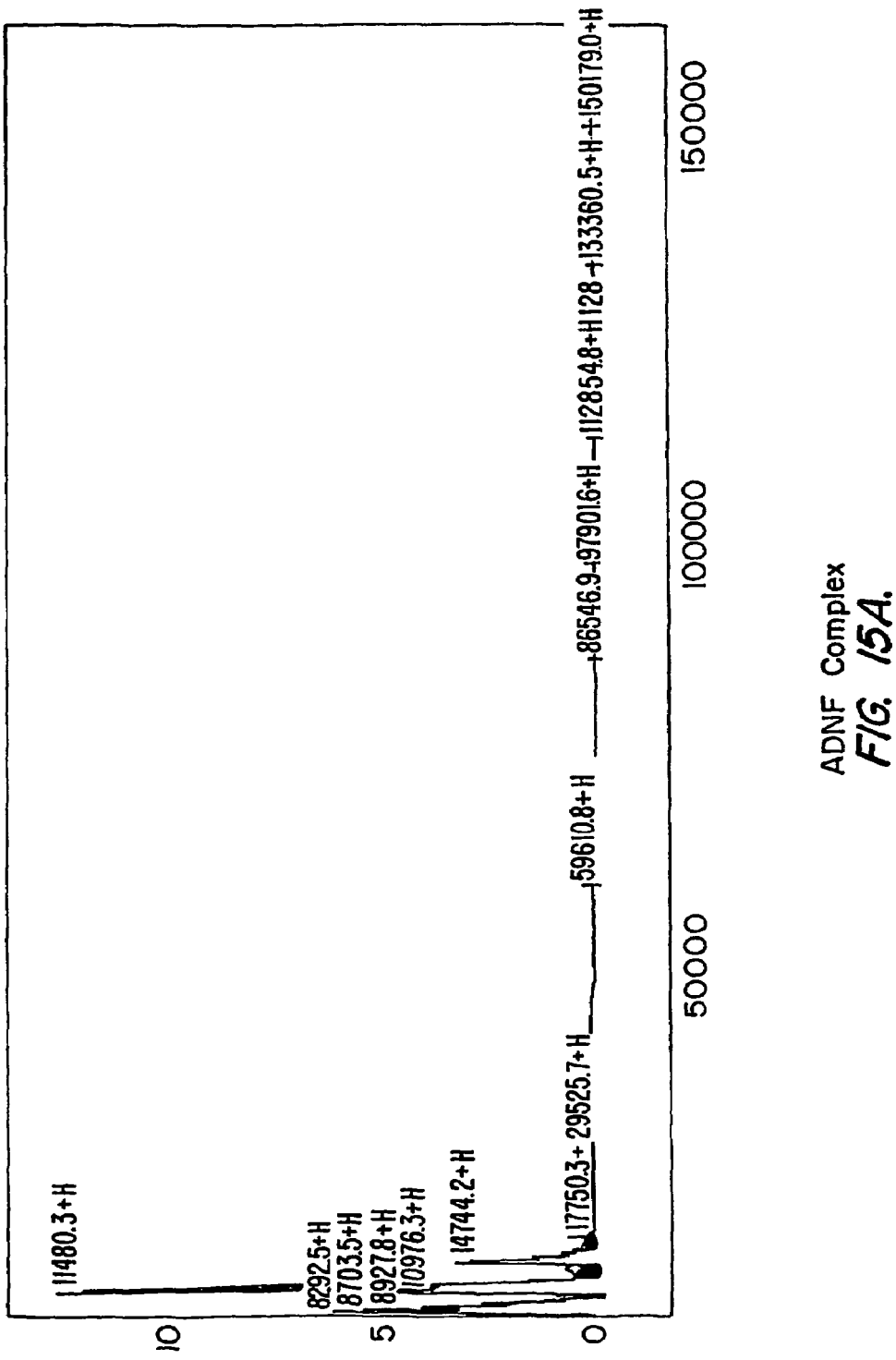
FIG. 15. A and B SELDI analysis of ADNF I complex purified as described in FIG. 14 with the exception of using an affinity column containing anti-NFL. SELDI analysis was done as described in FIG. 14.

For ADNF I, 14-amino acid peptide (VLGGGSALLR-SIPA) was sequenced and deduced from biochemically purified ADNF I. The 14 amino acid peptide (abbreviated: VGR) was used to prepare antiserum. Affinity columns utilizing anti-NFL and anti-VGR were used to extract ADNF I from conditioned medium from VIP-stimulated astrocytes. The proteins eluted from these ADNF I affinity columns were analyzed by Surface Enhanced Laser Desorption/Ionization (SELDI). For these studies, a reverse phase protein chip (Ciphergen Biosystems) was used to characterize ADNF I-like proteins eluted from the affinity columns. As shown in FIG. 14, the anti-VGR column isolated a single major peak at approximately 14,714 Daltons. As shown in FIGS. 15A and 15B, the eluted material from NFL affinity column showed a more complex pattern with major peaks at 14,744, 11480, 8292 and 4867. Thus the NFL column interacts with proteins not observed with the VGR column. Eluted material from both the VGR and NFL columns exhibited the three activity peaks of survival-promoting activity characteristic of ADNF I. In addition, multiples of 14,714 peak were observed (29608 and 58777), suggesting aggregations of the ADNF I complex. Thus, with either of these ADNF I antisera, 14 kDa ADNF I-like proteins can be isolated in a single step from a complex mixture of proteins. Applications of this technology include an assay for ADNF I and associated molecules.

C. Immunocytochemical Localization of ADNF I Peptide WSD

Figure 18:
FIG. 18. ADNF I-like immunoreactivity in cells of the reticular formation of the brainstem of the newborn rat brain. Immunocytochemistry with anti-WSD was performed as described for FIG. 16. Magnification: 40×.

To further characterize the ADNF I complex, the IgG antibodies to C—WSDVGVSSGSAPDAFK (WSD) were utilized to localize this epitope in the newborn brain. These data further describe the ADNF I complex and provide another means to delineate uniqueness from other proteins. Immunoreactivity was localized throughout the brain including the forebrain structures of the cortex and hippocampus. In anterior regions, immunoreactivity was most evident in the fiber-like structures in the basal forebrain as shown in FIG. 16. The most intense immunoreactivity was found in the hindbrain and brain stem structures where cells and/or fibers were identified in the spinal trigeminal nuclei, parabrachial nuclei, para abducens nuclei (FIG. 17), cerebellar nuclei and numerous cells within the reticular formation (FIG. 18). Furthermore, ADNF I-like immunoreactivity was also detected in the newborn rat brain and E9 mouse decidua with rabbit antibodies to the peptides NNST and GAD.

D. Western Blot Analysis of Anti-Peptides from ADNF I

Figure 19:
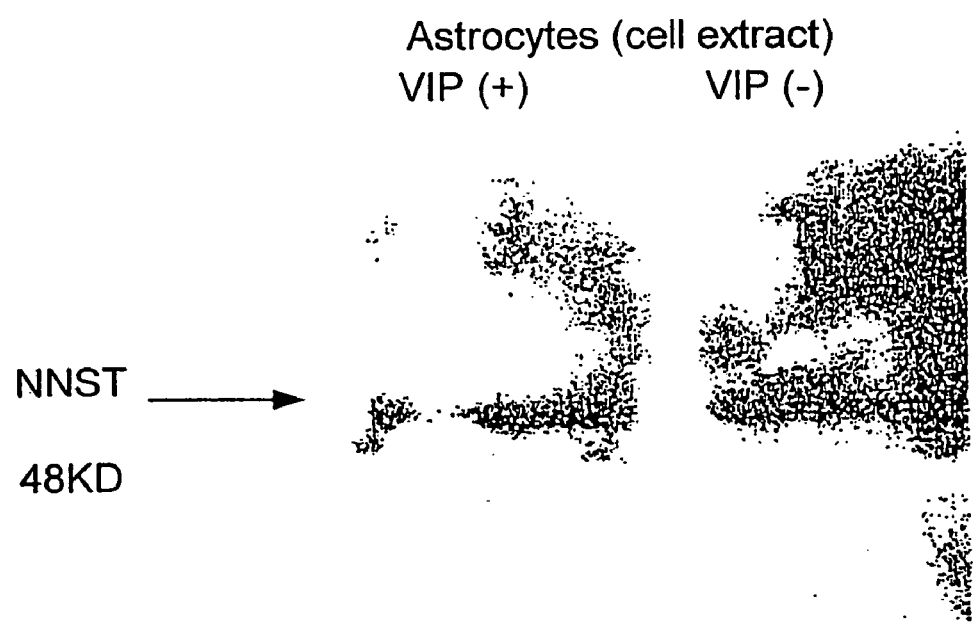
FIG. 19. Western analysis of immunoreactivity for NNST peptide in astrocytes lysate. A 1:300 dilution of an affinity purified antibody to NNST was used for the immunoblot analysis of a lysate of cultured astrocytes. A comparisons was made between lysates of VIP-stimulated versus control astrocytes cultures.

To further delineate the nature of the ADNF I complex and peptides, a Western analysis was performed on cell extracts of astrocytes. As shown in FIG. 19, anti-NNST detected an intracellular band at 48 kDalton. This band was increased in the lysate of astrocyte cultures stimulated with 0.1 nM VIP in comparison to lysates from control cultures. These data suggest that the NNST peptide exists as is a higher molecular protein or a prepro-form before secretion.

Example IV

Figure 20:
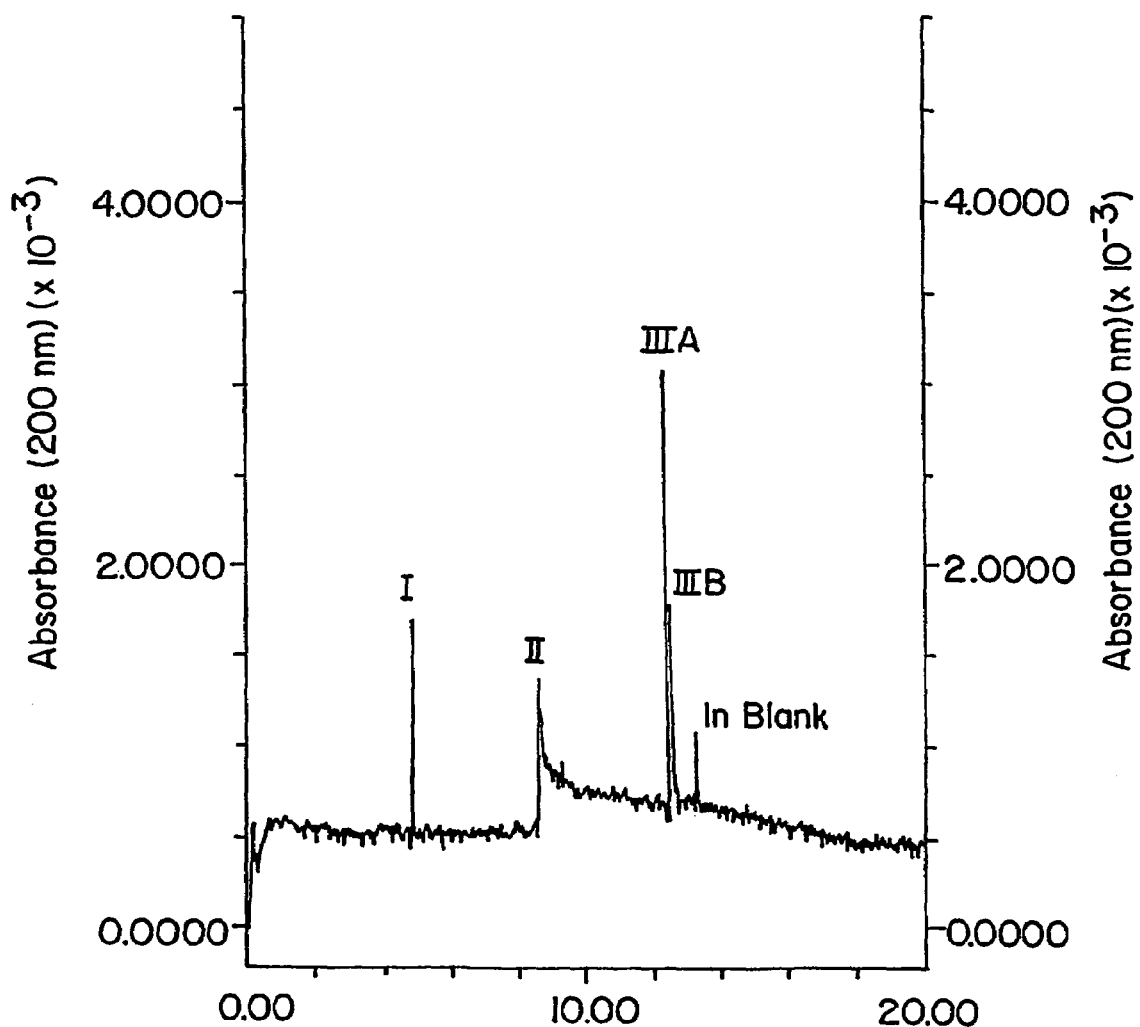
FIG. 20. N-CHO coated capillary electrophoretic analysis of ADNF I. ADNF I was isolated by multiple chromatographic steps as previously described. The samples was desalted in macrosep filtration units (Pall Filtron Corp) and microcon filtration units (Amicon corp). The replacement buffer was 10 mM monobasic phosphate (pH 4.5). The conditions for N-CHO electrophoresis is as follows: running buffer was 100 mM monobasic phosphate (pH 4.55). The polarity was reversed to run to positive. The injection was 70 sec at 80 psi. Samples were diluted 1:3 with water before injection. Samples were monitored with absorbance at 200 mm. The distance to the flow cell was 60 cm. The numeral above the peaks indicate the number of the ADNP I complex component: I, II, IIIA and IIIB.

Isolation of Components of ADNF I and their Characterization: N-CHO Capillary Electrophoretic Analyses A. Capillary Methodology To establish the locus of the newly discovered peptide elements within the ADNF I complex, a procedure was devised to separate the ADNF I components and then antiserum interaction studies were conduced on isolated components of the ADNF I complex to establish their characteristics. Five other chromatographic procedures (anion exchange, cation exchange, size exclusion, hydrophobic interaction and reverse phase) did not provide any separation of these components. As shown in the electropherogram in FIG. 20, biochemically purified ADNF I was separated into four peaks: I, II and two closely migrating peaks: IIIa and IIIb. One additional peak was observed and also appeared in the blank. For this separation, an N-CHO capillary (75 μm i.d.) obtained from Beckman Instruments was used. A constant current of 50 μA was employed using a 100 mM monobasic phosphate buffer, pH 4.55. The injection times were 70 sec at 80 psi. UV absorbance at 200 nm was used to detect the peaks. The N-CHO column is based on polyvinyl alcohol which minimizes the effects of electroosmotic force and has a very hydrophobic surface. The N-CHO column surface is designed to separate carbohydrate moieties, these data strongly suggest that the components of ADNF I complex are glycosylated and that disruption of the glycopeptides is necessary for separation of the ADNF I complex. These conditions reveal the components of ADNF I complex and can be used in an assay for ADNF I complex for potential diagnostic purposes.

B. Biological Activity of ADNF I Complex Components

Figure 21:
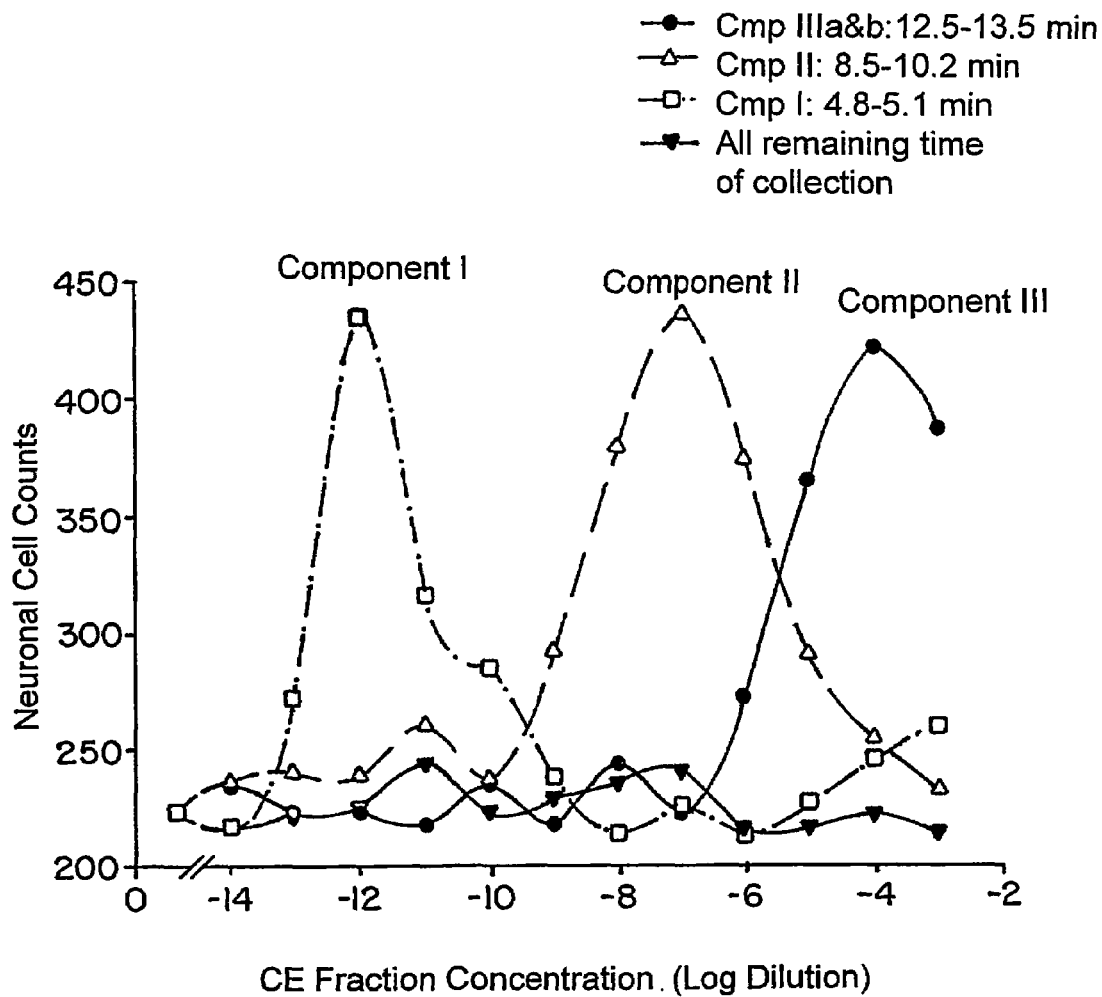
FIG. 21. Survival-promoting activity associated with ADNF I complex components collected in peaks from N-CHO capillary electrophoresis. ADNF I isolated by previously described means was fractionated on N-CHO capillary electrophoresis as described in FIG. 20. Five collections were made into 50 μl of running buffer (100 mM monophosphate buffer, pH 4.55). Three components of ADNF I complex were collected as follows: component I (shaded squares) was obtained between 4.8 and 5.1 min; component II (open triangles) was obtained tween 8.5 and 10.2 min; and components IIIA and IIIB were collected between 12.5 and 13.5 min. All remaining time of collections were made into a single tube (closed inverted triangles) Each of the collections was serially diluted in phosphate buffered saline and assessed for biological activity in tetrodotoxin-treated cerebral cortical cultures. In sister cultures, various IgG antibodies (300 ng) were tested for their ability to block the biological activity of various ADNF I complex components at dilutions of their peak efficacy. Summary of these findings is shown in the legend. These data indicate that all of the survival-promoting activity was confined to the time of collection corresponding to the three peaks. No activity was observed apart from these peaks. Each peak showed a distinct pattern of interaction with the panel of antibodies and each differed greatly in potency from the other ADNF I complex components.

To further establish the characteristics of the ADNF I complex, the peaks corresponding to component I (5.1 min) component II (8.5 min) and a combination of components IIIa and IIIb (12.3-12.6 min) were isolated into individual fractions. These fractions were tested in TTX-treated cerebral cortical cultures over a broad range of dilutions as shown in FIG. 21. Each of the isolated CE peaks exhibited a monotonic peak of biological activity over a wide range of concentrations. Each of the components showed similar efficacy, but differed greatly in their relative potency. Component I exhibited the most potent activity, with component II having a potency of 10,000 times less than component I. Component III was the least potent, with a relative potency 100,000,000 times less than component I.

The antibodies to the newly discovered peptides, as well as antiserum previously described to interact with ADNF I (Brenneman & Gozes, *J. Clin. Invest*. 97:2299-2307 (1996)) were compared for their ability to block the biological activity of each of the three ADNF I complex components isolated by N-CHO- capillary electrophoresis.

Component I was blocked by antibodies to NFL, WSD, PSG., NNST and NAP. Component II showed a different patten of blockade with activity blocked by WSD, PSG, VGR and GAD. Component III, the least potent of the ADNF I complex components, was blocked only by GAD, VGR and Hsp60. These data are consistent with the model that ADNF I is complex of peptides that have separable survival-promoting activity. Importantly, no pre-immune serum had any effect on any of the three components of ADNF I.

Example V

Homology Between ADNF I Amino Acid Sequence and Known Proteases

The rationale for investigating the hypothesis that ADNF I components may be proteases resides in the recognition of amino acid sequence homology among ADNF I peptides and known proteases. Evidence is presented for three types of proteases: a subtilisin, furin-type protease, an aspartyl protease and cysteine proteases.

Figure 23:
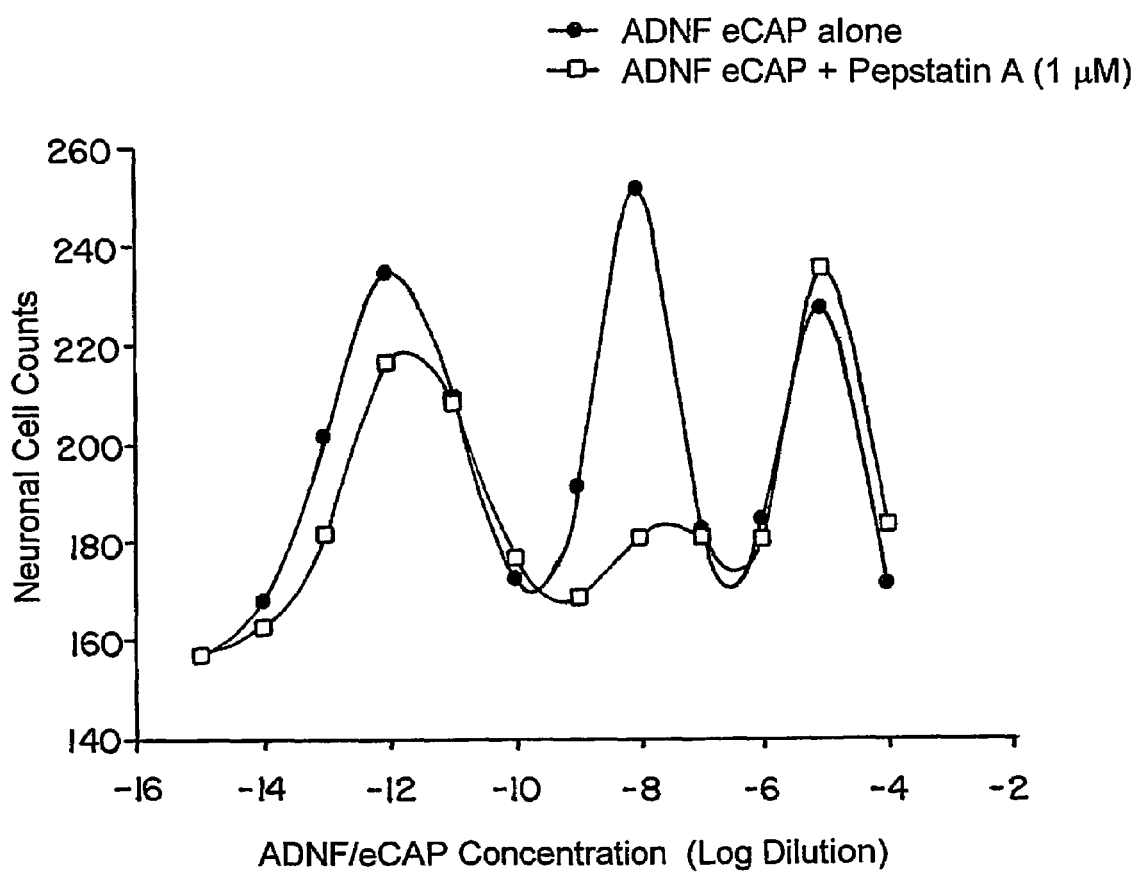
FIG. 23. Effect of pepstatin A on ADNF I-mediated protection from neuronal cell death produced by tetrodotoxin. Experiments were conducted as described in FIG. 22, with the exception that 1 μM pepstatin A alone was used to inhibit protease activity rather than the Calbiochem cocktail. Pepstatin A is a specific inhibitor of aspartyl proteases. For these experiments, pepstatin A was dissolved in methanol at 1 mg/ml. This was a 100× working stock solution that was added to the ADNF I preparation. Pre-treatment with pepstatin A blocked the survival-promoting activity of only the peak appearing at $10^{-8}$ dilution.

As shown in FIG. 23, pre-treatment of the 14 kDa purified ADNF I complex with an aspartyl protease inhibitor Pepstatin A) prevented the peak of activity observed at 10-8 dilution. These data suggested that component II of the ADNF I complex (peak observed at 10-8 dilution) was an aspartyl protease; whereas component III (peak observed at 10-5 dilution) was not affected. Component I (peak observed at $10^{-12}$ dilution) showed a small decrease with Pepstatin A pre-treatment. These data indicate that the neuroprotective activity of component II can be blocked by an aspartyl protease inhibitor

TABLE 1

| | |
|---|---|
| A. Subtilisin active site: | GTSAALPTAAG KEX1_KLULA P09231 |
| A portion of NNST Peptide from component I: | GSTAALPTAAG |
| 9/11 identical | |
| 11/11 identical or conserved | |
| Subtilisin from Bacillus: | TSHPDLKNQIIGGKN |
| A portion of NFL Peptide from component I: | TSHYSAANSVVGGTN |
| 7/14 identical | |
| B. Eukaryotic aspartyl protease active site: | VDVDSGSAPIVGF |
| A portion of WSD peptide from component II: | VGVSSGSAPDAF |
| 9/12 identical | |
| C. Cysteine protease of early leaf senescence: | VATCSSYPVVA |
| A portion of VDP peptide (component unknown) | VDPASGYPIVG |
| 5/11 identical | |

Example VI

Figure 22:
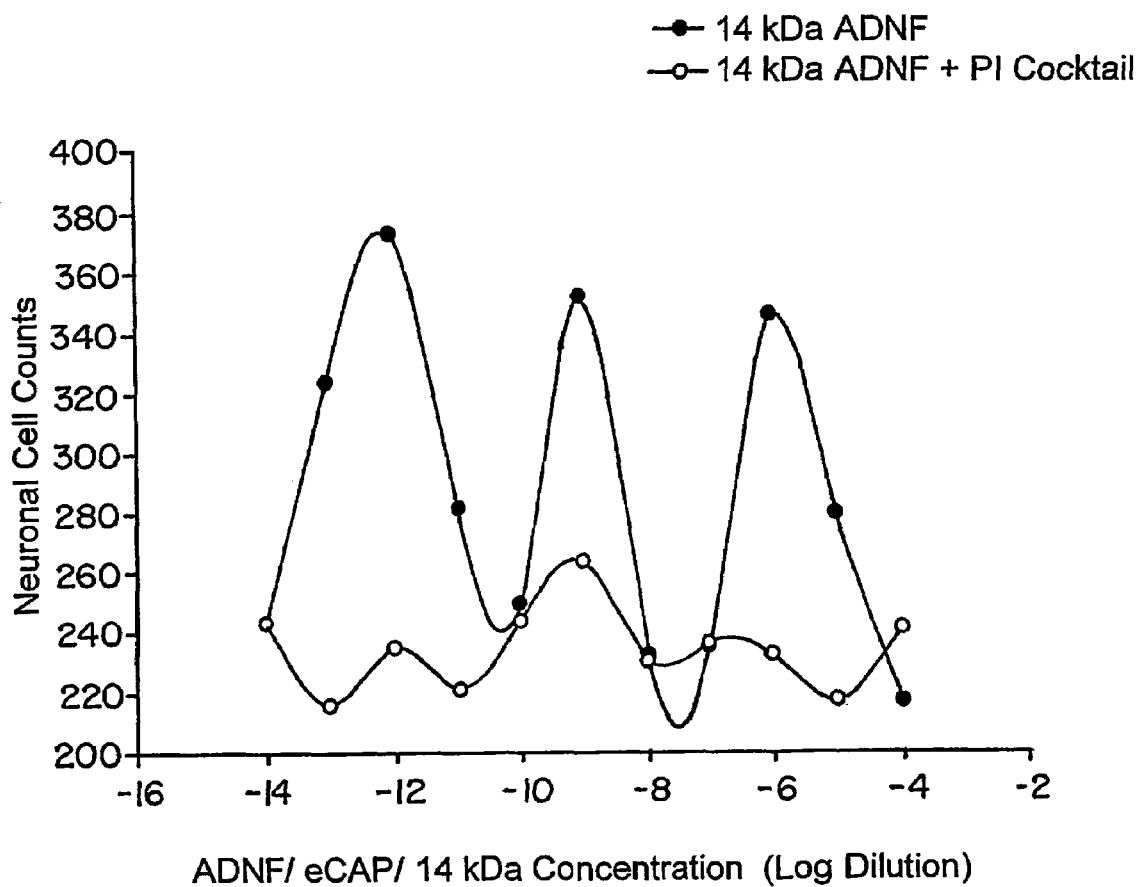
FIG. 22. Mixed cerebral cortical cultures composed of neurons and glia were tested for the effects of protease inhibition on ADNF I-mediated protection from neuronal cell death produced by electrical blockade with tetrodotoxin (TTX). As previously described (Brenneman & Gozes, *J. Clin. Invest* 97:2299, 1996), purified ADNF I was added only once to the cultures three days after seeding neurons onto the confluent feeder layer of astrocytes. To measure and verify the purification of the ADNF I, the ADNF I preparation was isolated on eCAP/SDS capillary electrophoresis. The peak appearing in the 14 kDa region of the capillary was isolated into 50 ul of running buffer. The running and sample buffer for these analyses was provided by a kit provided by Beckmann Instruments. Electrophoresis was conducted with 8.1 kV constant voltage. The pressure injection time was 50 sec at 80 psi. The concentration of the ADNF I preparation was estimated to be 1 μM. Ribonuclease A was used as a standard for this analysis. Serial dilutions of the ADNF I preparation were tested in the presence of 1 μM TTX. Prior to treatment and serial dilutions, the ADNF I preparation was mixed with a cocktail of protease inhibitors prepared by Calbiochem (La Jolla, Calif.). The mixture of protease inhibitors included 500 μM AEBSF-HCl, 150 nM aprotinin, 1 μM E-64, 05 mM EDTA and 1 μM leupeptin hemisulfate. The concentrations of inhibitor were the final concentration after mixing with the ADNF I preparation. The treatment period was 4 days. The termination, cultures were fixed in glutaraldehyde as described previously (Brenneman & Gozes, 1996) and the neurons counted without knowledge of the treatment group. Control studies indicate that the protease inhibitor cocktail itself had no survival-promoting activity used at the dilutions (1:10,000) employed in the present experiment.

Effect of Protease Inhibitors and the Survival-Promoting Activity of the ADNF I Complex As shown in FIG. 22, pre-treatment of the 14 kDa purified ADNF I complex with a protease inhibitor cocktail prevented the neuroprotective action of ADNF I against apoptotic death produced by 1 μM tetrodotoxin. In the dissociated cerebral cortical cultures, the ADNF I complex-produced three peaks of protective activity. Pre-treatment with the protease inhibitor cocktail prevented the action of all three peaks. The protease cocktail was composed of: 500 μM AEBSF [4-(2-aminoethyl)benzenesulfonylfluoride HCl], 150 nM aprotinin, 1 μM E-64 (loxastatin), 0.5 mM EDTA and 1 μM leupeptin. The protease inhibitor cocktail was mixed with purified ADNF I complex prior to diluting and treating the cultures. No biological activity was observed after treatment with protease inhibitor cocktail alone when tested at the same dilutions as that done with ADNF I. These data indicate that the neuroprotective activity of the ADNF I complex is blocked by protease inhibitors, indicating that the ADNF I complex is composed of protease(s) and/or that it interacts with protease(s).

and demonstrated that component II is an aspartyl protease. Evidence in cell-free enzyme assays will be shown for component II.

Figure 24:
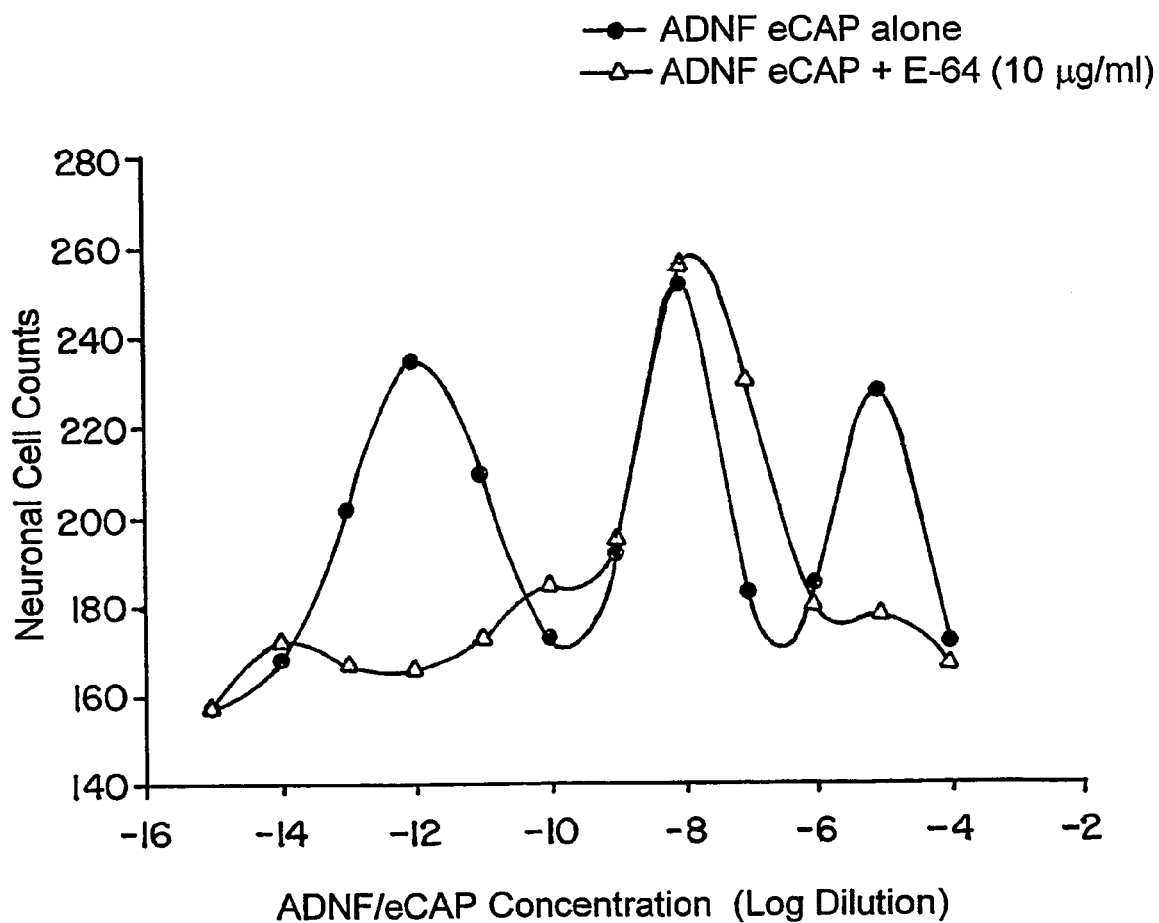
FIG. 24. Effect of E-64 on ADNF I-mediated protection from apoptotic neuronal cell death by treatment with tetrodotoxin. Experiments were conducted as described in FIG. 22, with the exception that 10 μg/ml E-64 was used to irreversibly inhibit cysteine proteases. E-64 was dissolved in ethanol at 1 mg/ml. Pre-treatment with E-64 blocked the survival-promoting activity on the first and third peak of the ADNF I complex appearing at $10^{-12}$ and $10^{-5}$ dilution.

As shown in FIG. 24, pre-treatment of the 14 kDa purified ADNF I complex with a cysteine protease inhibitor (E-64) prevented the peaks of activity observed at $10^{-12}$ and $10^{-5}$ dilution. These data suggested that component I of the ADNF I complex (peak observed at $10^{-12}$ dilution) was a cysteine protease, as well as component III (peak observed at $10^{-5}$ dilution). The protective activity of Component II was not diminished by E-64. These data indicate that the neuroprotective activity of components I and III were blocked by a cysteine protease inhibitor and demonstrated that component I and III were serine proteases.

Figure 25:
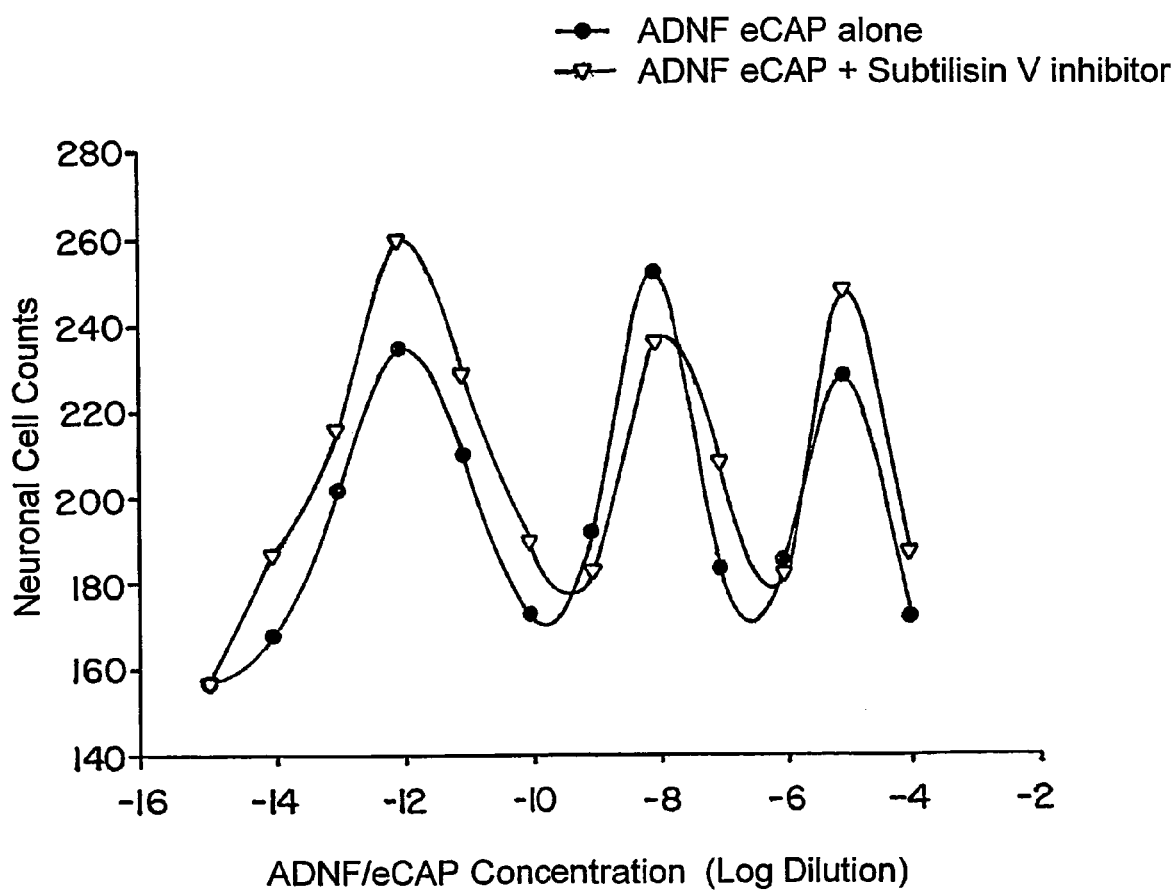
FIG. 25. Effect of subtilisin V inhibitor (Boc-Ala-Pro-Phe-NHO-Bz-pCl) on ADNF I-mediated protection from apoptotic neuronal cell death produced by 1 μM tetrodotoxin. Experiments were conducted as described in FIG. 22, with the exception that 0.1 mM subtilisin V inhibitor was used to treat the ADNF I preparation. The 100× stock solution of the inhibitor was 1 mg dissolved in 0.2 ml of ethanol. This inhibitor is an irreversible cysteine and serine protease inhibitor. This inhibitor enhanced the activity of components I and III, the peaks at $10^{-12}$ and $10^{-5}$ dilution.

As shown in FIG. 25, pre-treatment of the 14 kDa purified ADNF I complex with a subtilisin V inhibitor enhanced the peaks of activity observed at $10^{-12}$ and $10^{-5}$ dilution. These data suggest that a subtilisin-like protease degrades portions of the ADNF I complex. These experiments were done at physiological pH. More data suggesting the presence of a subtilisin-like protease intrinsic to the ADNF I complex is found in part 5 below. These data suggest that even at physiological pH, components I and II of the ADNF I complex may be degraded by an intrinsic subtilisin-like protease in the ADNF I complex.

Example VII

Figure 26:
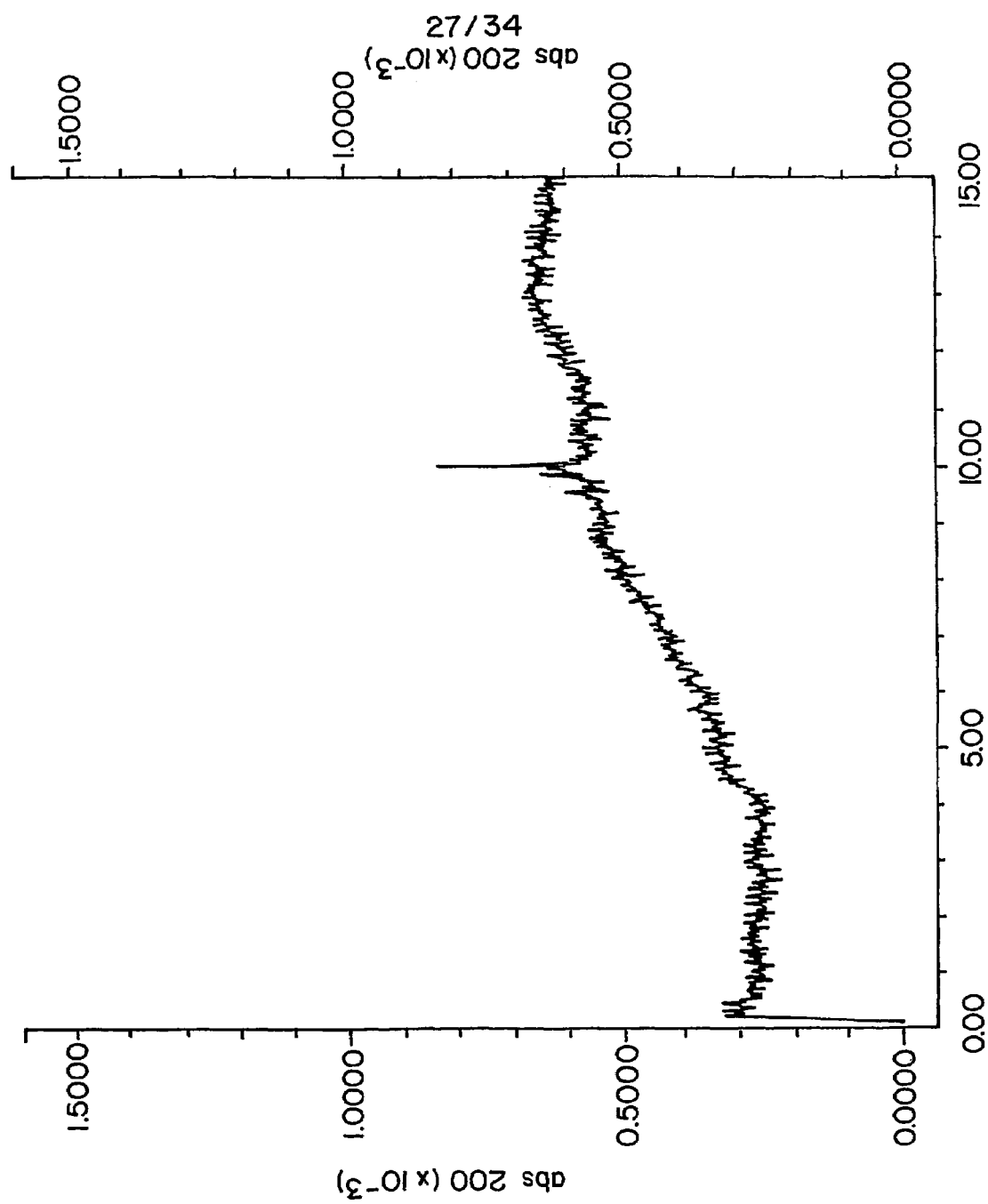
FIG. 26. The N-CHO electropherogram of purified component 2 preparation from ADNF I is shown. This preparation was obtained by immunopurification from an affinity (anti-VLGGGSALLRSIPA) column followed by acetone precipitation. A single peak at 200 nm was observed. The conditions of the capillary electrophoresis was: 100 mM monobasic phosphate buffer, pH, 4.55; 50 μA constant current; 70 sec injection at 80 psi; 75 um i.d capillary (Beckman instruments). The N-CHO column surface is designed to separate carbohydrate moieties. The preparation utilized for protease assays appeared to be a single peak with a retention time consistent with that component 2 as previously described (DHHS Ref No.: E-209-01/1-0). The protein concentration of this preparation was estimated to 1 μM based on standard curves generated to glycoprotein alpha-1 acid analyzed under identical conditions and detection at 280 nm.
Figure 27:
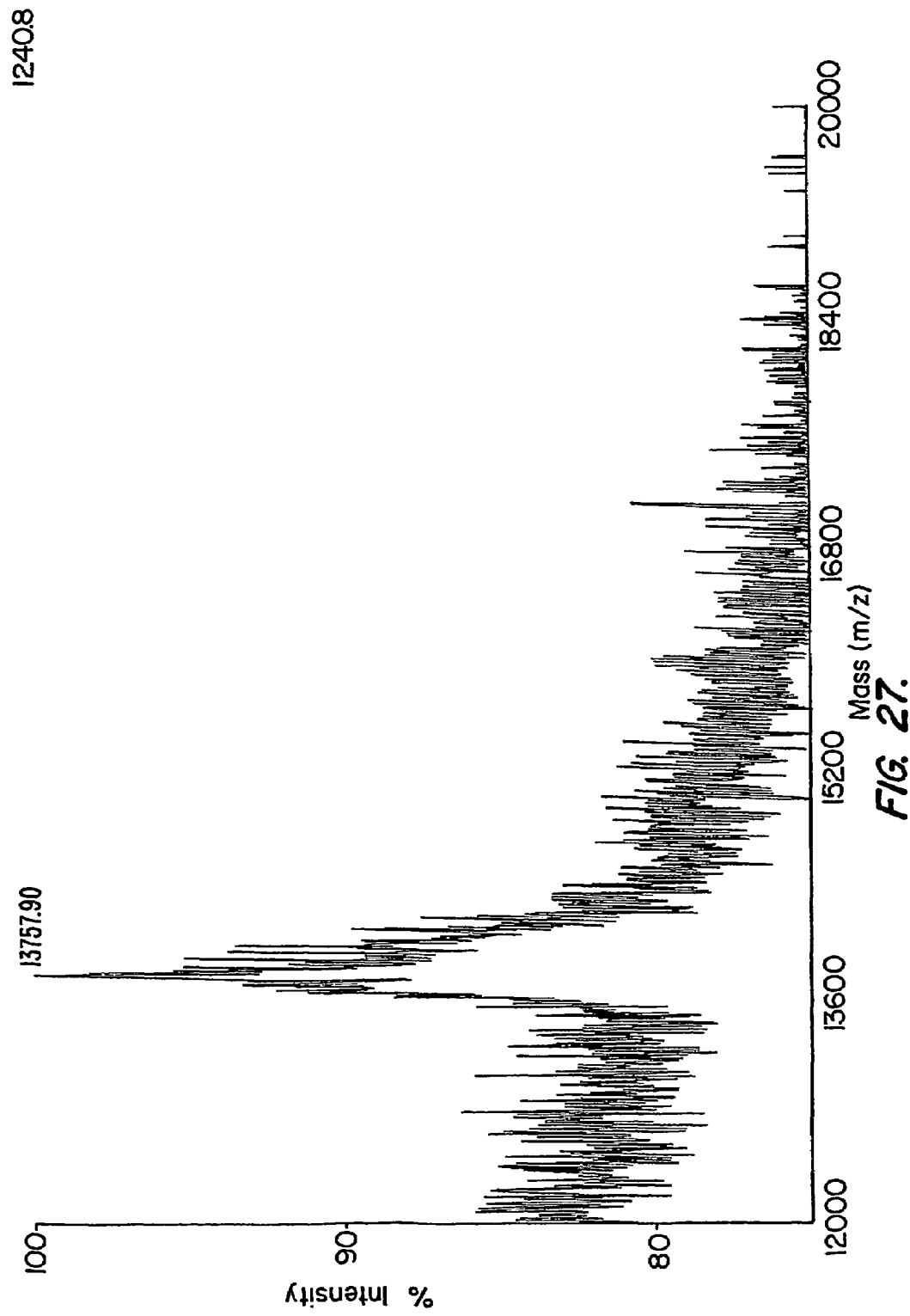
FIG. 27. In the same component II preparation as described in FIG. 26, an analysis by MALDI (matrix assisted laser desorption/ionization) time-of-flight mass-spectrum was conducted. These data indicated at mass of 13,757.9 Daltons. A single peak was observed. This preparation was used for protease assays.

The Direct Demonstration of Protease Activity of ADNF Component II with a Fluorogenic Peptide Substrate To demonstrate the protease activity in an ADNF I component, cell-free, enzyme assays utilizing a fluorogenic peptide substrate were performed. To demonstrate this principal, component II of ADNF I was chosen. Several assessments of the component II were made to establish the concentration, purity and identity of the protein preparation used for the protease assay. As shown in FIG. 26, an electropherogram of isolated component II was shown to be a single peak migrating at approximately 10 min in an N-CHO capillary electrophoresis column. This elution pattern is consistent with the 10 min peak being component II as described in our previous patent application. As shown in FIG. 27, this preparation of component II was shown to have a molecular weight of 13,757 Daltons as measured by matrix-assisted laser desorption/ionization mass spectrometry. Thus, the preparation of component II was shown to be a single peak of protein by both capillary electrophoresis and mass spectrometry.

Figure 28:
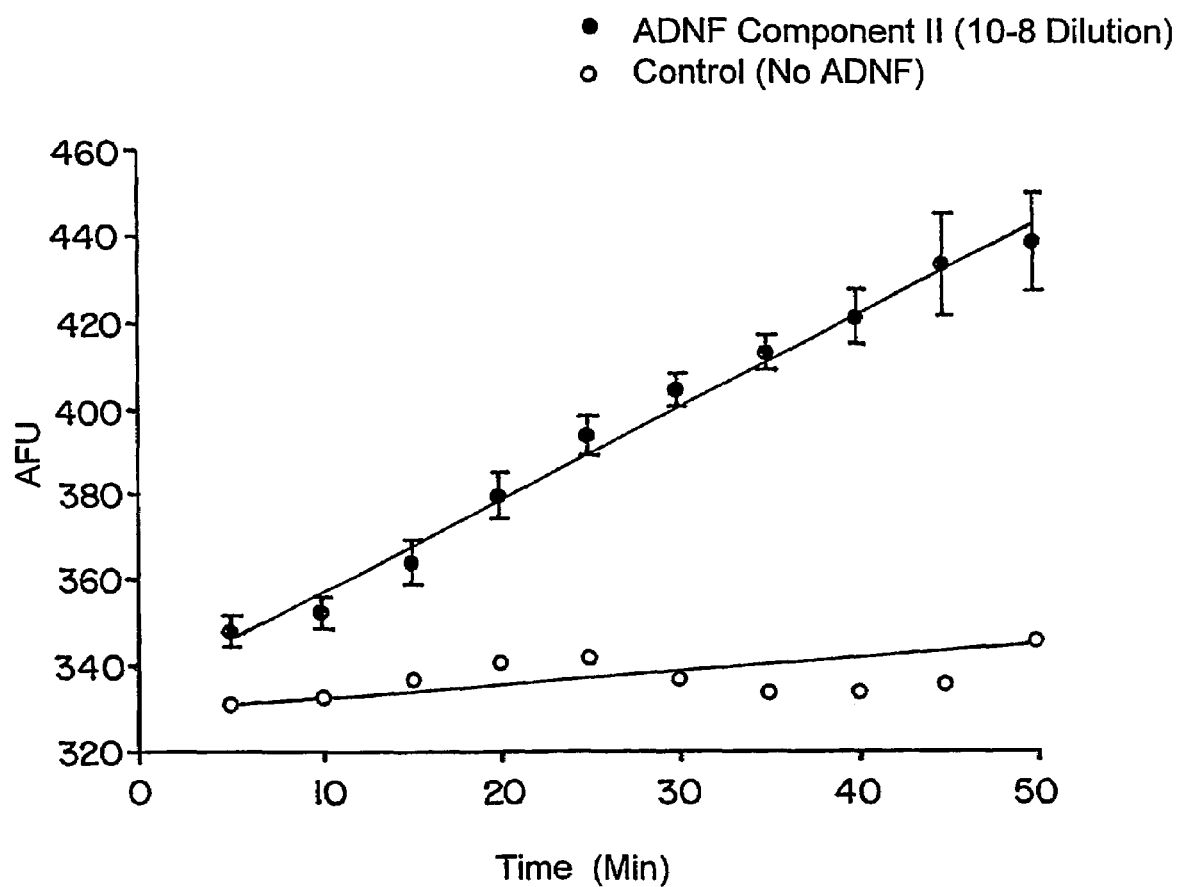
FIG. 28. A time course of component II (see FIGS. 26 and 27) in a cell-free protease assay using Bz-Arg-Gly-Phe-Phe-Pro-MβNA, HCl (Cathepsin D substrate). The conditions of the assay are as follows: 10 μl of substrate (5 mg dissolved in 100 μl of DMSO (dimethyl sulfoxide), diluted to 1 ml of water), 10 μl of 10 mM $CaCl_2$; 50 μl of component II ($10^{-8}$ dilution of the preparation characterized in FIGS. 26 and 27); and 30 μl of buffer (0.5 M dibasic phosphate, pH 7.8). For this assay, buffer, enzyme, calcium were added to 96 well culture trays. Based on glycoprotein alpha-1 acid standards on NCHO capillary, the optimum protease activity is observed at 1 fM amounts of components II.
Figure 29:
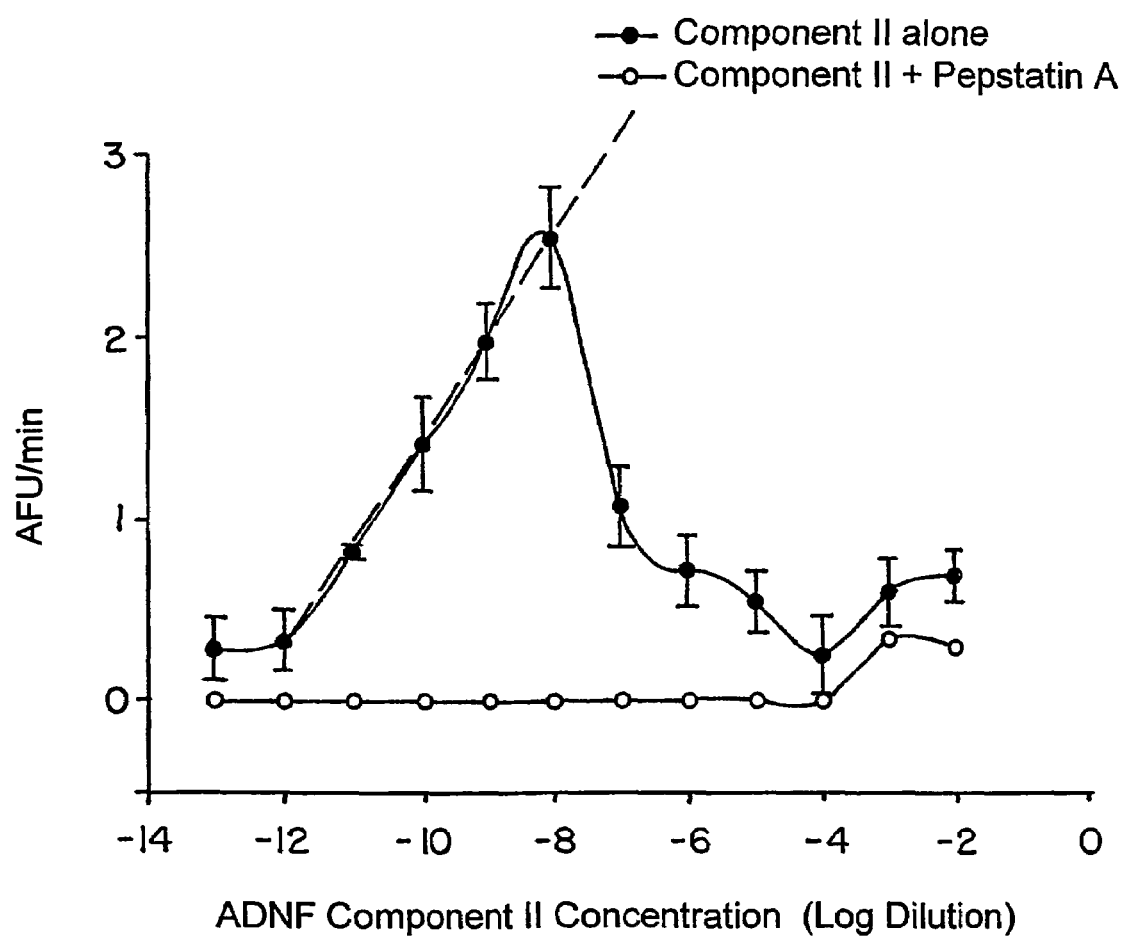
FIG. 29. Demonstration of linearity of component II concentration using a cell-free protease assay and the blockade of this activity with pepstatin A. The conditions for the protease assay were the same as that described for FIG. 28. In culture wells treated with pepstatin, 10 μl of the stock solution (1 mg dissolved in 1 ml of methanol, diluted 1:100 with water) was added. In control wells, an addition 10 ul of methanol/water (1:100 dilution in water) alone was added. Fluorescence changes indicative of peptide subtract cleavage were monitored as described in FIG. 28.
Figure 30:
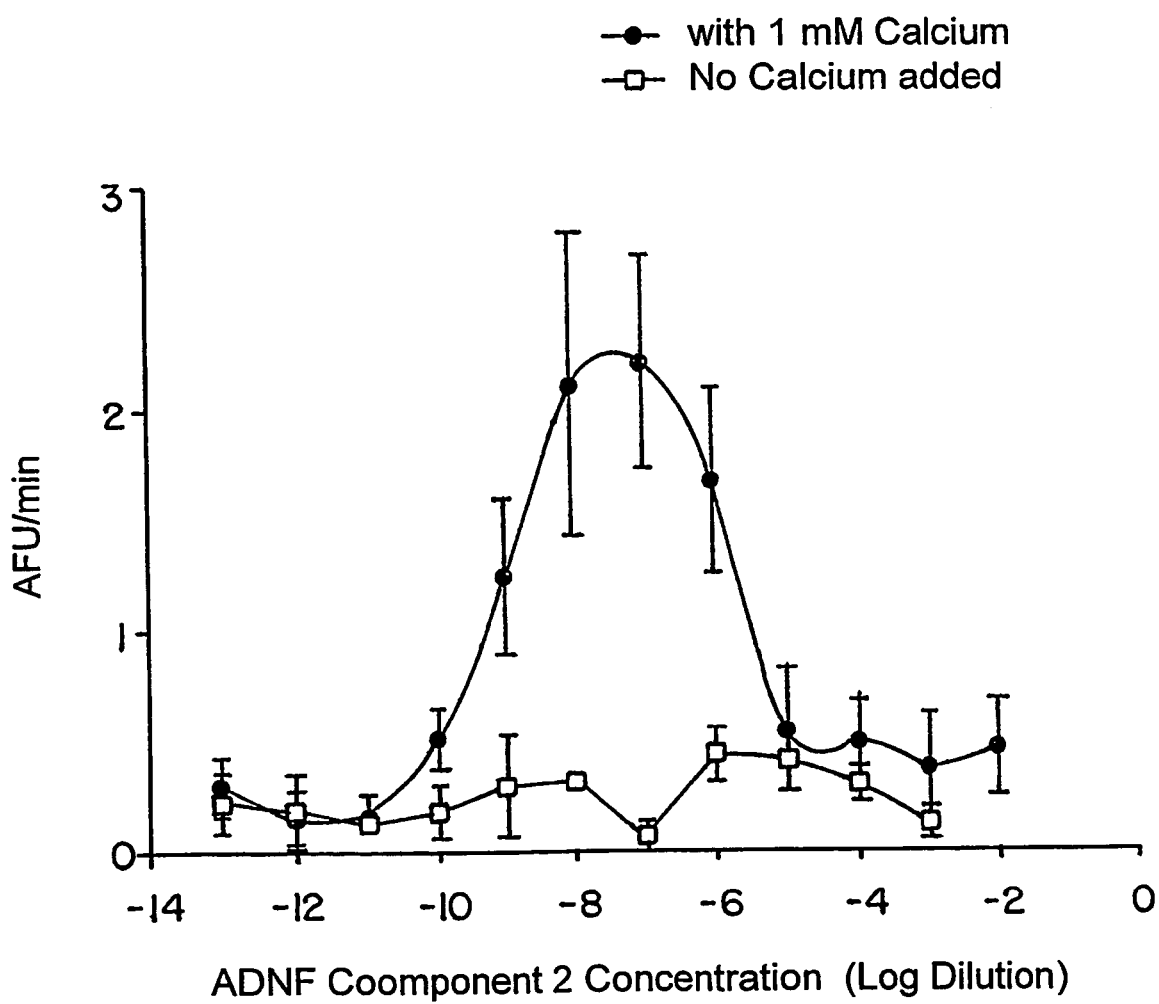
FIG. 30. Demonstration of calcium dependence for the protease activity detected in component II of the ADNF I complex. The conditions for the protease assay were the same as that described for FIG. 28 with the exception of the substitution of 10 ul of water in some wells rather than 10 ul of calcium chloride (10 mM stock). Each measurement is the mean of at least 3 determinations±standard error. Fluorescence changes indicative of peptide substrate cleavage were monitored as described in FIG. 28.
Figure 31:
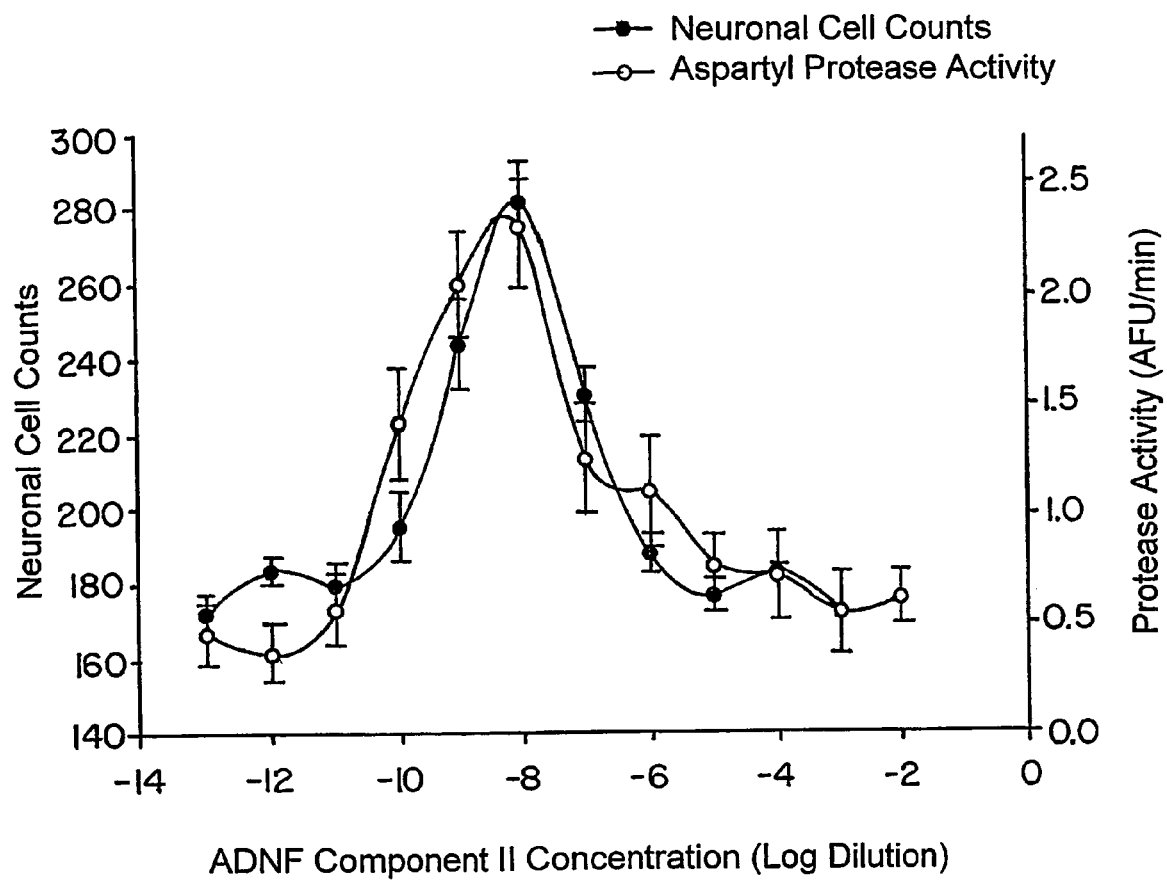
FIG. 31. Comparison of Survival-Promoting Activity and Protease Activity in the same preparation of component II of the ADNF I complex. The protease assay is described in FIG. 28 and the neuronal survival assay is described in FIG. 22. Excellent correlation between the two assays are observed.

As shown in FIG. 28, incubation of the component II preparation was shown to produce proteolytic activity with the use of the aspartyl protease substrate:

Bz-Arg-Gly-Phe-Phe-Pro-4MβNA HCl. Component II produced a linear increase in fluorescence for 50 min at 35 degrees C. Control assays without added component II had no activity. To further characterize component II protease activity, a concentration effect study was conducted (FIG. 29). A linear increase in protease activity was observed from $10^{-11}$ to $10^{-8}$ dilution; however, a dramatic decrease in the activity was shown for all component II concentrations >$10^{-8}$ dilution. To demonstrate the specificity of the protease activity, pepstatin A (an aspartyl protease inhibitor) was shown to prevent the component II-mediated increases in protease activity. These data indicate that component II is a pepstatin A-sensitive protease, consistent with this component being an aspartyl protease. Further studies indicated that component II required 1 mM calcium to produce protease activity (FIG. 30). No protease activity was observed with component II without the addition of 1 mM calcium to the assay. As shown in FIG. 31, the concentration effect curve of component was very similar in comparing its survival-promoting effects and its protease activity. Both dose response curves show high potency and abrupt attenuation at high concentrations of component II. These data give additional support to the conclusion that the survival-promoting activity of component II and ADNF I are mechanistically defined by protease activity.

Example VIII

Figure 32:
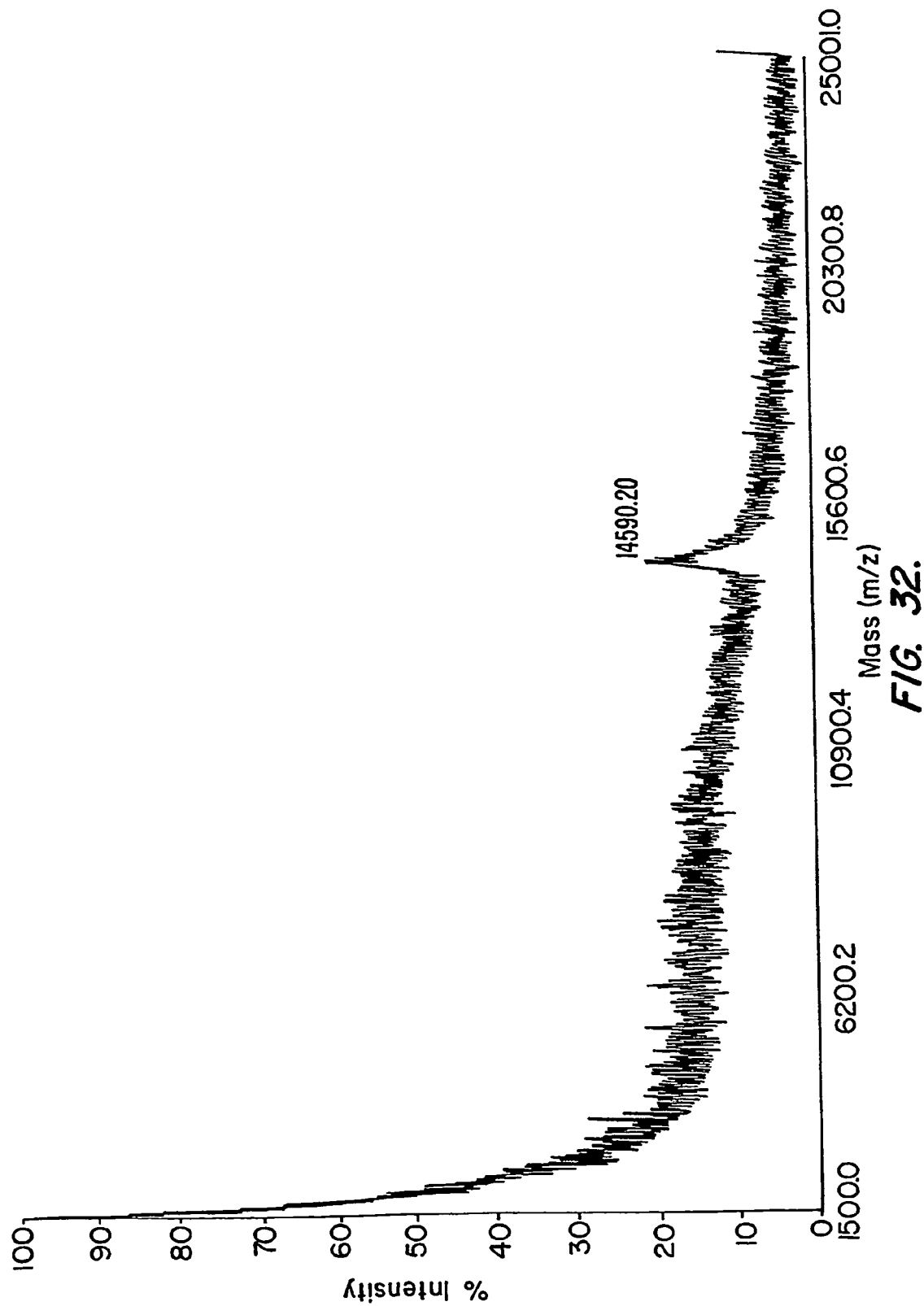
FIG. 32. MALDI time-of flight-mass spectrograph of immunopurified ADNF I. The molecular weight of the ADNF I complex is shown to be 14590 Daltons in a buffer of pH 7.0. This is the peak that is observed prior to increasing the pH and re-analyzing the preparation (see FIG. 33).
Figure 33:
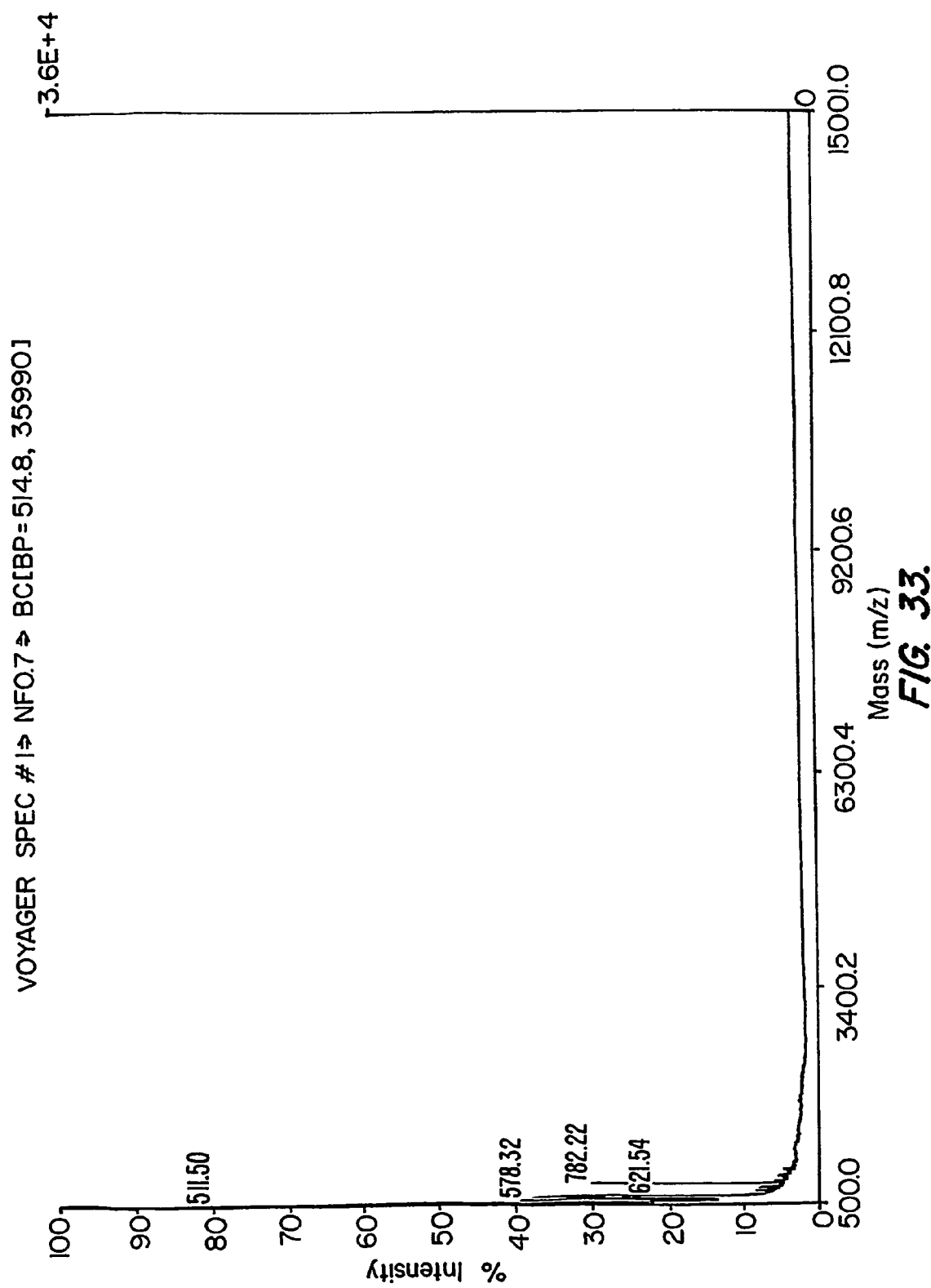
FIG. 33. MALDI time-of flight-mass spectrograph of immunopurified ADNF I after raising the pH to 8.0 for 30 min and then neutralizing back pH 7.0. The peak of ADNF I at 14590 is no longer detectable, suggesting an instability of ADNF I at high pH. This sensitivity to pH is thought to be due to the presence of a subtilisin-like protease that is activated at basic pH. The activation of this component of ADNF I results in the catalytic degradation MALDI time-of flight-mass spectrograph of ADNF I of the protein to amino acids and small peptides.

The Demonstration that a Subtilisin-Like Protease Exists that Serves to Inactivate the ADNF I Complex The ADNF I complex is highly unstable at pH>7.4, making this protein difficult to analyze. As suggested by the amino acid sequence homology to subtilisin (See section 1 above), the ADNF I complex could be inactivated by the action of an, intrinsic protease. To address this possibility, a MALDI mass spectrometric analysis was performed before and after raising the pH. For these experiments, affinity purified ADNF I complex was shown to be a broad protein peak with a molecular weight of 14,590 Daltons (FIG. 32) before pH manipulation. The ADNF I preparation was increased to pH 8 for 30 min, and then neutralized to pH 7 prior to performing MALDI analysis. As shown in FIG. 33, the pH manipulation resulted in the disappearance of the 14 kDa peak and the appearance of small peptides <800 Daltons. These data indicate the sensitivity of ADNF I to increased pH and provide evidence for an intrinsic protease that inactivates ADNF I by rapid proteolytic cleavage to small peptides.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. For example, any one or more of the features of the previously described embodiments can be combined in any manner with one or more features of any other embodiments in the present invention. The scope of the invention should, therefore, be determined not with reference to the above description, but instead should be determined with reference to the appended claims along with their full scope of equivalents.

---

What is claimed is:

1. An Activity Dependent Neurotrophic Factor I complex (ADNF I) polypeptide, the ADNF I complex polypeptide selected from the group consisting of:

NPSGTDWLNTNNQANPFN           (SEQ ID NO:4)
and

PSGTDWLNT;                   (SEQ ID NO:10)

wherein the ADNF I complex polypeptide has neuroprotective activity.

2. The ADNF I complex polypeptide of claim 1, wherein the polypeptide is covalently linked to a lipophilic moiety.

3. The ADNF I complex polypeptide of claim 2, wherein the lipophilic moiety is selected from the group consisting of fatty acyl groups and steroids.

4. The ADNF I complex polypeptide of claim 1, wherein the polypeptide comprises at least one D-amino acid.

5. The ADNF I complex polypeptide of claim 1, wherein either an N-terminal amino acid or a C-terminal amino acid of the polypeptide is a D-amino acid.

6. The ADNF I complex polypeptide of claim 1, wherein both N-terminal and C-terminal amino acids of the polypeptide are D-amino acids.

7. The ADNF I complex polypeptide of claim 1, wherein the polypeptide comprises all D-amino acids.

8. An ADNF I complex polypeptide, wherein the ADNF I complex polypeptide comprises up to about 20 amino acids at the N-terminus or the C-terminus or both of a polypeptide, wherein said polypeptide is selected from the group consisting of: NPSGTDWLNTNNQANPFN (SEQ ID NO: 4) and PSGTDWLNT (SEQ ID NO: 10); and wherein the ADNF I complex polypeptide has neuroprotective activity.

9. A composition comprising a pharmaceutically acceptable excipient and an Activity Dependent Neurotrophic Factor I complex (ADNF I) polypeptide, wherein the ADNF I complex polypeptide is selected from the group consisting of:

NPSGTDWLNTNNQANPFN           (SEQ ID NO:4)
and

PSGTDWLNT;                   (SEQ ID NO:10)

wherein the ADNF I complex polypeptide has neuroprotective activity.

10. The composition of claim 9, wherein the polypeptide is covalently linked to a lipophilic moiety.

11. The composition of claim 10, wherein the lipophilic moiety is selected from the group consisting of fatty acyl groups and steroids.

12. The composition of claim 9, wherein the ADNF I complex polypeptide comprises at least one D-amino acid.

13. The composition of claim 12, wherein either an N-terminal amino acid or a C-terminal amino acid of the ADNF I complex polypeptide is a D-amino acid.

14. The composition of claim 12, wherein both N-terminal and C-terminal amino acids of the ADNF I complex polypeptide are D-amino acids.

15. The composition of claim 12, wherein the ADNF I complex polypeptide comprises all D-amino acids.

16. A composition comprising a pharmaceutically acceptable excipient and an Activity Dependent Neurotrophic Factor I complex (ADNF I) polypeptide, wherein the ADNF I complex polypeptide comprises up to about 20 amino acids at the N-terminus or the C-terminus or both of a polypeptide, wherein said polypeptide is selected from the group consisting of: NPSGTDWLNTNNQANPFN (SEQ ID NO: 4) and PSGTDWLNT (SEQ ID NO: 10); and wherein the ADNF I complex polypeptide has neuroprotective activity.

* * * * *